US008815849B2

(12) United States Patent
Vandyck et al.

(10) Patent No.: US 8,815,849 B2
(45) Date of Patent: Aug. 26, 2014

(54) HETERO-BICYCLIC DERIVATIVES AS HCV INHIBITORS

(75) Inventors: Koen Vandyck, Paal-Beringen (BE); Wim Gaston Verschueren, Berchem (BE); Pierre Jean-Marie Bernard Raboisson, Rosieres (BE)

(73) Assignee: Janssen R&D Ireland, Little Island, Co Cork (IE)

( * ) Notice: Subject to any disclaimer, the term of this patent is extended or adjusted under 35 U.S.C. 154(b) by 0 days.

(21) Appl. No.: 13/812,388

(22) PCT Filed: Jul. 26, 2011

(86) PCT No.: PCT/EP2011/062774
§ 371 (c)(1),
(2), (4) Date: Jan. 25, 2013

(87) PCT Pub. No.: WO2012/013643
PCT Pub. Date: Feb. 2, 2012

(65) Prior Publication Data
US 2013/0123244 A1    May 16, 2013

(30) Foreign Application Priority Data

Jul. 26, 2010  (EP) .................................. 10170763
Dec. 23, 2010  (EP) .................................. 10196715
Mar. 31, 2011  (EP) .................................. 11160697

(51) Int. Cl.
| A61K 31/549 | (2006.01) |
| A61K 31/517 | (2006.01) |
| A61K 31/4709 | (2006.01) |
| A61K 31/4725 | (2006.01) |
| C07D 285/22 | (2006.01) |
| C07D 417/02 | (2006.01) |
| C07D 471/04 | (2006.01) |
| C07D 217/00 | (2006.01) |
| C07D 215/00 | (2006.01) |

(52) U.S. Cl.
USPC .................. 514/223.2; 514/266.23; 514/309; 514/312; 544/12; 544/284; 546/122; 546/141; 546/153

(58) Field of Classification Search
USPC ............ 514/223.2, 266.23, 309, 312; 544/12, 544/284; 546/122, 141, 153
See application file for complete search history.

(56) References Cited

FOREIGN PATENT DOCUMENTS

| WO | WO2004/005264 | 1/2004 | |
| WO | WO2006/133326 | 12/2006 | |
| WO | WO2007/039578 | 4/2007 | |
| WO | WO2008/021927 | 2/2008 | |
| WO | WO2008/021928 | 2/2008 | |
| WO | WO2008/021936 | 2/2008 | |
| WO | WO2008/048589 | 4/2008 | |
| WO | WO2008/070447 | 6/2008 | |
| WO | WO 2010/065764 | * 12/2009 | .................... 514/256 |
| WO | WO2010/017401 | 2/2010 | |
| WO | WO2010/065681 | 6/2010 | |

OTHER PUBLICATIONS

Genelot, Marie et al., "Optimised Procedures for the One-pot Selective Syntheses of Idoxyls and 4-Quinolones by a Carbonylative Sonogashira/Cyclisation Sequence" 2009, Applied Catalysis A: General 369 pp: 125-132.
Krieger, Nicole E. et al., "Enhancement of Hepatitis C. Virus RNA Replication by Cell Culture-Adaptive Mutations", 2001, Journal of Virology, vol. 75, No. 10, pp. 4614-4624.
Kumar, J.S. et al., "Simple and Chemoselective Reduction of Aromatic Nitro Compounds to Aromatic Amines; reduction with Hydriodic Acid Revisited" 2001, Tetrahedron Letters 42: 5601-5603.
Lohmann, V. et al., "Replication of Subgenomic Hepatitis C Virus RNAs in a Hepatoma Cell Line", 1999 Science vol. 285 pp. 110-113.
Wallen, Erik A., "Dicarboxylic Acid bis(L-Prolyl-pyrrolidine) Amides as Prolyl Oligopeptidase Inhibitors" 2002, J. Med. Chem 45 pp. 4581-4584.

* cited by examiner

Primary Examiner — Samantha Shterengarts

(57) ABSTRACT

Inhibitors of HCV replication of formula I

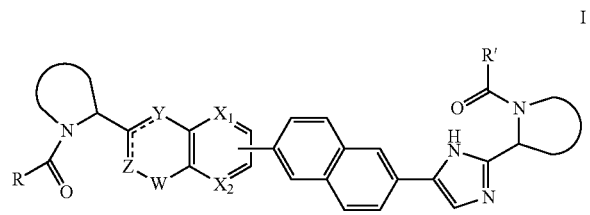

including stereochemically isomeric forms, and salts, hydrates, solvates thereof, wherein R and R' have the meaning as defined herein.
The present invention also relates to processes for preparing said compounds, pharmaceutical compositions containing them and their use, alone or in combination with other HCV inhibitors, in HCV therapy.

11 Claims, No Drawings

HETERO-BICYCLIC DERIVATIVES AS HCV INHIBITORS

This application is a national stage application of PCT/EP2011/062774, filed Jul. 26, 2011, which claims priority benefit of application Ser. No. EP 11160697.6 filed Mar. 31, 2011, which claims priority benefit of application Ser. No. EP 10196715.6 filed Dec. 23, 2010, which claims priority benefit of application Ser. No. EP 10170763.6 filed Jul. 26, 2010. The complete disclosures of the aforementioned related patent applications are hereby incorporated herein by reference for all purposes.

TECHNICAL FIELD

This invention relates to hetero-bicyclic derivatives, in particular quinolinone derivatives, which are inhibitors of the hepatitis C virus (HCV), their synthesis and their use, alone or in combination with other HCV inhibitors, in the treatment or prophylaxis of HCV.

BACKGROUND ART

HCV is a single stranded, positive-sense RNA virus belonging to the Flaviviridae family of viruses in the hepacivirus genus. The viral genome translates into a single open reading frame that encodes for multiple structural and non-structural proteins.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in 40% of patients infected by genotype 1 HCV and about 80% of those infected by genotypes 2 and 3. Beside the limited efficacy on HCV genotype 1, this combination therapy has significant side effects including influenza-like symptoms, hematologic abnormalities, and neuropsychiatric symptoms. Hence there is a need for more effective, more convenient and better-tolerated treatments.

Experience with HIV drugs, in particular with HIV protease inhibitors, has taught that sub-optimal pharmacokinetics and complex dosing regimens quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the pharmacokinetics and rate of drug metabolism necessary to allow such trough levels provides a stringent challenge to drug design.

The NS5A protein of HCV is located downstream of the NS4B protein and upstream of the NS5B protein. Upon post-translational cleavage by the viral serine protease NS3/4A, the NS5A matures into a zinc containing, three-domain phosphoprotein that either exists as a hypophosphorylated (56-kDa, p56) or hyperphosphorylated species (58-kDa, p58). NS5A of HCV is implicated in multiple aspects of the viral lifecycle including viral replication and infectious particle assembly as well as modulation of the environment of its host cell. Although no enzymatic function has been ascribed to the protein it is reported to interact with numerous viral and cellular factors.

A number of patents and patent applications disclose compounds with HCV inhibitory activity, in particular targeting NS5A. WO2006/133326 discloses stilbene derivatives while WO 2008/021927 and WO 2008/021928 disclose biphenyl derivatives having NS5A HCV inhibitory activity. WO 2008/048589 discloses 4-(phenylethynyl)-1H-pyrazole derivatives and their antiviral use. WO 2008/070447 discloses a broad range of HCV inhibiting compounds including a benzimidazole moiety. WO-2010/017401 and WO-2010/065681 both disclose bis-imidazole inhibitors of HCV NS5A.

There is a need for HCV inhibitors that may overcome the disadvantages of current HCV therapy such as side effects, limited efficacy, the emerging of resistance, and compliance failures, as well as improve the sustained viral load response.

The present invention concerns a group of HCV inhibiting hetero-bicyclic derivatives, in particular quinolinone derivatives, with useful properties regarding one or more of the following parameters: antiviral efficacy, favorable profile of resistance development, reduced or lack of toxicity and genotoxicity, favorable pharmacokinetics and pharmacodynamics, ease of formulation and administration, and limited or lack of drug-drug interactions with other drug substances, in particular other anti-HCV agents.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect, the present invention provides compounds, which can be represented by the formula I:

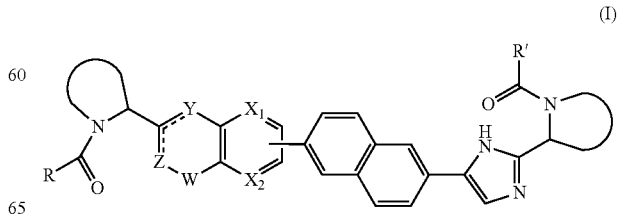

including any possible stereoisomers thereof, wherein: each

independently is pyrrolidin-2-yl, 2-aza-bicyclo[3.1.0]hexan-3-yl, piperidin-2-yl, 2-aza-bicyclo[2.2.1]heptan-2-yl or octahydro-1H-indol-2-yl, wherein each of said heterocycles may optionally be substituted by one or more halogen atoms;

Z---C---Y is $CR_4$=C—NH, NH—C=CH or NH—C=N;

$X_1$ is CH and $X_2$ is CH; or $X_1$ is CH and $X_2$ is N; or $X_1$ is N and $X_2$ is CH;

W is carbonyl, sulfonyl or $CR_5R_6$;

R and R' are independently selected from —$CR_1R_2R_3$, aryl optionally substituted with 1 or 2 substituents selected from halo and methyl, or heterocycloalkyl, wherein $R_1$ is selected from $C_{1-4}$alkyl optionally substituted with methoxy, hydroxyl or dimethylamino; $C_{3-6}$cycloalkyl; tetrahydropyranyl; phenyl optionally substituted with 1, 2 or 3 substituents independently selected from halo, $C_{1-4}$alkoxy, trifluoromethoxy or 2 substituents on adjacent ring atoms form a 1,3-dioxolane group; benzyl optionally substituted with halo or methoxy; heteroaryl; and heteroarylmethyl;

$R_2$ is selected from hydrogen, hydroxyl, amino, mono- or di-$C_{1-4}$alkylamino, ($C_{3-6}$cycloalkyl)($C_{1-4}$alkyl)amino, $C_{1-4}$alkylcarbonylamino, phenylamino, $C_{1-4}$alkyloxycarbonylamino, ($C_{1-4}$alkyloxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and $R_3$ is hydrogen or $C_{1-4}$alkyl, or $CR_2R_3$ together forms carbonyl; or $CR_1R_3$ forms a cyclopropyl group;

$R_4$ is hydrogen, $C_{1-4}$alkyl or cyano;

$R_5$ and $R_6$, each independently, are $C_{1-4}$alkyl; or $CR_5R_6$ together form $C_{3-7}$cycloalkyl, oxetane, tetrahydrofurane;

or a pharmaceutically acceptable salts or a solvate thereof.

In another aspect, the present invention provides compounds which can be represented by the formula (I')

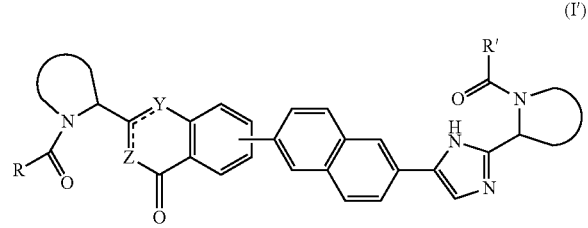

(I')

including any possible stereoisomers thereof, wherein: each

independently is pyrrolidin-2-yl, 2-aza-bicyclo[3.1.0]hexan-3-yl, piperidin-2-yl, 2-aza-bicyclo[2.2.1]heptan-2-yl or octahydro-1H-indol-2-yl;

Z---C---Y is CH=C—NH, NH—C=CH or NH—C=N;

R and R' are independently selected from —$CR_1R_2R_3$, aryl optionally substituted with 1 or 2 substituents selected from halo and methyl, or heterocycloalkyl, wherein $R_1$ is selected from $C_{1-4}$alkyl optionally substituted with methoxy, hydroxyl or dimethylamino; $C_{3-6}$cycloalkyl; tetrahydropyranyl; phenyl optionally substituted with 1, 2 or 3 substituents independently selected from halo, $C_{1-4}$alkoxy, trifluoromethoxy or 2 substituents on adjacent ring atoms form a 1,3-dioxolane group; benzyl optionally substituted with halo or methoxy; heteroaryl; and heteroarylmethyl;

$R_2$ is selected from hydrogen, hydroxyl, amino, mono- or di-$C_{1-4}$alkylamino, ($C_{3-6}$cycloalkyl)($C_{1-4}$alkyl)amino, $C_{1-4}$alkylcarbonylamino, phenylamino, $C_{1-4}$alkyloxycarbonylamino, ($C_{1-4}$alkyloxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and $R_3$ is hydrogen or $C_{1-4}$alkyl, or $CR_2R_3$ together forms carbonyl; or $CR_1R_3$ forms a cyclopropyl group;

and the pharmaceutically acceptable salts and the solvates thereof.

In a further aspect, the invention concerns the use of compounds of formula I, or sub-groups thereof, as specified herein, for inhibiting HCV. Alternatively, there is provided the use of said compounds for the manufacture of a medicament for inhibiting HCV.

In a first embodiment of the present invention, each

independently is pyrrolidin-2-yl, 2-aza-bicyclo[3.1.0]hexan-3-yl or piperidin-2-yl, wherein each of said heterocycles may optionally be substituted by one or more halogen atoms.

In a second embodiment of the present invention, each

independently is pyrrolidin-2-yl or 2-aza-bicyclo[3.1.0]hexan-3-yl, wherein each of said heterocycles may optionally be substituted by one or more halogen atoms.

In a third embodiment of the present invention Z---C---Y is CH=C—NH.

In a further embodiment R and R' are identical.

In yet a further embodiment $R_2$ is hydroxyl, amino, mono- or di-$C_{1-4}$alkylamino, $C_{1-4}$alkyl-carbonylamino, $C_{1-4}$alkyloxycarbonylamino; in particular, $R_2$ is $C_{1-4}$alkylcarbonylamino or $C_{1-4}$alkyloxycarbonylamino, and $R^3$ is hydrogen.

In a further embodiment $R_1$ is selected from $C_{1-4}$alkyl; $C_{2-4}$alkyl substituted with methoxy or hydroxyl; and phenyl optionally substituted with 1 or 2 substituents independently selected from halo and methyl. In particular, $R_1$ is selected from branched $C_{3-4}$alkyl; $C_{2-3}$alkyl substituted with methoxy; and phenyl optionally substituted with 1 substituent selected from halo and methyl.

In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include but are not limited to genotype 1b (prevalent in Europe) and 1a (prevalent in North America). The invention also provides a method for the treatment or prophylaxis of HCV infection, in particular of the genotype 1a or 1b, comprising administering to a subject in need thereof, a therapeutically effective amount of a compound as defined hereinbefore.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula I and subgroups of compounds of formula I as defined hereinbefore have several centers of chirality. Of interest are the stereogenic centers of the pyrrolidine ring at the 2-carbon atom. The configuration at this position may be that corresponding to L-proline, i.e.

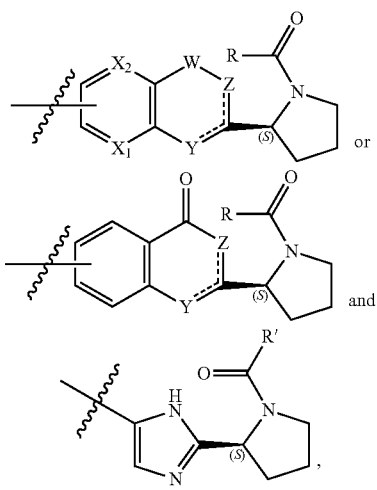

or that corresponding to D-proline, i.e.

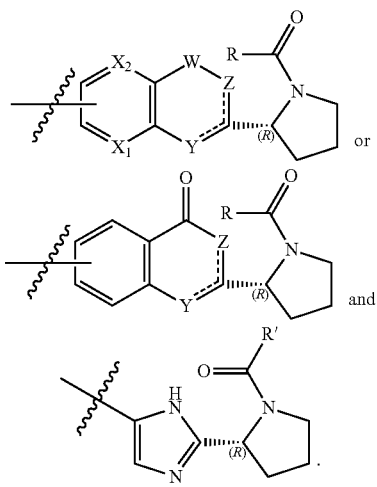

Of particular interest are compounds of formula I or subgroups thereof as defined herein, that are according to formula Ia.

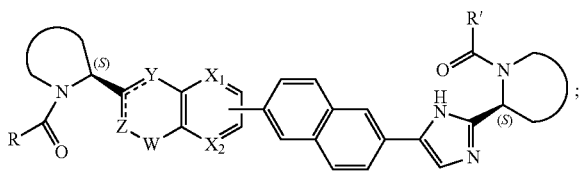

more in particular

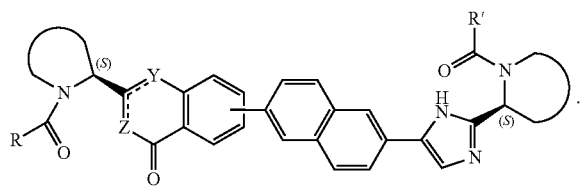

Also of interest is the configuration of the group —CR$_1$R$_2$R$_3$: when R$_1$ is selected from C$_{1-4}$alkyl optionally substituted with methoxy, hydroxyl or dimethylamino; C$_{3-6}$cyclo-alkyl; and tetrahydropyranyl, then the S-configuration is preferred; when R$_1$ is selected from phenyl optionally substituted with 1, 2 or 3 substituents independently selected from halo, C$_{1-4}$alkoxy, trifluoromethoxy or 2 substituents on adjacent ring atoms form a 1,3-dioxolane group; and heteroaryl; then the R-configuration is preferred.

The pharmaceutically acceptable addition salts comprise the therapeutically active non-toxic acid and base addition salt forms of the compounds of formula (I) or subgroups thereof. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their base addition salts, in particular metal or amine addition salt forms, by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

As used herein, "C$_{1-4}$alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl. For the purpose of the present invention, of interest amongst C$_{1-4}$alkyl is C$_{3-4}$alkyl, i.e. straight or branched chain hydrocarbon groups having 3 or 4 carbon atoms such as 1-propyl, 2-propyl, 1-butyl, 2-butyl, 2-methyl-1-propyl, 2-methyl-2-propyl. Of particular interest may be branched C$_{3-4}$alkyl such as 2-propyl, 2-butyl, 2-methyl-1-propyl, 2-methyl-2-propyl.

The term "C$_{3-6}$cycloalkyl" as a group or part thereof, defines saturated cyclic hydrocarbon groups having from 3 to 6 carbon atoms that together form a cyclic structure. Examples of C$_{3-6}$cycloalkyl include cyclopropyl, cyclobutyl, cyclopentyl and cyclohexyl.

"C$_{1-4}$alkoxy" as a group or part of a group means a group of formula —O—C$_{1-4}$alkyl wherein C$_{1-4}$alkyl is as defined above. Examples of C$_{1-4}$alkoxy are methoxy, ethoxy, n-propoxy, isopropoxy.

The term "halo" is generic to fluoro, chloro, bromo and iodo.

As used herein, the term "(=O)" or "oxo" forms a carbonyl moiety when attached to a carbon atom. It should be noted that an atom can only be substituted with an oxo group when the valency of that atom so permits.

As used herein for the purpose of defining "aryl" as a group or part thereof means an aromatic ring structure optionally comprising one or two heteroatoms selected from N, O and S, in particular from N and O. Said aromatic ring structure may have 5 or 6 ring atoms.

As used herein, the prefix "hetero-" in the definition of a group means that the group comprises at least 1 heteroatom selected from N, O and S, in particular N and O. For example, the term "heteroaryl" means an aromatic ring structure as defined for the term "aryl" comprising at least 1 heteroatom selected from N, O and S, in particular from N and O, for example furanyl, oxazolyl, pyridinyl. Alternatively, the term "heteroC$_{3-6}$cycloalkyl" means saturated cyclic hydrocarbon group as defined for "C$_{3-6}$cycloalkyl" further comprising at least 1 heteroatom selected from N, O and S, in particular from N and O, for example tetrahydrofuranyl, tetrahydropyranyl, piperidinyl.

Where the position of a group on a molecular moiety is not specified (for example a substituent on phenyl) or is represented by a floating bond, such group may be positioned on any atom of such a moiety, as long as the resulting structure is chemically stable. When any variable is present more than once in the molecule, each definition is independent.

Whenever used herein, the term "compounds of formula I", or "the present compounds" or similar terms, it is meant to include the compounds of formula I, including the possible stereoisomeric forms, and the pharmaceutically acceptable salts and solvates thereof.

General Synthetic Methods

Scheme 1

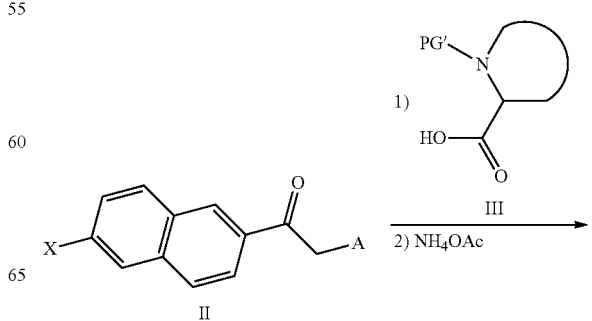

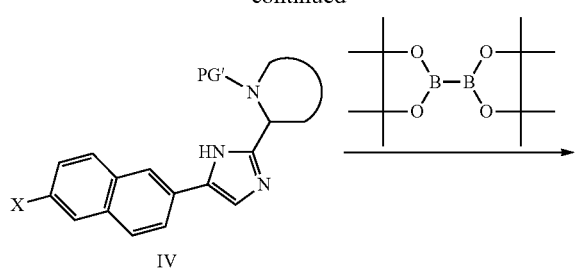

IV

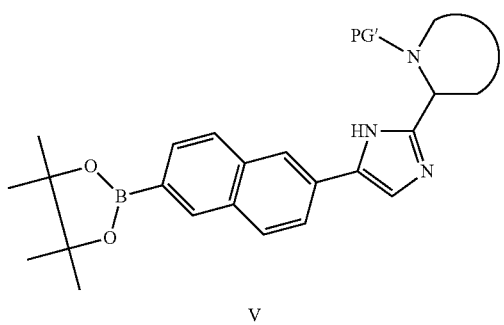

V

Building blocks used in the synthesis of compounds of formula I are described in scheme 1. α-Amino ketone IIa (Scheme 1, A=NH$_2$), with X a halogen, in particular bromo or iodo, is coupled with a suitably protected derivative III, wherein PG' is a protective group on the nitrogen, preferably tert-butoxycarbonyl, in the presence of a coupling reagent for amino-group acylation, preferably HATU, in the presence of a base such as DIPEA. The thus formed intermediate is cyclized to an imidazole compound of general formula IV by treatment with ammonium acetate, preferably at a temperature ranging between 0° C. and 150° C.

Alternatively, the intermediate imidazole IV can be obtained by coupling an α-halo ketone IIb wherein X and A each independently represent a halo atom, X preferably selected from iodo or bromo and A preferably selected from chloro, bromo or iodo, with a suitably protected compound III wherein PG' is a protective group on the nitrogen, preferably tert-butoxycarbonyl, in the presence of a suitable base, for example DIPEA, followed by cyclization to the imidazole intermediate IV as described above. This intermediate IV can be transformed to a boronic ester of formula V under Pd catalyzed conditions, for example in the presence of Pd(dppf)Cl$_2$, bis(pinacolato)diboron and a base, for example potassium acetate.

Other building blocks are described in schemes 2a, 2b, 2c and 3a, 3b, 3c, 3d.

Scheme 2a

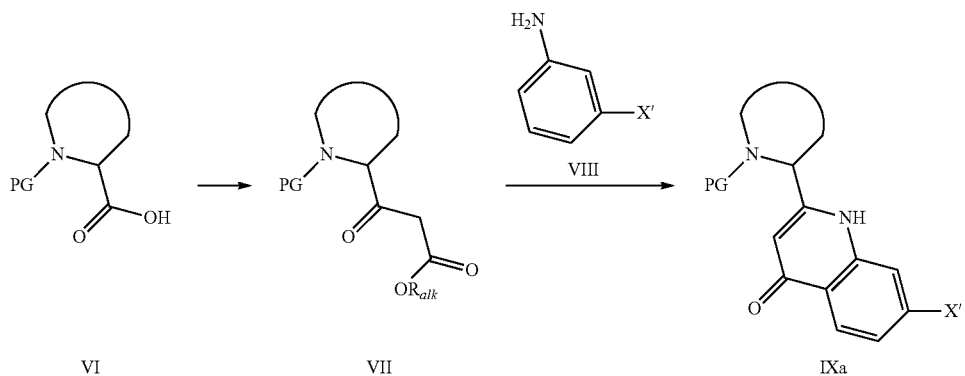

VI        VII        IXa

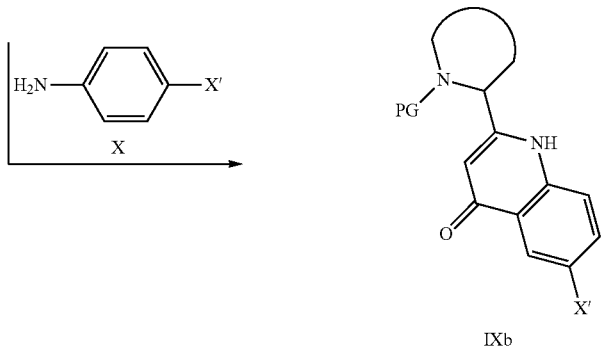

IXb

In scheme 2a, the acid derivative VI is converted into an β-ketoester VII by methods known in literature, for example, by activation of the carboxylic acid with DCC or CDI, followed by, for example, reaction with Meldrum's acid and subsequent decarboxylation in the presence of an alcohol, or as an alternative, as described in the examples, by condensation with a monoalkyl malonate magnesium salt followed by decarboxylation. The β-ketoester VII ($R_{alk}$ referring to $C_{1-4}$alkyl) is then condensed with VIII or X, followed by cyclisation to IXa and IXb respectively (X' is a halogen selected from iodo or bromo, preferably bromo). This condensation can be performed in toluene in the presence of acetic acid. Cyclisation to the compounds of formula IXa and IXb, can be performed thermally by refluxing in Dowtherm™ A (blend of diphenyl oxide and biphenyl). A preferred example of the protecting group PG is benzyloxycarbonyl (CBz).

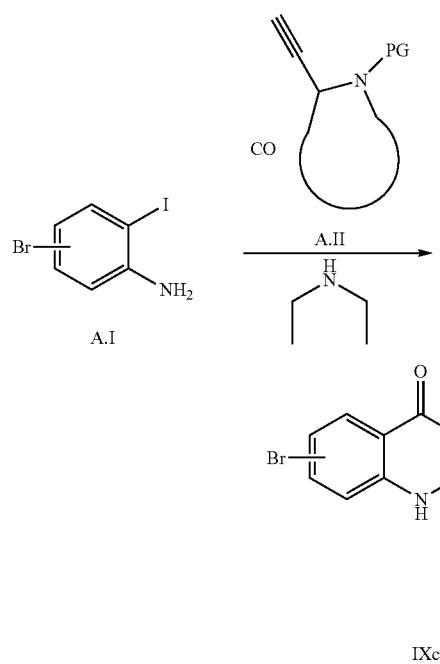

Scheme 2b

Alternatively compounds of the general formula IXc can be obtained by a Pd catalyzed carbonylative Sonogashira/ cyclization sequence as described in Scheme 2b. Starting from iodo-aniline compound A.I, under procedures similar as described in *Applied Catalysis, A: General* 2009, 369, 1-2, 125-132 and references cited therein.

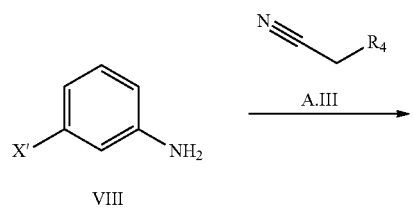

Scheme 2c

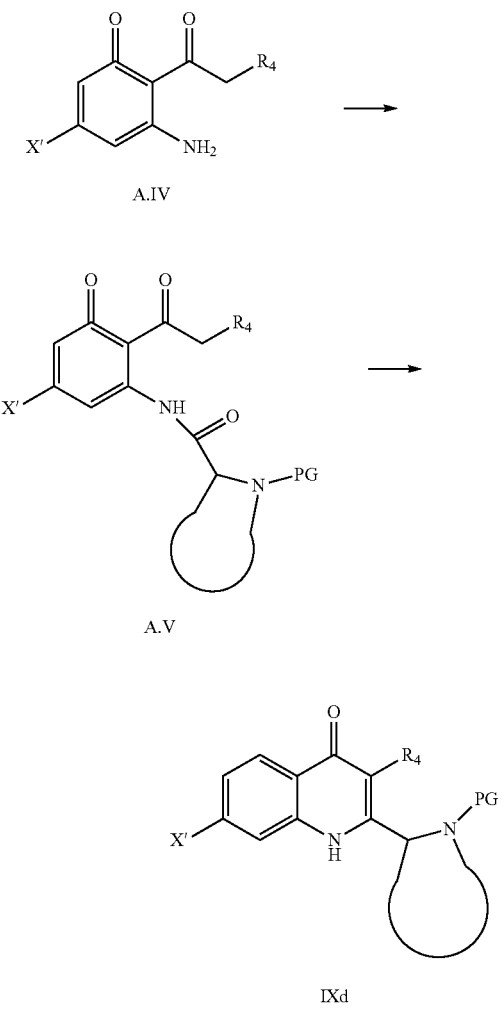

Compounds of the general formula IXd, were $R_4$ equals H or $C_{1-4}$alkyl, can be obtained as shown in scheme 2c. Compound VIII (X' is a halogen selected from iodo or bromo, preferably bromo) can be converted to compound A.IV, for example by treatment of VIII with $BCl_3$ in a solvent like benzene at a temperature lower then room temperature, for example by ice cooling, followed by treatment with $AlCl_3$ and nitrile A.III ($R_4$ equals H or $C_{1-4}$alkyl) for example at reflux in benzene. After hydrolysis, compound A.IV can be obtained. Amide bond formation starting from A.IV and VI results in the formation of compound A.V. This reaction can be effected by converting compound VI to an acid halogenide, for example an acid fluoride or acid chloride, followed by reaction with A.IV in the presence of a base. Another example is the formation of A.V from VI and A.IV by use of the coupling reagent 4-(4,6-Dimethoxy[1.3.5]triazin-2-yl)-4-methylmorpholinium chloride hydrate (DMTMM). Cyclisation of A.V, under basic conditions, for example KOH in EtOH, or NaOH in dioxane, results in compound IXd

Scheme 3a

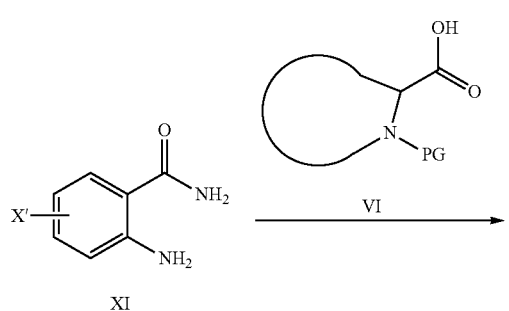

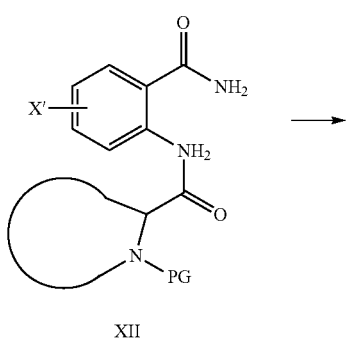

The synthesis of compounds of the formula XIII is described in Scheme 3a. Amide bond formation starting from XI (X' is a halogen selected from iodo or bromo, preferably bromo) and VI results in the formation of compound XII. This reaction can be effected by converting compound VI to an acid halogenide, for example an acid fluoride or acid chloride followed by reaction with XI in the presence of a base. Another example is the formation of XII from VI and XI by use of the coupling reagent 4-(4,6-Dimethoxy[1.3.5]triazin-2-yl)-4-methylmorpholinium chloride hydrate (DMTMM). Compounds XII are then converted to compounds of the general formula XIII under basic conditions, for example KOH in ethanol.

Scheme 3b

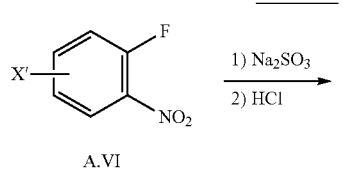

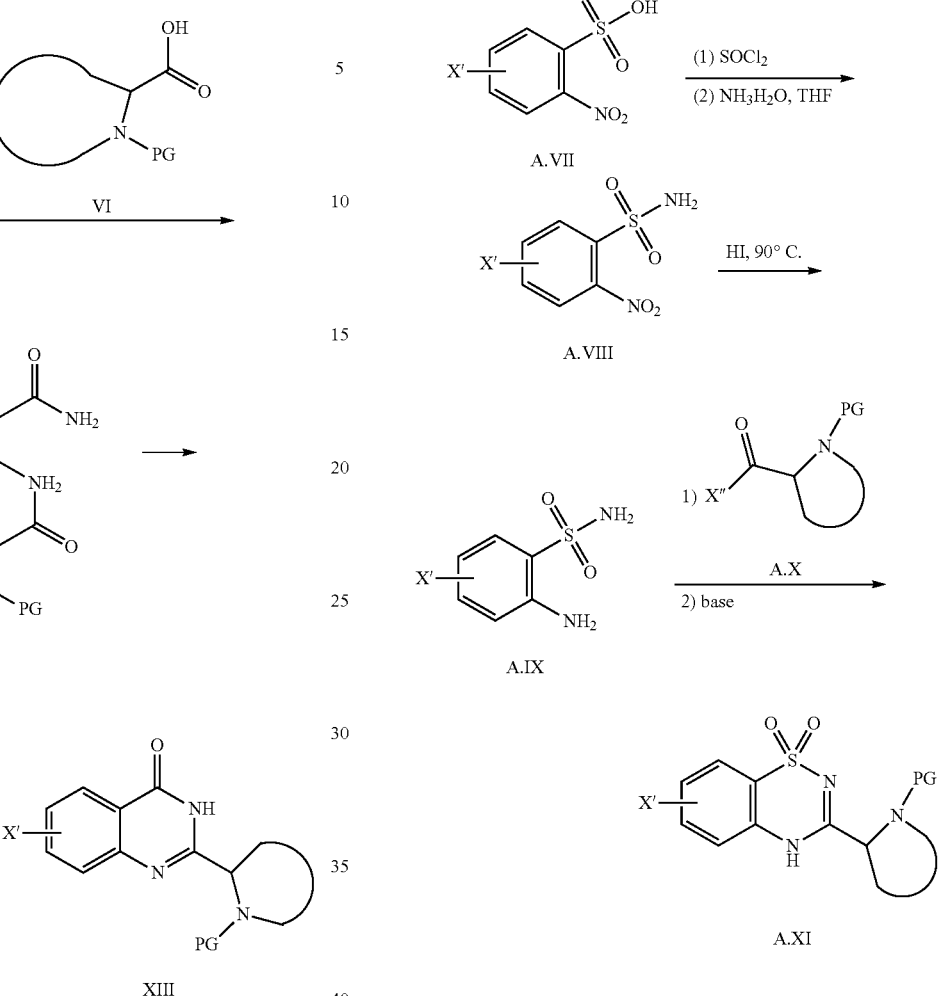

Compound of general formula A.XI (X' is a halogen selected from iodo or bromo, preferably bromo) can be obtained as shown in scheme 3b. Using methods described in literature (WO2007039578; Tet. Lett. 2001, 42, 33, 5601-5603), fluoride A.VI can be converted to A.IX. The latter is coupled with and acid halogenide A.X (where X" equals chloro or fluoro) in the presence of a base, for example triethylamine, followed by cyclization to compound A.XI under basic conditions like for example 2N aqueous K$_2$CO$_3$ at reflux.

Scheme 3c

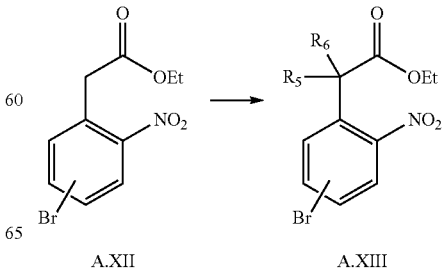

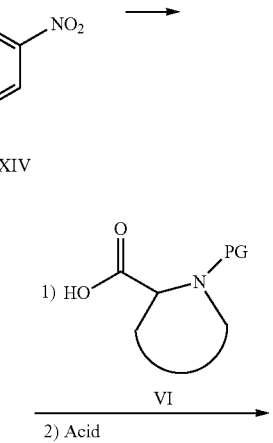

A.XIV

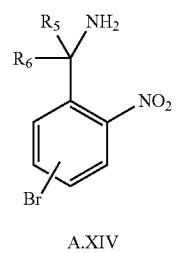

A.XIV

An alternative procedure for the synthesis of compound A.XIV (for example in case $R_5$ and $R_6$ together with the carbon that connects them, form an oxetane) is depicted in scheme 3d. The anion, generated by transmetalation reaction of for example buthyllithium and compound A.XVII at low temperature, for example −78° C., can be reacted with a sulfineamide A.XVIII. After deprotection of the formed sulfineamide, under acidic conditions, compound A.XIV is obtained, which can be further transformed to A.XVI as described in Scheme 3c.

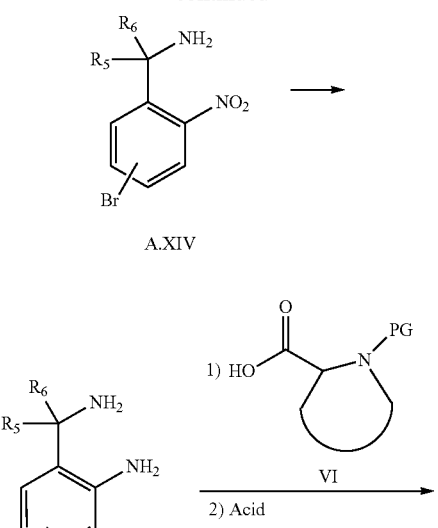

A.XV

A.XVI

Compound of general formula A.XVI can be obtained as shown in scheme 3c. Dialkylation of ester A.XII with the appropriate alkylhalogenide, for example MeI in the case $R_5=R_6=$Methyl, in the presence of a base, for example NaH, results in compound A.XIII. This ester can be converted to compound A.XIV by subsequent hydrolysis, acyl azide formation (for example by treatment of the corresponding acid of A.XIII with diphenylphosphoryl azide) and Curtius reaction. After reduction of compound A.XIV to A.XV, the latter compound is converted to compound A.XVI by coupling with acid VI, for example by treatment with HATU and a base like triethylamine, and subsequent cyclisation to compound A.XVI under acidic conditions, for example in acetic acid at 50° C.

Scheme 4

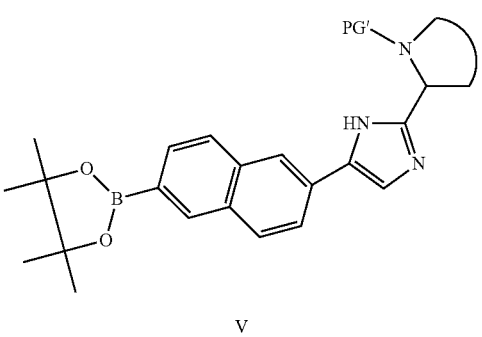

A.XIX

V

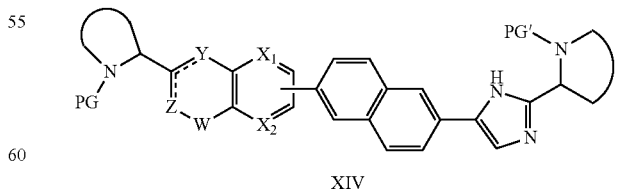

XIV

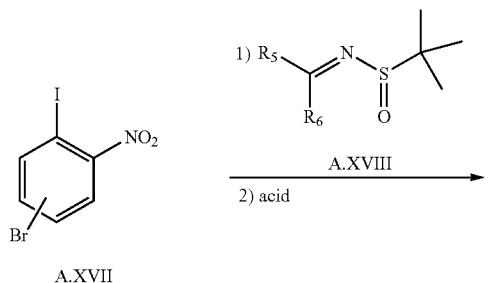

Scheme 3d

A.XVII

The building blocks A.XIX, obtained by methods similar as described in schemes 2 (a, b, c) and schemes 3 (a, b, c and d) and V (Scheme 1). can be converted to structure XIV, using Suzuki-Miyaura conditions (scheme 4).

Scheme 5
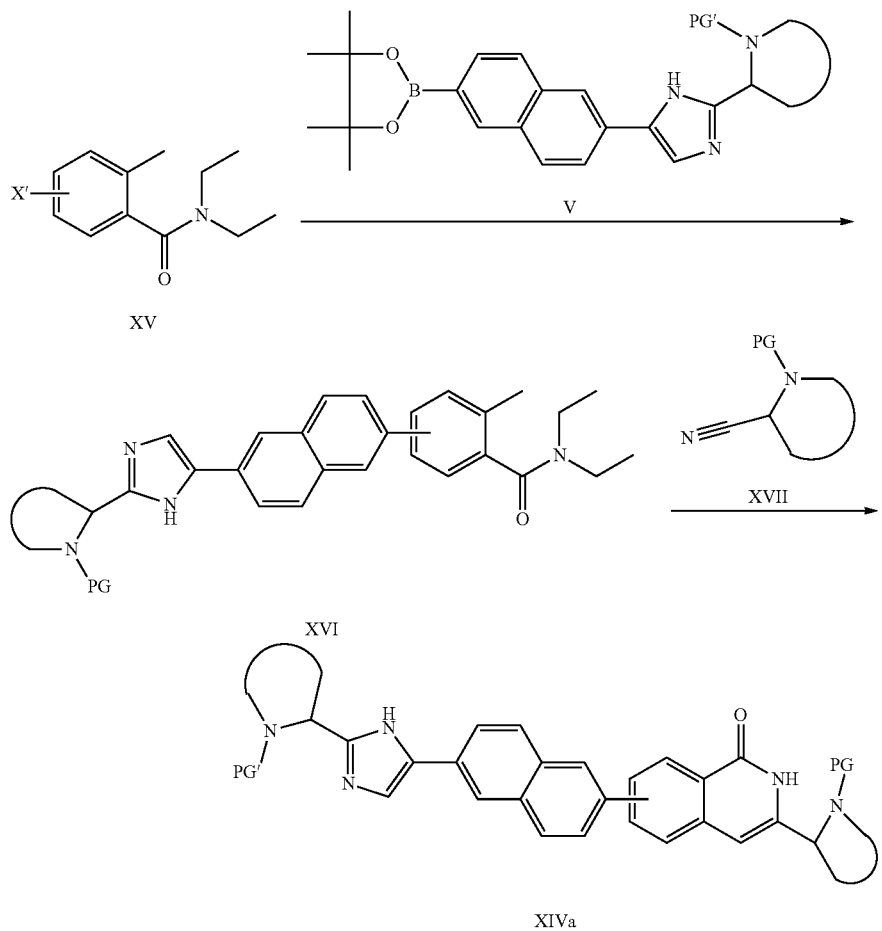
The synthesis of compounds of general formula XIVa is described in Scheme 5. Suzuki-Miyaura coupling between a halogenide XV and boronic ester V, results in intermediate XVI, which can be converted to XIVa by treatment with base, for example butyllithium, and reaction with XVII.
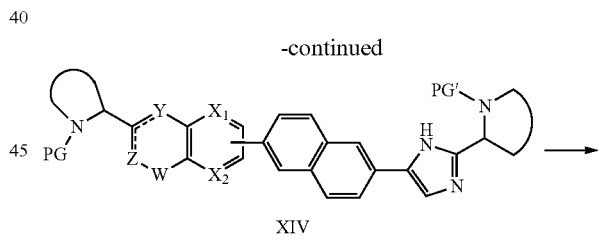
Scheme 6
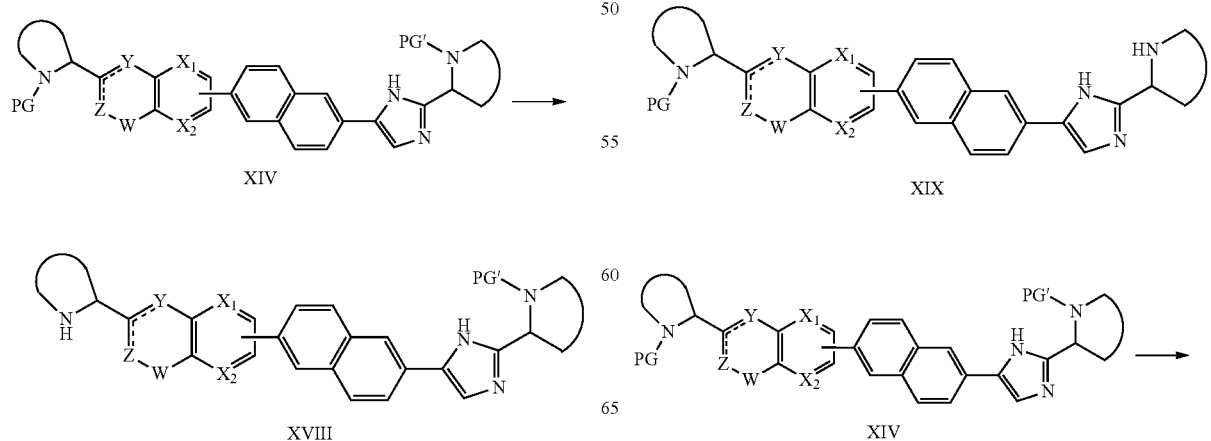

-continued

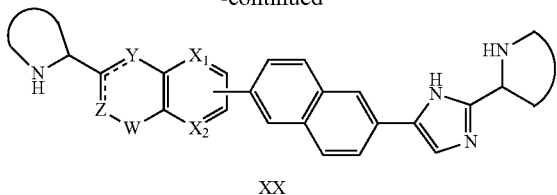

XX

When PG' and PG in schemes 1 to 6 represent R'(C=O)— and R(C=O)— respectively, compounds of general structure XIV fall under the definition of compounds of formula I. In that case schemes 4 and 5 describe the synthesis of compounds of formula I.

Alternatively, XIV can be deprotected as described in scheme 6. For example by treatment with acid (for example HCl in iPrOH) when PG or PG' represent tert butyloxycarbonyl (Boc). Compound XX can be transformed to a compound of formula Ib wherein R and R' are identical, by classical amide formation between an acid R—(C=O)OH and bisamine XX as described in scheme 7. A preferred method is the use of HATU in the presence of a base like DIPEA.

XVIII or XIX starting from XIV. For example in case PG' equals tert-butyloxycarbonyl (Boc) and PG equals benzyloxycarbonyl (Cbz), selective deprotection can be effected by removing the Boc-protective group under acidic conditions like HCl in iPrOH at room temperature, or by removing the CBz-protective group under reducing conditions like hydrogen in the presence of a catalyst, e.g. Pd(OH)$_2$.

When PG' represents R'(C=O)— or PG represents R(C=O)—, the synthesis of compounds XIV as described in scheme 1 to 5 results in compounds of formula XXI (Scheme 8) or XXIII (Scheme 9) respectively. Compounds XXI and XXIII can be obtained from compound XIX and R'(C=O)OH or XVIII and R(C=O)OH respectively, under typical amide formation conditions. These compounds can then be transformed to compounds of formula I. Selective deprotection of XXI to XXII followed by amide bond formation between XXII and R(C=O)—OH results in compounds of the formula I. An analogous reaction sequence can then be

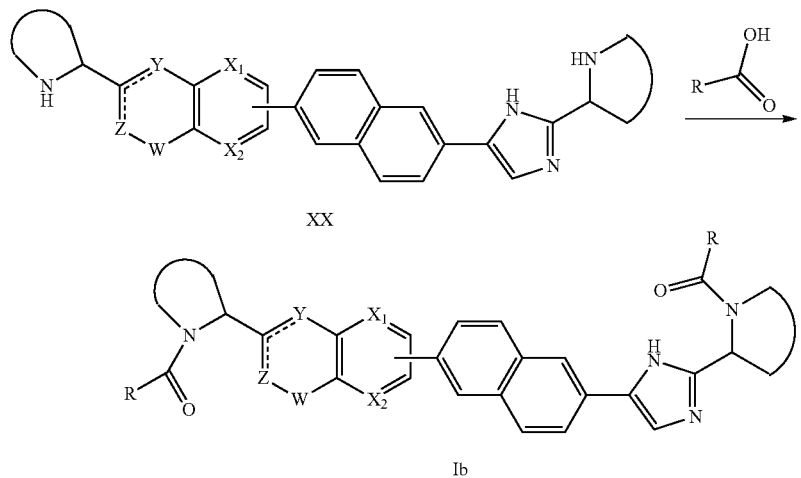

Ib

Where PG' differs from PG, selective deprotection is possible, as described in scheme 6, resulting in compounds applied to transform XXIII into XXIV and onwards to compounds of formula I.

Scheme 8

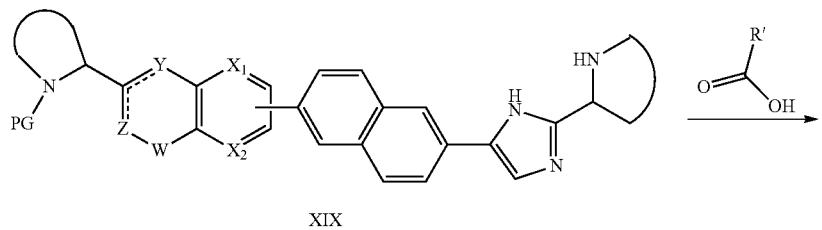

XIX

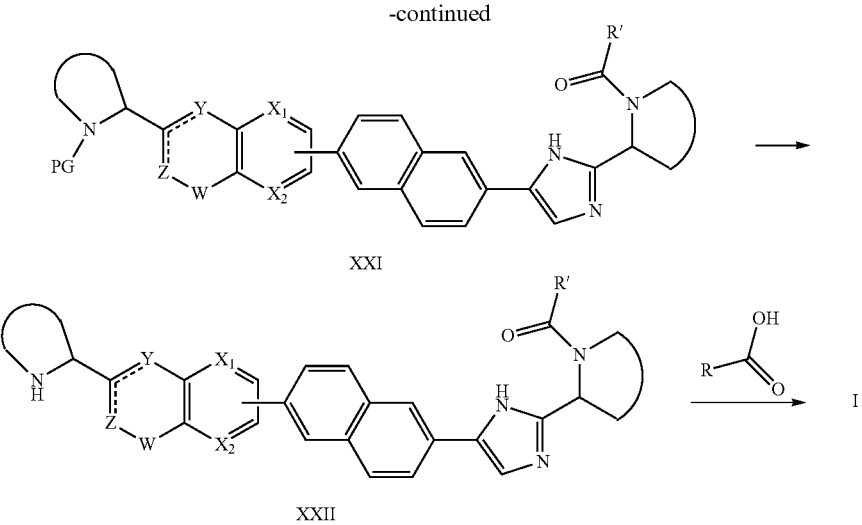

XXI

XXII

Scheme 9

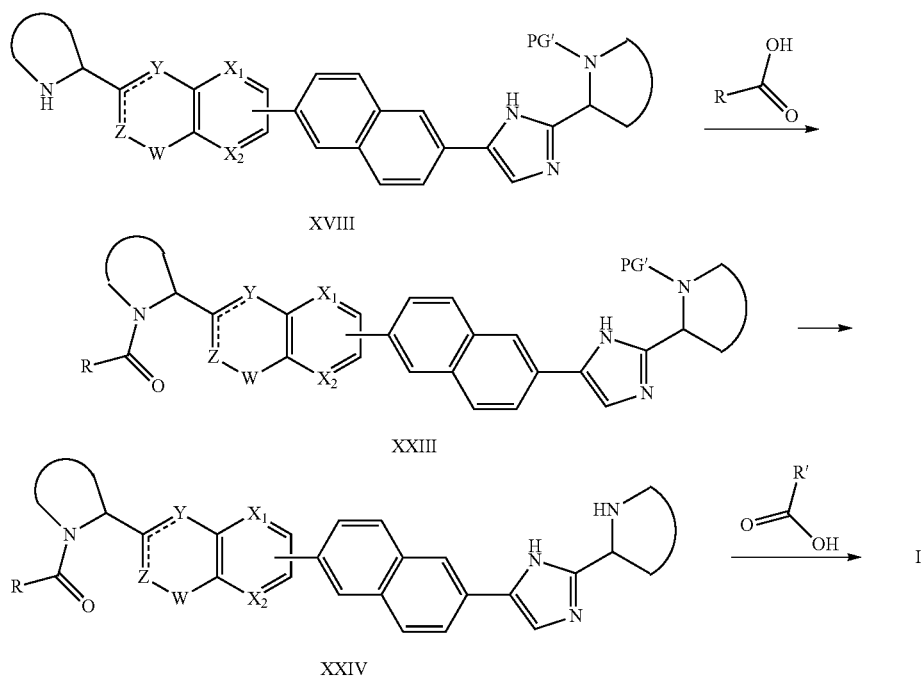

XVIII

XXIII

XXIV

In a further aspect, the present invention concerns a pharmaceutical composition comprising a therapeutically effective amount of a compound of formula I as specified herein, and a pharmaceutically acceptable carrier. A therapeutically effective amount in this context is an amount sufficient to stabilize or to reduce HCV infection in infected subjects, or an amount sufficient to prevent HCV infection in subjects at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and hepatocellular carcinoma. A number of the compounds of this invention moreover are known to be active against mutated strains of HCV. Additionally, compounds of this invention may have attractive properties in terms of bioavailability, show a favorable pharmacokinetic profile, including an acceptable half-life, AUC (area under the curve), peak and trough values, and lack unfavorable phenomena such as insufficiently rapid onset or tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their anti-HCV properties, the compounds of formula I or subgroups thereof, as specified herein, are useful in the inhibition of HCV replication, in particular in the treatment of warm-blooded animals, in particular humans, infected with HCV, and for the prophylaxis of HCV infections in warm-blooded animals, in particular humans. The present invention furthermore relates to a method of treating a warm-blooded animal, in particular a human, infected by HCV, or being at risk of infection by HCV, said method comprising the administration of a therapeutically or prophylactively effective amount of a compound of formula I, as defined hereinbefore.

The compounds of formula I as specified herein may therefore be used as a medicine, in particular as an anti-HCV medicine. Said use as a medicine or method of treatment comprises the systemic administration to HCV infected subjects or to subjects susceptible to HCV infection of an amount effective to relieve or prevent the symptoms and conditions associated with HCV infection.

The present invention also relates to the use of the present compounds in the manufacture of a medicament for the treatment or the prevention of HCV infection.

In general it is contemplated that an effective antiviral daily amount would be from about 0.01 to about 50 mg/kg, or about 0.02 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

Combination Therapy

The invention also relates to a combination of a compound of formula I, a pharmaceutically acceptable salt or solvate thereof, and another antiviral compound, in particular another anti-HCV compound. The term "combination" relates to a product containing (a) a compound of formula I, as defined hereinbefore, and (b) another anti-HCV inhibitor, as a combined preparation for simultaneous, separate or sequential use in the treatment of HCV infections.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy in particular comprising a compound of formula (I) and at least one other anti-HCV agent, e.g. IFN-α, pegylated IFN-α, ribavirin, albuferon, taribavirin, nitazoxanide Debio025 or a combination thereof.

Other agents that may be combined with the compounds of the present invention include, for example, nucleoside and non-nucleoside inhibitors of the HCV polymerase, protease inhibitors, helicase inhibitors, NS4B inhibitors and agents that functionally inhibit the internal ribosomal entry site (IRES) and other agents that inhibit HCV cell attachment or virus entry, HCV RNA translation, HCV RNA transcription, replication or HCV maturation, assembly or virus release. Specific compounds in these classes include HCV protease inhibitors such as telaprevir (VX-950), boceprevir (SCH-503034), narlaprevir (SCH-900518), ITMN-191 (R-7227), TMC-435350 (TMC-435), MK-7009, BI-201335, BI-2061 (ciluprevir), BMS-650032, ACH-1625, ACH-1095, GS 9256, VX-985, IDX-375, VX-500, VX-813, PHX-1766, PHX2054, IDX-136, IDX-316, ABT-450, EP-013420 (and congeners) and VBY-376; the nucleoside HCV polymerase inhibitors useful in the invention include TMC649128, R7128, PSI-7851, PSI 7977, IDX-189, IDX-184, IDX-102, R1479, UNX-08189, PSI-6130, PSI-938 and PSI-879 and various other nucleoside and nucleotide analogs and HCV inhibitors including those derived as 2'-C-methyl modified nucleosides, 4'-aza modified nucleosides, and 7'-deaza modified nucleosides. Non-nucleoside HCV polymerase inhibitors useful in the invention include HCV-796, HCV-371, VCH-759, VCH-916, VCH-222, ANA-598, MK-3281, ABT-333, ABT-072, PF-00868554, BI-207127, GS-9190, A-837093, JKT-109, GL-59728, GL-60667, ABT-072, AZD-2795 and TMC647055.

The following examples are meant to illustrate the invention and should not be construed as a limitation of its scope.

Experimental Part

LCMS Methods

Method A: General: mobile phase A: $H_2O$ (0.1% TFA; B: $CH_3CN$ (0.05% TFA) Stop Time: 2 min; gradient time(min) [% A/% B] 0.01 [90/10] to 0.9 [20/80] to 1.5 [20/80] to 1.51 [90/10]; flow: 1.2 mL/min; column temp.: 50° C.

Method A1: Shimadzu LCMS 2010, Shim-pack XR-ODS, 3*30 mm

Method A2: Xtimate C18 2.1*30 mm, 3 um

Method A3: SHIMADZU Shim pack 2*30

Method A4: Welch Xtimate C18 2.1*30 mm, 3 um

Method B: Agilent 1100, YMC-PACK ODS-AQ, 50×2.0 mm 5 μm mobile phase A: $H_2O$ (0.1% TFA; B: $CH_3CN$ (0.05% TFA Stop Time: 10 min; gradient time(min) [% A/% B] 0 [100/0] to 1 [100/0] to 5 [40/60] to 7.5 [40/60] to 8 [100/0]; flow: 0.8mL/min; column temp.: 50° C.

Method C: Agilent 1100, YMC-PACK ODS-AQ, 50×2.0 mm 5 μm mobile phase A: $H_2O$ (0.1% TFA; B: $CH_3CN$ (0.05% TFA); Stop Time: 10 min; gradient time(min) [% A/% B] 0 [90/10] to 0.8 [90/10] to 4.5 [20/80] to 7.5 [20/80] to 8 [90/10]; flow: 0.8mL/min; column temp.: 50° C.

Method D: Shimadzu LCMS 2010, Shim-pack XR-ODS, 3*30 mm, mobile phase A: $H_2O$ (0.1% TFA; B: $CH_3CN$ (0.05% TFA) Stop Time: 2 min; gradient time(min) [% A/% B] 0.01 [100/0] to 0.9 [70/30] to 1.5 [70/30] to 1.51 [100/0]; flow: 1.2 mL/min; column temp.: 50° C.

Method E: Liquid Chromatography: Waters Alliance 2695, UV detector: Waters 996 PDA, range: 210-400 nm; Mass detector: Waters ZQ, ion source: ES+, ES− Column used: SunFire C18 3.5 g 4.6×100 mm mobile phase A: 10 mM $NH_4OOCH+0.1\%$ HCOOH in $H_2O$; mobile phase B: $CH_3OH$; column temp.: 50° C.; flow: 1.5 mL/min. gradient time(min) [% A/% B] 0 [65/35] to 7[5/95] to 9.6[5/95] to 9.8[65/35] to 12 [65/35].

Method F: Xtimate C18 2.1*30 mm, 3 um, mobile phase A: $H_2O$ (1.5 mL TFA/4 L); B: $CH_3CN$ (0.75 mL TFA/4 L) Stop Time: 3 min; gradient time(min) [% A/% B] 0.0 [90/10] to 1.35 [20/80] to 2.25 [20/80] to 2.26 [90/10]; 3.0 [90/10] flow: 0.8 mL/min; column temp.: 50° C.

Method G: General conditions: mobile phase A: $H_2O$ (1.5 mL TFA/4 L); B: $CH_3CN$ (0.75 mL TFA/4 L) Stop Time: 2 min; gradient time(min) [% A/% B] 0.0 [100/0] to 0.9 [40/60] to 1.5 [40/60] to 1.51 [100/0]; 2.0 [100/0] flow: 1.2 mL/min; column temp.: 50° C.

Method G1: Xtimate C18, 2.1*30 mm, 3 um

Preparation of the Intermediates

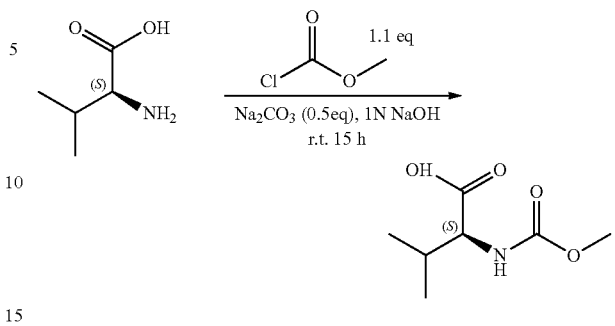

1N NaOH in water (1250 mL) was added into to L-Valine (150 g, 1280 mmol) in a 3 L round bottom flask equipped with a magnetic stir bar. To this solution was added $Na_2CO_3$ (67.8 g, 640 mmol) and the reaction mixture was cooled to 0° C. in an ice-water bath. Methyl chloroformate (107 mL, 1390 mmol) was added dropwise and the reaction mixture was allowed to warm to room temperature. The reaction mixture was stirred for 15 hours. The reaction mixture was washed with ethyl acetate (3×400 mL). The aqueous layer was cooled over an ice-water bath and acidified by concentrated HCl (aq) to pH=2. The reaction mixture was extracted with $CH_2Cl_2$ (3×1000 mL). The combined organic layers were dried over $Na_2SO_4$ and the solvent was concentrated to afford the crude product. The crude product was heated at reflux with 150 mL ethanol and 150 mL water for 2 hours. Then the mixture was cooled to room temperature and the crystalline solids were filtered to give (S)-2-(methoxycarbonylamino)-3-methyl-butanoic acid (146 g, 65% yield).

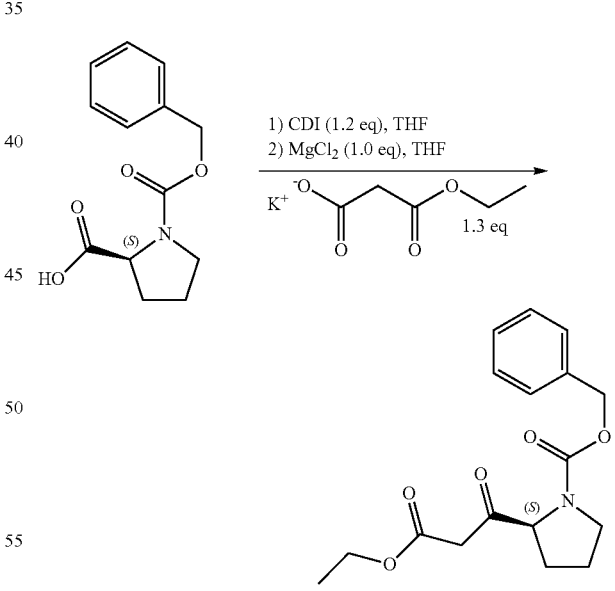

$MgCl_2$ (153 g, 1640 mmol) was added in one portion to a solution of ethyl potassium malonate (354.9 g, 2085 mmol) in THF (2500 mL). The reaction mixture was stirred for 7 h at 65-70° C. and then at 30° C. overnight. A solution of Cbz-L-Proline (400 g) in THF (1000 mL) was slowly added to a mixture of CDI (312.1 g, 1924.8 mmol) in THF (1500 mL) and stirred at 30° C. for 2 h. The solution was added to the ethyl malonate mixture over 20 min at 20-30° C. and stirred overnight at 30° C. The mixture was cooled to 20° C. and neutralized with diluted HCl (4 N, 1800 mL). The solution was concentrated and the product was dissolved in ethyl acetate and rinsed with 5% aqueous sodium bicarbonate. The organic layer was concentrated and the residue was purified by flash column chromatography (eluent: petroleum ether: ethyl acetate=20:1 to 3:1) to give pure (S)-benzyl 2-(3-ethoxy-3-oxopropanoyl)pyrrolidine-1-carboxylate (460 g, 90% yield). Method A4 Rt: 1.23 min. m/z: 341.9 (M+Na)$^+$ Exact mass: 319.1

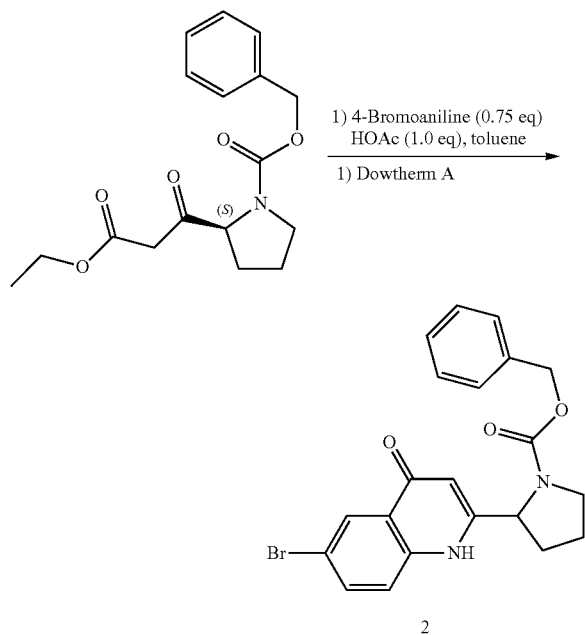

4-Bromoaniline (40 g, 235 mmol) was added to a mixture of (S)-benzyl 2-(3-ethoxy-3-oxopropanoyl)pyrrolidine-1-carboxylate (100 g, 313 mmol) in toluene (800 mL) containing acetic acid (16.7 mL, 313 mmol) and refluxed for 6 hours using a Dean Stark apparatus to remove the reaction water. The solvent was removed and the residue, containing condensation intermediate 1, was dissolved in Dowtherm™ A (260 mL). The mixture was stirred at 235° C. for 1.5 hours. The reaction mixture was cooled to room temperature, and ether (800 mL) followed by heptane (500 mL) was added. An oily residue precipitated and the solvent was decanted. The residue was by flash column chromatography (eluent: CH$_2$Cl$_2$: ethyl acetate=1:1) resulting in compound 2 (28 g, 11% overall yield). Method A3; Rt: 1.31 min. m/z: 428.9 (M+H)$^+$ Exact mass: 428.1

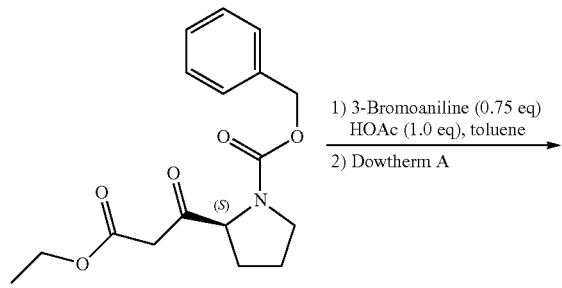

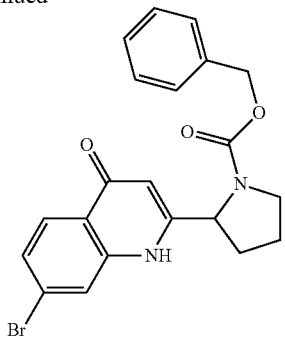

3-Bromoaniline (186 g, 1080 mmol) was added to a mixture of (S)-benzyl 2-(3-ethoxy-3-oxopropanoyl)pyrrolidine-1-carboxylate ((460 g, 1440 mmol) in toluene containing acetic acid (86.4 g, 1440 mmol) and was refluxed for 8 hours using a Dean Stark apparatus to remove the reaction water. The mixture was concentrated under reduced pressure and dried under vacuum. The crude product was used in the next step without further purification (662 g). A flask fitted with a stirrer, distillation head and dropping funnel was purged with nitrogen. Dowtherm™ A (90 mL) was added and then was heated to 240° C. A solution of condensation intermediate 3 (662 g) in Dowtherm™ A (900 mL) was added over 10 min, while the temperature was maintained in the range 230-245° C. The mixture was heated for another 1 h at 240° C. and then cooled to room temperature. Petroleum ether (2000 mL) and heptane (2400 mL) were added. An oily residue formed and the solvent was decanted. The collected oil residue was purified by flash column chromatography (eluent: CH$_2$Cl$_2$: EtOAc=10:1 to 1:3) resulting in compound 4 (38 g). Method B; Rt: 5.20 min. m/z: 429.0 (M+H)$^+$ Exact mass: 428.1 Columns: AD-H 50 mm*4.6 mm, 3 um Flow: 4 mL/min; Mobile phase: A: CO$_2$ B: EtOH (0.05% Diethylamine), 5% to 40% B in A; Temperature: 40° C., isomer 4a: Rt: 1.53 min; 4b Rt: 1.73 min.

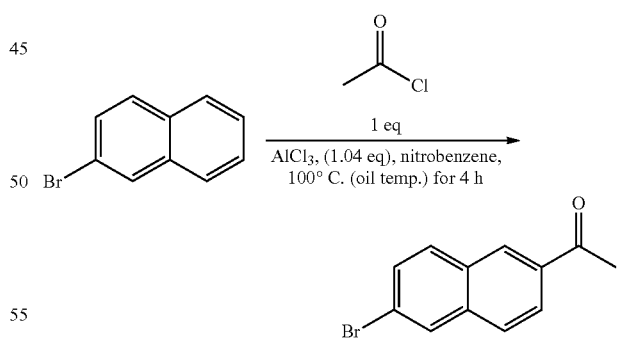

A mixture of 2-bromonaphthalene (950 g, 4589 mmol), acetyl chloride (260 mL, 4589 mmol), nitrobenzene (6000 mL) and aluminum chloride (642.2 g, 4818 mmol) was stirred for 4 hours at 100° C. The mixture was poured onto ice water, the resulting slurry was filtrated and the organic phase separated from the filtrate. The organic phase was washed with water (2000 mL), dried over Na$_2$SO$_4$ and filtrated. The solvent was removed by distillation. The residue was re-crystallized from a solution of hexane:ethyl acetate (10:1) resulting in 1-(6-bromonaphthalen-2-yl)ethanone (480 g, 42% yield).

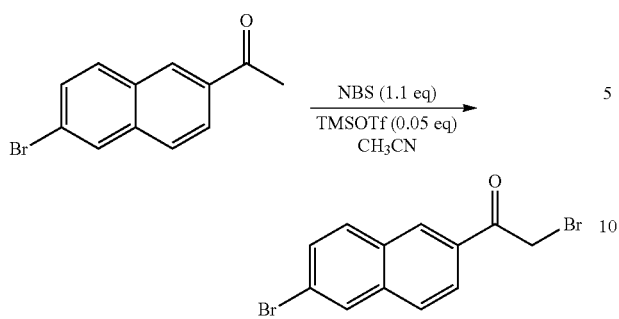

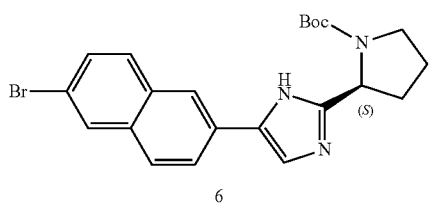

TMSOTf (13.4 g, 60.2 mmol) was added to a stirred solution of 1-(6-bromonaphthalen-2-yl)ethanone (300 g, 1204 mmol) and NBS (235.8 g, 1324 mmol) in CH₃CN (6000 mL). The mixture was stirred for 24 h at 30° C. The reaction mixture was diluted with ether, washed with H₂O, dried over Na₂SO₄, filtered, and concentrated under reduced pressure. The residue of crude 2-bromo-1-(6-bromonaphthalen-2-yl)ethanone (526 g) was used in the next step without further purification.

5 (794 g, 1204 mmol) was dissolved in toluene (6000 mL) and ammonium acetate (1855 g, 24096 mmol) was added to the solution. The mixture was stirred for 12 h at 100° C. The solution was diluted with ethyl acetate (1000 mL), and washed with water (2×500 mL). The inorganic layer was extracted with ethyl acetate (2×500 mL). The combined organic layers were concentrated under vacuum. The residue was triturated in CH₃CN (300 mL) for 0.5 h at 0° C., resulting in compound 6 (140 g, 26% yield based on 1-(6-bromonaphthalen-2-yl)ethanone). Method A; Rt: 1.28 min. m/z: 442.1 (M+H)⁺ Exact mass: 441.1

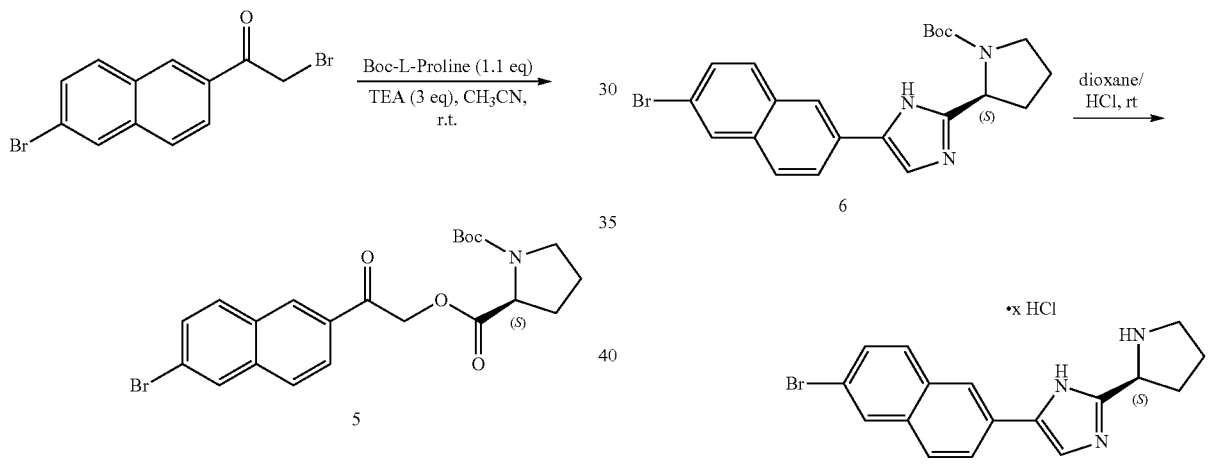

2-Bromo-1-(6-bromonaphthalen-2-yl)ethanone (526.5 g, 1204. mmol) was dissolved in CH₃CN (6000 mL). Boc-L-proline (284 g, 1325 mmol) was added to the solution and the reaction mixture was stirred for 20 min at room temperature. Et₃N (480 mL, 3612 mmol) was added dropwise to the solution. The reaction mixture was stirred for 15 h at room temperature. The solvent was removed under vacuum and crude 5 (794 g) was used in the next step without further purification. Method A1; Rt: 1.68 min. m/z: 484.1 (M+Na)⁺ Exact mass: 461.1

To the solution of compound 6 (75 g, 170 mmol) was added dioxane/HCl (750 mL) at room temperature and the mixture was stirred for 1 hour. The mixture was filtered to obtain compound 6a (73 g).

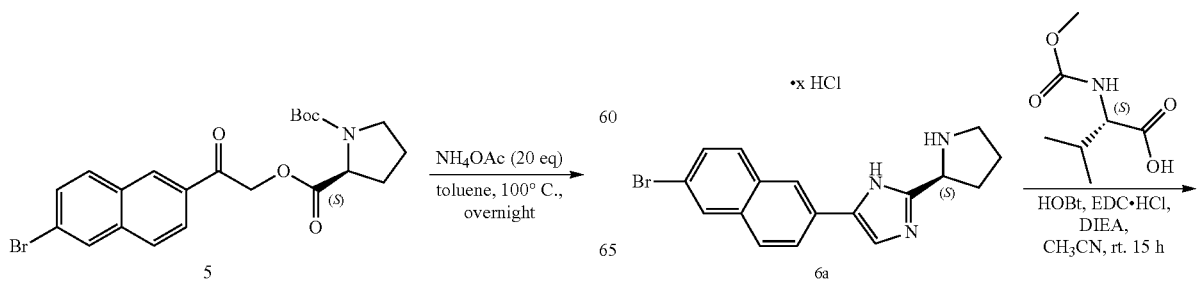

-continued

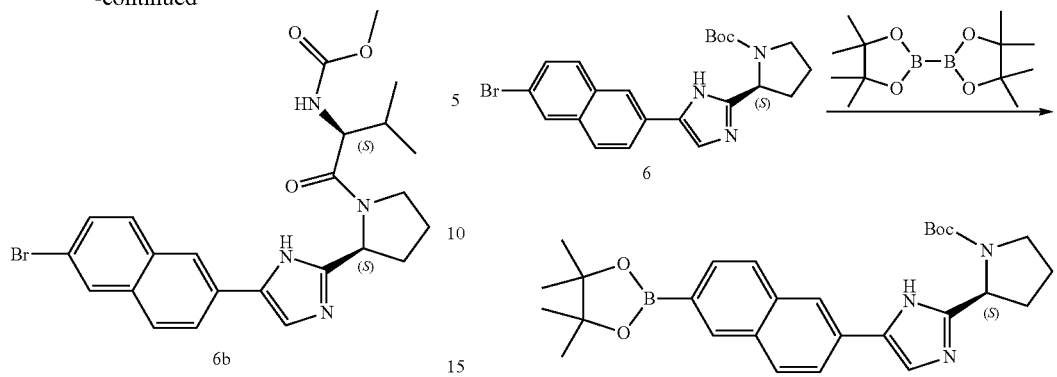

To a solution of (S)-2-(methoxycarbonylamino)-3-methylbutanoic acid (47.2 g, 270 mmol) in CH$_3$CN (1200 mL) were added HOBt (36.4 g, 270 mmol) and EDC.HCl (51.6 g, 270 mmol) at room temperature. The mixture was stirred for 30 minutes at room temperature and 6a (73 g) was added. The solution was then cooled to 0° C., diisopropylethylamine (75 g, 578 mmol) was added and the mixture was stirred at room temperature overnight. The mixture was diluted with CH$_2$Cl$_2$ (1500 mL) and washed with NaOH aqueous (0.5 N, 1000 mL). The organic layer was washed with brine. The combined organic layer was dried and concentrated. The obtained crude product was washed with CH$_3$CN, resulting in compound 6b (80 g, from 6: 94%).

Pd(PPh$_3$)$_4$ (11.6 g, 15.8 mmol) was added to a mixture of compound 6 (140 g, 316.5 mmol), bis(pinacolato)diboron (160.7 g, 633 mmol), KOAc (62 g, 633 mmol) and toluene (4000 mL) under nitrogen. The reaction mixture was stirred for 15 h at 85° C. After cooling, CH$_2$Cl$_2$ was added and mixture was washed with Na$_2$CO$_3$, followed by brine. The water was extracted with CH$_2$Cl$_2$ (3×900 mL). The combined organic layers were dried over Na$_2$SO$_4$, filtered and concentrated under vacuum. The residue was re-crystallized in a mixed solvent of hexane/i-Pr$_2$O (3/2, 2×150 mL) resulting in compound 7 (105 g, 63% yield). Method A3; Rt: 1.35 min. m/z: 490.1 (M+H)$^+$ Exact mass: 489.3

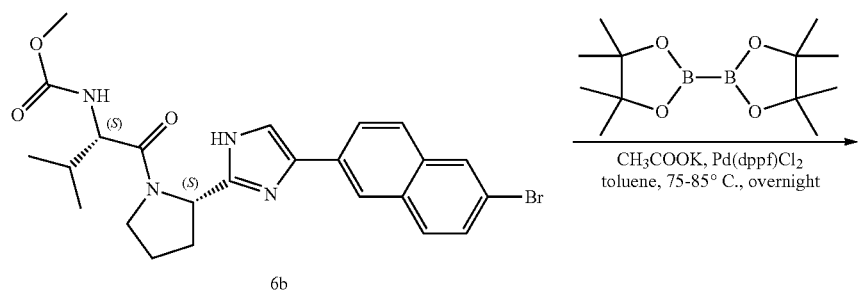

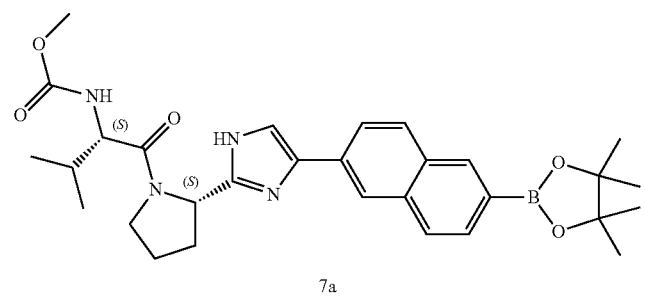

6b (69 g, 138.2 mmol), 4,4,4',4',5,5,5',5'-octamethyl-2,2'-bi(1,3,2-dioxaborolane) (70.2 g, 276.4 mmol) and CH₃COOK (27.1 g, 276.4 mmol) were added to toluene (1500 mL) followed by Pd(dppf)Cl₂ (5 g, 6.9 mmol) under N₂ at room temperature. The reaction mixture was stirred at 80° C. overnight. After cooling, ethyl acetate (1000 mL) was added and the mixture was washed with saturated NaHCO₃ (1500 mL) and brine. The water layer was extracted with ethyl acetate. The organic layer were dried over Na₂SO₄ and after filtration, concentrated in vacuo. The crude product was purified by column chromatography resulting in compound 7a (52 g, 68% yield). Method C; Rt: 4.01 min. m/z: 547.3 (M+H)⁺ Exact mass: 546.3

SFC: Column: (AS)—H 150 mm×4.6 mm; Sum. Flow: 3 mL/min, Mobile phase: A: CO₂ B: EtOH (0.05% Diethylamine); 5 to 40% B in A,: Rt: 3.11 min SFC: Column: OD-H 50 mm×4.6 mm; 3 um. Flow: 4 mL/min, Mobile phase: A: CO₂ B: EtOH (0.05% Diethylamine); 5 to 40% B in A,: Rt: 1.34 min Pd(PPh₃)₄ (17.4 g, 15.1 mmol) was added in one portion to a mixture of compound 7 (37 g, 75.6 mmol) and 2 (32.3 g, 75.6 mmol), Na₂CO₃/H₂O (16 g/300 mL), toluene (600 mL) and ethanol (300 mL) under nitrogen. The mixture was stirred for 10 h at 90° C. The reaction mixture was filtered and washed with methanol (500 mL). The filtrate was concentrated under vacuum. The residue was extracted with CH₂Cl₂ (3×300 mL). The combined organic layers were concentrated to dryness under vacuum. The residue was dissolved in CH₃CN and purified by preparative high-performance chromatography (eluent: CH₃CN/H₂O=40/60 to 65/35, 0.1% CF₃COOH). The desired fraction was collected and the pH of the solution was adjusted to 8 to 9 with saturated NaHCO₃ (aq.) CH₃CN was removed under reduced pressure. The aqueous layer was extracted with CH₂Cl₂ (3×150 mL). The organic layers were combined and dried under Na₂SO₄. The solution was evaporated and the pure product 8 was dried under vacuum (12.7 g, 19% yield). Method C; Rt: 3.91 min. m/z: 710.5 (M+H)⁺ Exact mass: 709.3

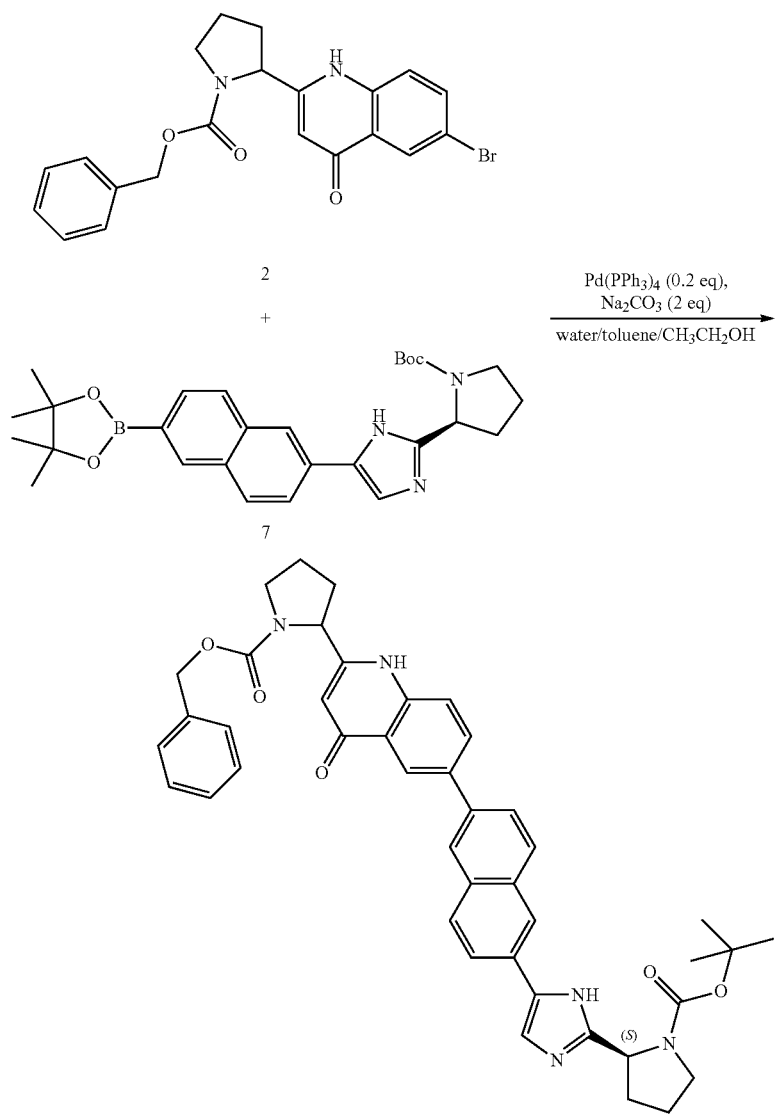

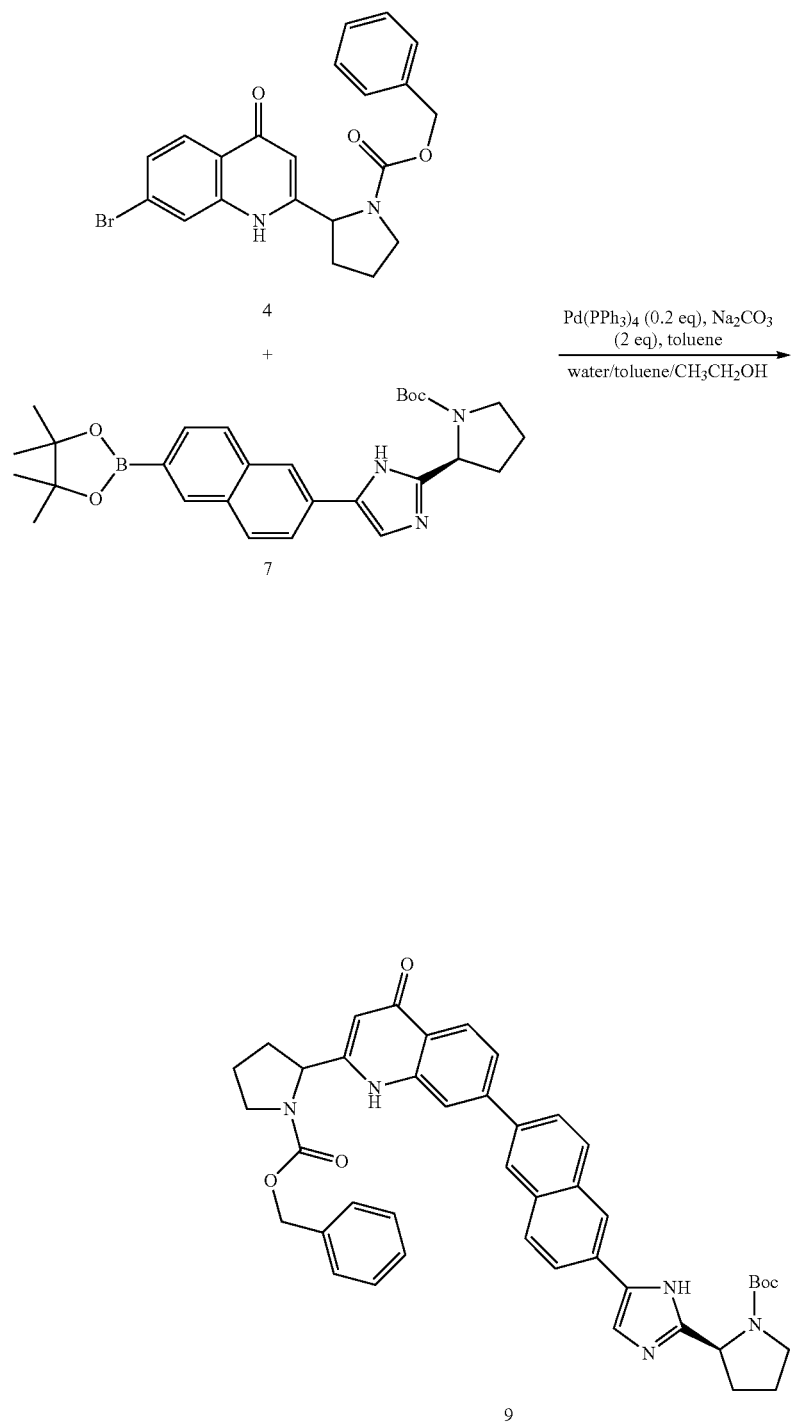

Pd(PPh$_3$)$_4$ (20.5 g, 17.8 mmol) was added in one portion to the mixture of compound 7 (43.5 g, 88.9 mmol) and 4 (38 g, 88.9 mmol), Na$_2$CO$_3$/H$_2$O (18.8 g/300 mL), toluene (650 mL) and ethanol (350 mL) under nitrogen. The mixture was stirred for 10 h at 90° C. The reaction mixture was filtered and washed with methanol (500 mL). The filtrate was concentrated under vacuum. The residue was extracted with CH$_2$Cl$_2$ (2×500 mL). The combined organic layers were concentrated to dryness under vacuum. The residue was triturated in CH$_3$CN to afford product 9 (25 g, 40% yield). Method A1; Rt: 1.22 min. m/z: 710.3 (M+H)$^+$ Exact mass: 709.3

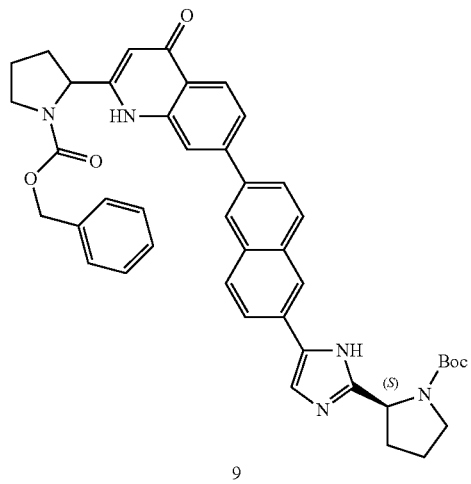

9

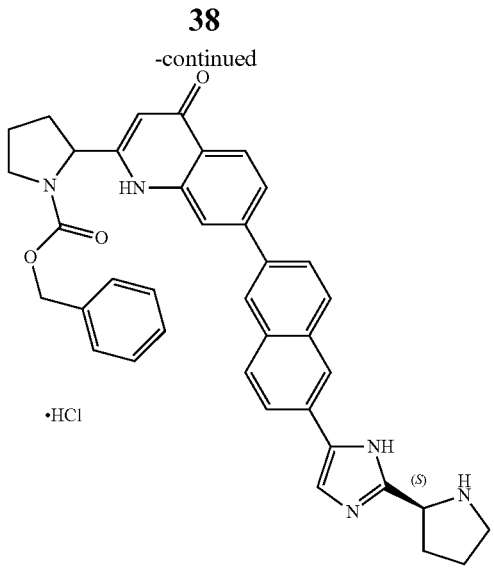

10

4N HCl/dioxane (4.2 mL, 17 mmol) was added to a solution of 9 (6 g, 8.5 mmol) in CH$_2$Cl$_2$ (40 mL) at 0° C. The mixture was allowed to warm to room temperature and was stirred for 10 min. The precipitate was filtered off and washed with tert-butyl methyl ether to obtain compound 10 (5.2 g, 87% yield). Method A; Rt: 1.14 min. m/z: 610.4 (M+H)$^+$ Exact mass: 609.3

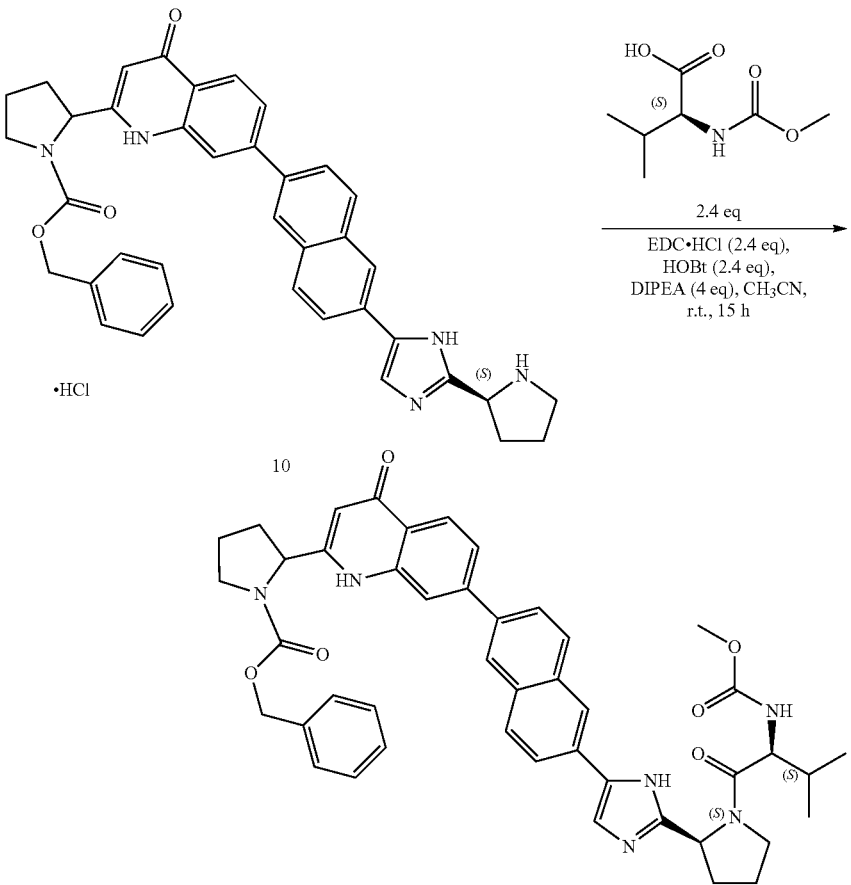

To a solution of compound (S)-2-(methoxycarbonylamino)-3-methylbutanoic acid (3.6 g, 20.4 mmol) in CH₃CN (100 mL) was added EDC.HCl (3.9 g, 20.4 mmol) and HOBT (2.75 g, 20.4 mmol). The mixture was stirred at 20° C. for 1 h. Then 10 (5.2 g, 7.6 mmol) was added. The slurry was cooled to 0° C. and DIPEA (4.4 g, 30.4 mmol) was added. The mixture was stirred at room temperature for 15 h. The mixture was concentrated and the residue was diluted with 150 mL CH₂Cl₂ and 75 mL of 0.5 N NaOH (aq). The organic layer was separated and washed with brine (3×75 mL), dried and concentrated to obtain the crude product. The crude product 11 was used in the next step without further purification (4.9 g, 87% yield). Method A; Rt: 1.19 min. m/z: 767.3 (M+H)⁺ Exact mass: 766.4

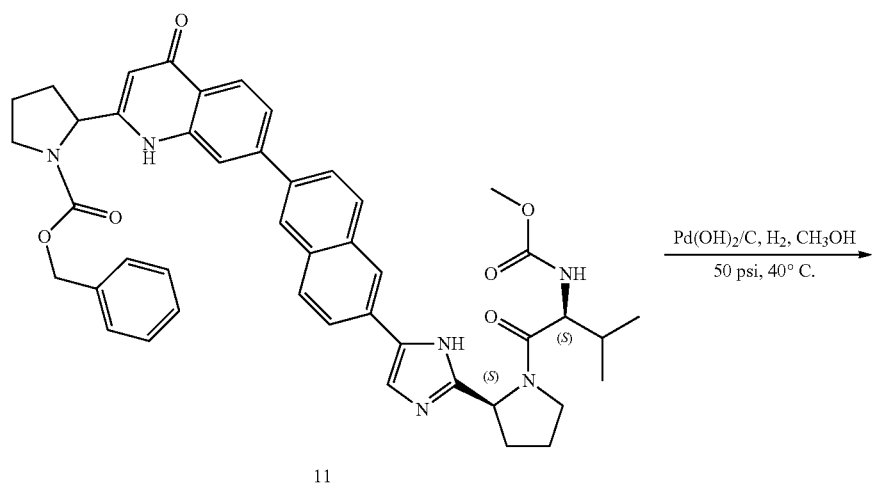

11

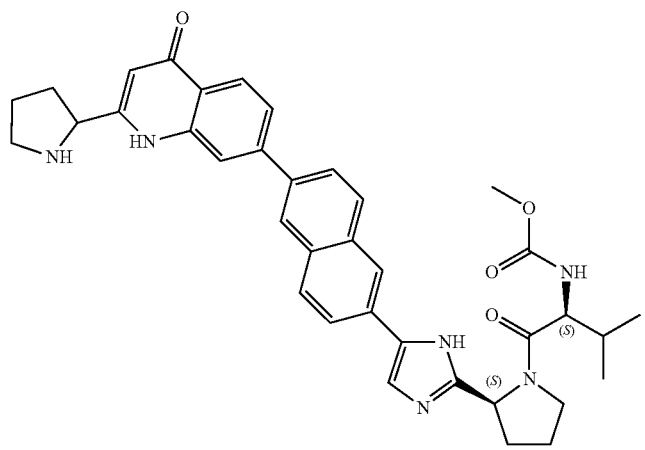

12

Pd(OH)₂/C (20%, 3 g, dry) was added to a solution of 11 (4.9 g, 6.4 mmol) in methanol (40 mL). The mixture was hydrogenated under H₂ (345 kPa) at 40° C. After 18 hours, the mixture was filtered over diatomaceous earth and concentrated. The crude of compound 12 was used in the next step without further purification (4.0 g, 75% yield). Method A; Rt: 1.04 min. m/z: 633.3 (M+H)⁺ Exact mass: 632.3

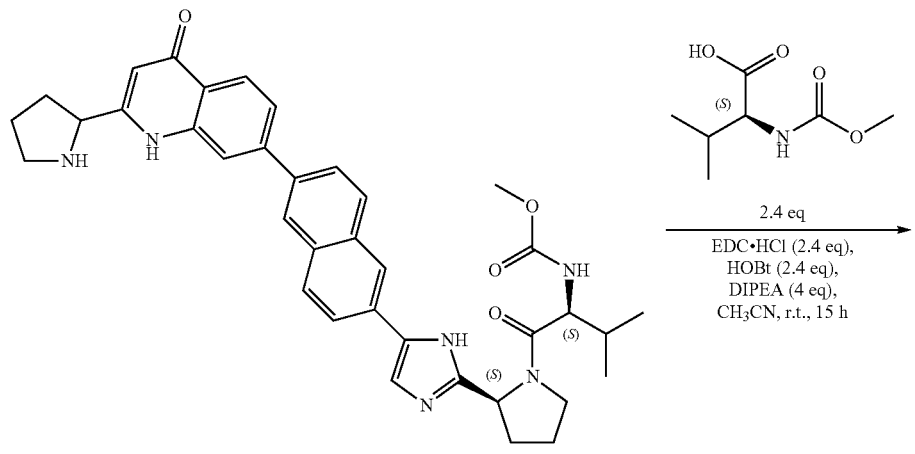

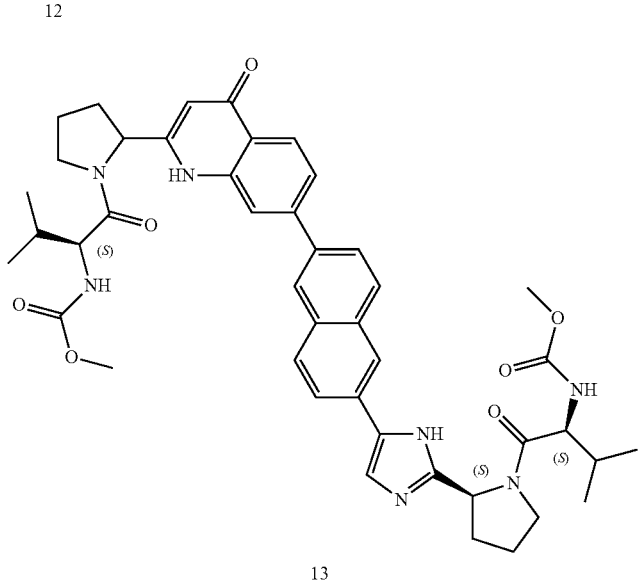

To a solution of compound (S)-2-(methoxycarbonylamino)-3-methylbutanoic acid (2.6 g, 15.1 mmol) in CH$_3$CN (40 mL) was added EDC.HCl (2.8 g, 15.1 mmol) and HOBT (2.0 g, 15.1 mmol). The mixture was stirred at 20° C. for 1 h. Then 12 (4.0 g, 6.3 mmol) was added. The slurry was cooled to 0° C. and DIPEA (3.2 g, 25.2 mmol) was added. The mixture was stirred at room temperature for 15 h. The mixture was concentrated and diluted with CH$_2$Cl$_2$ (120 mL) and aqueous 0.5 N NaOH (50 mL). The organic layer was separated and washed with brine (3×50 mL), dried and concentrated to obtain the crude product. The crude product was purified by preparative high-performance chromatography (eluent: CH$_3$CN/H$_2$O=30/70 to 60/40, 0.1% CF$_3$COOH). The desired fraction was collected and the pH value of the solution was adjusted to about 6 with 0.5 N citric acid (aq.) CH$_3$CN was removed under reduced pressure. The aqueous layer was extracted with CH$_2$Cl$_2$ (3×150 mL). The organic layers were combined and dried under Na$_2$SO$_4$. The solution was evaporated and the compound 13 was dried under vacuum (2 g, 40% yield). 1 g of diastereomeric mixture 13 was separated by SFC separation. The two desired fractions were collected and the solvent was evaporated under reduced pressure. The pure product was dried under vacuum. 335 mg 13a and 310 mg 13b were obtained. SFC: Column: OD-3 150 mm*4.6 mm; 3 um; Flow: 2.5 mL/min Mobile phase: 40% EtOH (0.05% diethylamine) in CO$_2$ 13a: Rt: 4.9 Min; 13b: Rt: 7.8 Min; Isomer 13b: Method C; Rt: 3.63 min. m/z: 790.5 (M+H)$^+$ Exact mass: 789.4; Isomer 13a: Method C; Rt: 3.69 min. m/z: 790.4 (M+H)$^+$ Exact mass: 789.4

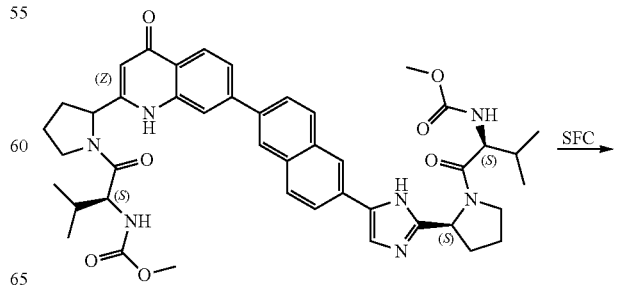

13

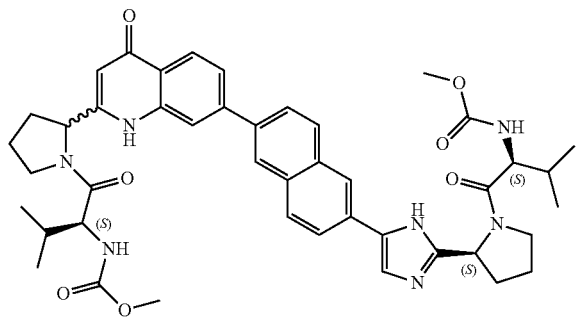
13a
+
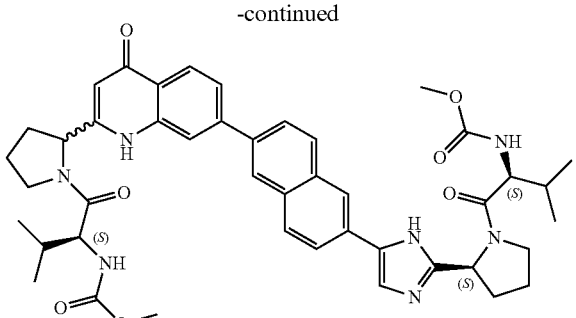
13b
13b: ¹H NMR (400 MHz, DMSO-d₆; main isomer described) δ ppm 0.83-0.95 (m, 12H), 1.87-2.10 (m, 6 H), 2.10-2.24 (m, 2 H), 2.24-2.38 (m, 2 H), 3.55 (s, 6 H), 3.78-3.93 (m, 4 H), 4.09 (t, J=8.3 Hz, 1 H), 4.15 (t, J=8.0 Hz, 1 H), 4.94 (dd, J=8.0, 3.3 Hz, 1 H), 5.06-5.18 (m, 1 H), 5.86 (s, 1 H), 7.29-7.41 (m, 2 H), 7.66 (s, 1 H), 7.75 (d, J=8.5 Hz, 1 H), 7.80-8.10 (m, 5 H), 8.14 (d, J=8.5 Hz, 1 H), 8.27 (s, 1 H), 8.24 (s, 1 H), 11.73 (br. s, 1 H), 11.89 (s, 1 H)
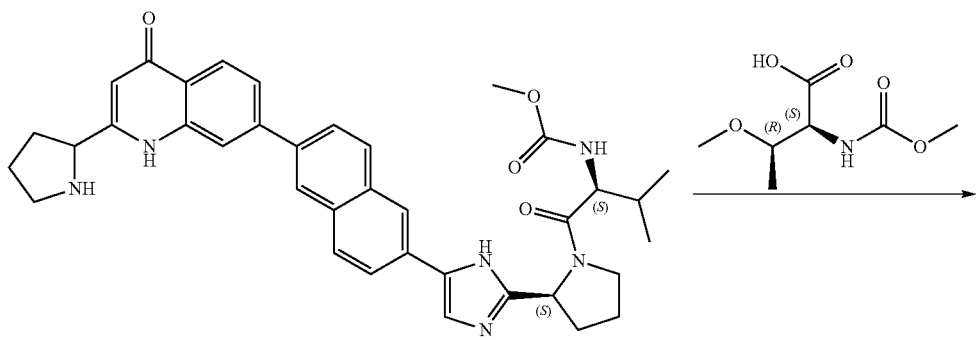
12
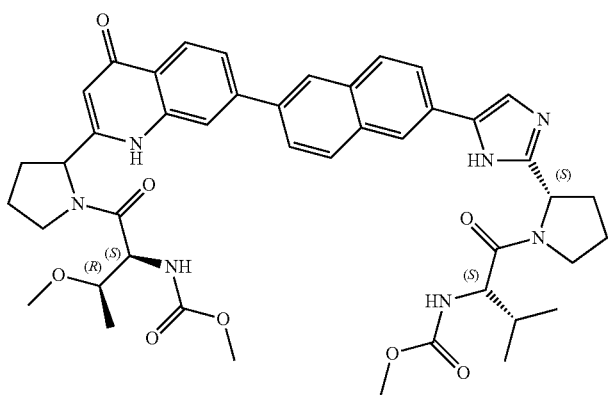
13-A1

To (2S,3R)-3-methoxy-2-(methoxycarbonylamino)butanoic acid (63.5 mg, 0.332 mmol) dissolved in dichloromethane (100 mL) in a 250 mL round-bottomed flask was added triethylamine (0.13 mL, 0.95 mmol) followed by COMU (142 mg, 0.33 mmol). The mixture was stirred at room temperature. After 10 minutes, compound 12 (200 mg, 0.32 mmol) was added and the reaction mixture was stirred at room temperature for 1 hour. 5-6N HCl in iPrOH (10 mL) was added to the reaction mixture and subsequently the mixture was washed with saturated aqueous $Na_2CO_3$— solution (2×200 mL). The organic layer was dried on $MgSO_4$ and after filtration, the filtrate was evaporated to dryness to afford a brown powder. The obtained powder was purified by silica gel chromatography by elution with 0 to 8% MeOH (7N $NH_3$) in EtOAc). After collection of the relevant fractions and evaporation of the volatiles, compound 13-A1 was obtained as a yellow-white powder (105 mg, 0.130 mmol, 41%) Method E; Rt: 5.01 min. m/z: 806.3 $(M+H)^+$ Exact mass: 805.4;

13-A2

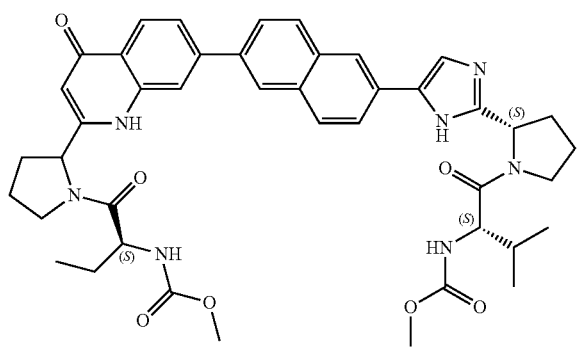

Compound 13-A2 was synthesized similarly as described for 13-A1 using (S)-2-(methoxycarbonylamino)butanoic acid instead of (2S,3R)-3-methoxy-2-(methoxycarbonylamino)butanoic acid. Method E; Rt: 5.0 (two peaks) min. m/z: 776.4 $(M+H)^+$ Exact mass: 775.4;

13-A3

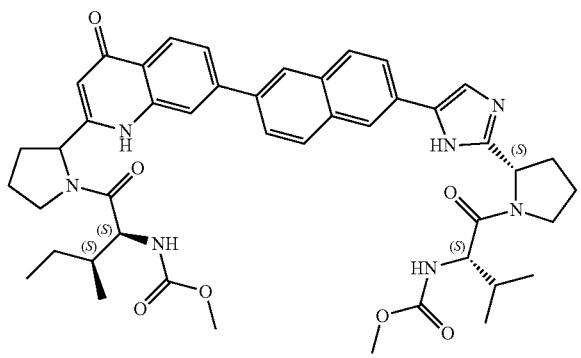

Compound 13-A3 was synthesized similarly as described for 13-A1 using (2S,3S)-2-(methoxycarbonylamino)-3-methylpentanoic acid instead of (2S,3R)-3-methoxy-2-(methoxycarbonylamino)butanoic acid. Method E; Rt: 5.45 and 5.61 min. m/z: 804.4 $(M+H)^+$ Exact mass: 803.4

13-A4

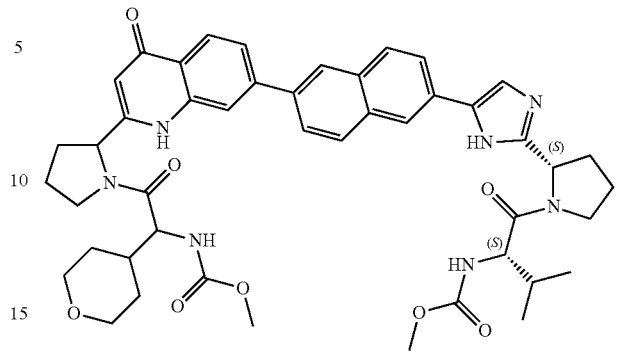

Compound 13-A4 was synthesized similarly as described for 13-A1 using 2-(methoxy-carbonylamino)-2-(tetrahydro-2H-pyran-4-yl)acetic acid instead of (2S,3R)-3-methoxy-2-(methoxycarbonylamino)butanoic acid. Method E; Rt: 4.94 min. m/z: 832.4 $(M+H)^+$ Exact mass: 831.4

13-A5

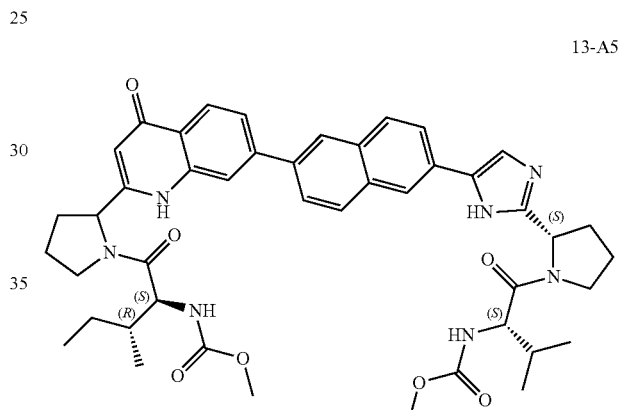

Compound 13-A5 was synthesized similarly as described for 13-A1 using (2S,3R)-2-(methoxycarbonylamino)-3-methylpentanoic acid instead of (2S,3R)-3-methoxy-2-(methoxycarbonylamino)butanoic acid. Method E; Rt: 5.54 and 5.64 min. m/z: 804.4 $(M+H)^+$ Exact mass: 803.4

13-A6

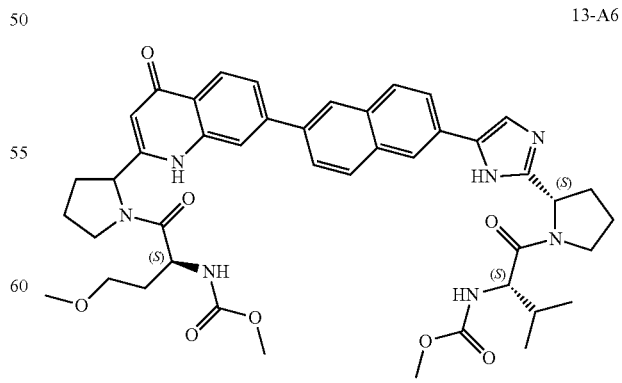

Compound 13-A6 was synthesized similarly as described for 13-A1 using (S)-4-methoxy-2-(methoxycarbonylamino)butanoic acid instead of (2S,3R)-3-methoxy-2-(methoxycarbonylamino)butanoic acid. Method E; Rt: 5.03 min. m/z: 806.4 (M+H)+ Exact mass: 805.4

Method E; Rt: 4.88 min. m/z: 792.4 (M+H)+ Exact mass: 791.4

13-A7

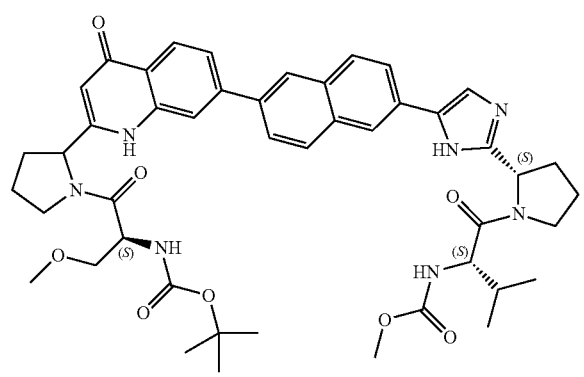

Compound 13-A7 was synthesized similarly as described for 13-A1 using (S)-2-(tert-butoxycarbonylamino)-3-methoxypropanoic dicyclohexyl amine salt instead of (2S,3R)-3-methoxy-2-(methoxycarbonylamino)butanoic acid. Method E; Rt: 5.70 min. m/z: 834.4 (M+H)+ Exact mass: 833.4

13-A8

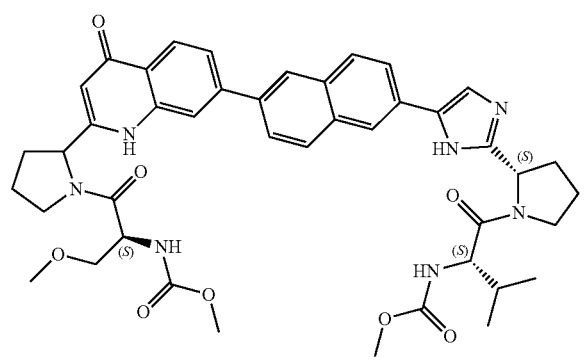

Compound 13-A8 was synthesized starting from compound 13-A7.

13-A7 (135 mg, 0.162 mmol) was stirred in MeOH (9 mL) and 6 M HCl in iPrOH (2.9 mL) was added, the mixture was stirred at room temperature for 3 hours and the volatiles were removed. The obtained powder (130 mg) was stirred in acetonitrile (10 mL) and treated with methylchloroformate and N-Methylimidazole, until the starting product was consumed. The volatiles were removed, dissolved in MeOH (5 mL), treated with 6M HCl in iPrOH (5 mL) and the mixture was refluxed for 2 hours, the volatiles were removed and the compound was purified by preparative HPLC (RP Vydac Denali C18-10 μm, 250 g, 5 cm) Mobile phase (0.25% $NH_4HCO_3$ solution in water, $CH_3CN$)), the desired fractions were collected, evaporated, dissolved in MeOH and evaporated again. After drying in vacuo, compound 13-A8 (32 mg) was obtained.

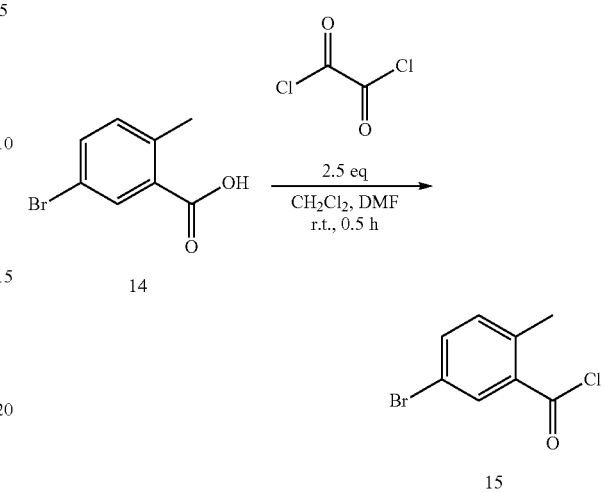

Oxalyl chloride (50 mL, 581.5 mmol) was added dropwise at room temperature to a solution of 14 (50 g, 232.5 mmol) in $CH_2Cl_2$ (750 mL) and DMF (1 mL, 11.6 mmol. The reaction mixture was stirred for 0.5 h at room temperature. The reaction mixture was concentrated under vacuum and the residue was used without further purification. Total 65 g of the crude 15 was obtained.

To a solution of 15 (65 g, 232.5 mmol) in THF (750 mL) was added diethylamine (18.7 g, 255.7 mmol) and 1 N NaOH in water (465 mL, 465 mmol). The mixture was stirred for 1 h at room temperature. The reaction mixture was extracted with ethyl acetate (3×10 mL). The organic layers were combined, dried and concentrated under vacuum. The residue was purified by column chromatography (hexane:ethyl acetate=10:1) to give the product 16 (36 g, 57% yield, 2 steps). Method A3; Rt: 1.39 min. m/z: 269.9 (M+H)+ Exact mass: 269.0

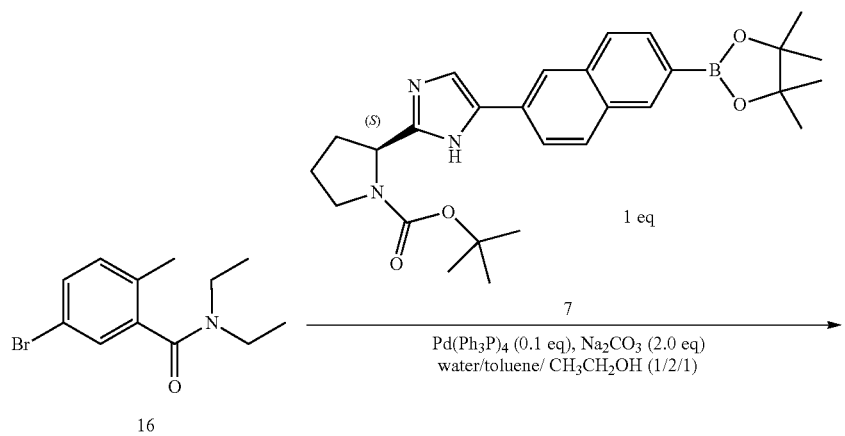

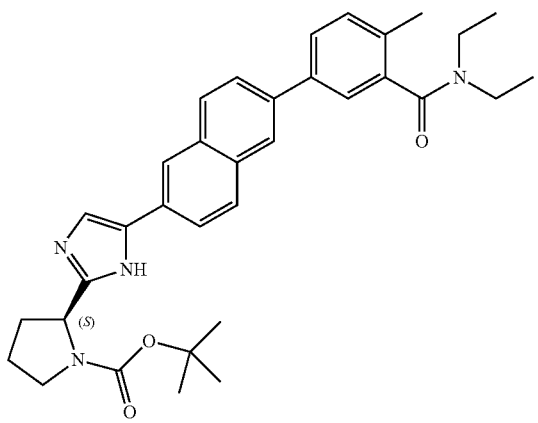

Pd(PPh₃)₄ (4.3 g, 3.7 mmol) was added in one portion to a mixture of 7 (18.1 g, 37 mmol) and 16 (10 g, 37 mmol), Na₂CO₃ (8 g, 74 mmol), water (160 mL), toluene (320 mL) and ethanol (160 mL) under nitrogen. The mixture was stirred for 10 h at 90° C. The reaction mixture was extracted by CH₂Cl₂ (twice 300 mL). The combined organic layers were concentrated under vacuum. The residue was dissolved in ethyl acetate (100 mL) and then petroleum ether (200 mL) was added to the mixture. The clear upper layer solution was decanted and the black oil residue was removed. Additional petroleum ether (800 mL) was added to the resulting solution. The resulting solid was collected by filtration and then dried to afford product 17 (14.7 g, 72% yield). Method A3; Rt: 1.28 min. m/z: 553.2 (M+H)⁺ Exact mass: 552.3

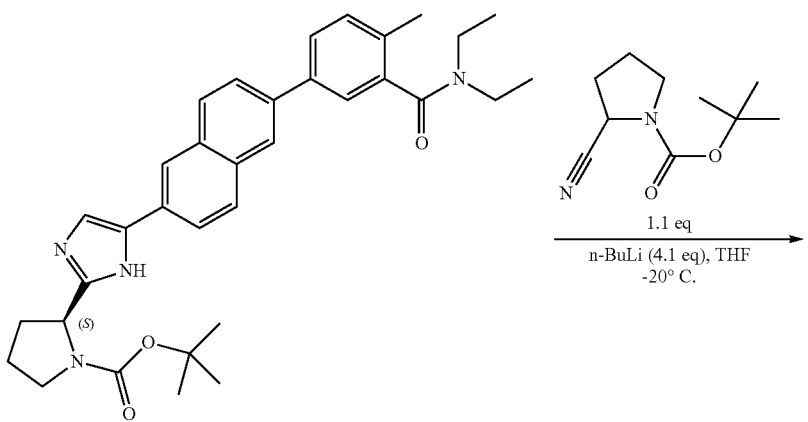

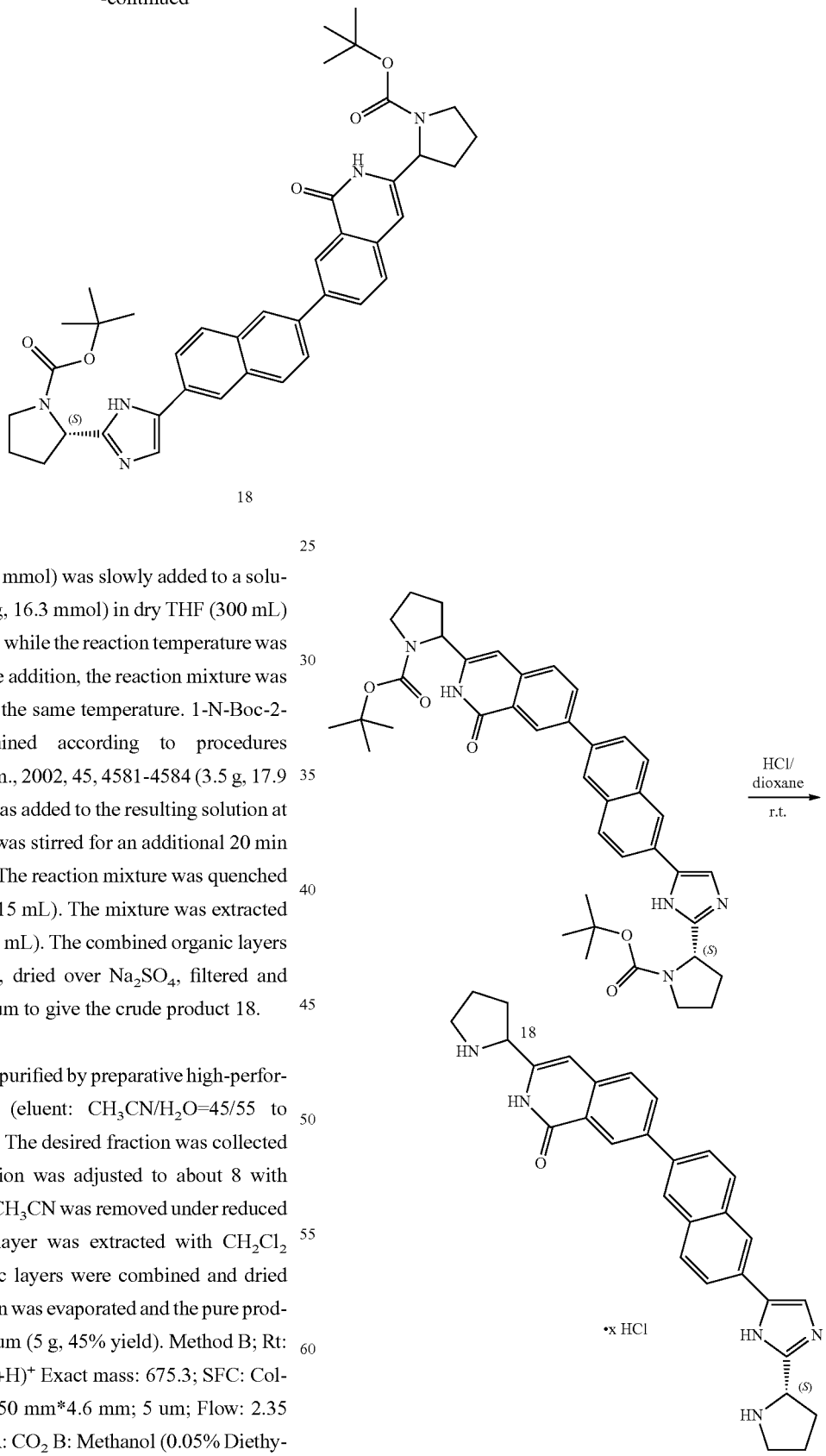

n-BuLi (26.7 mL, 71.6 mmol) was slowly added to a solution of Compound 17 (9 g, 16.3 mmol) in dry THF (300 mL) under nitrogen at −20° C., while the reaction temperature was kept below 0° C. After the addition, the reaction mixture was stirred for another 1 h at the same temperature. 1-N-Boc-2-cyano-pyrrolidine (obtained according to procedures described in J. Med. Chem., 2002, 45, 4581-4584 (3.5 g, 17.9 mmol) in THF (10 mL) was added to the resulting solution at −50° C. and the mixture was stirred for an additional 20 min at the same temperature. The reaction mixture was quenched by slowly adding water (15 mL). The mixture was extracted with ethyl acetate (3×150 mL). The combined organic layers were washed with brine, dried over $Na_2SO_4$, filtered and concentrated under vacuum to give the crude product 18.

The crude product was purified by preparative high-performance chromatography (eluent: $CH_3CN/H_2O$=45/55 to 60/40, 0.1% $CF_3COOH$). The desired fraction was collected and the pH of the solution was adjusted to about 8 with saturated $NaHCO_3$ (aq.) $CH_3CN$ was removed under reduced pressure. The aqueous layer was extracted with $CH_2Cl_2$ (3×150 mL). The organic layers were combined and dried over $Na_2SO_4$. The solution was evaporated and the pure product was dried under vacuum (5 g, 45% yield). Method B; Rt: 5.67 min. m/z: 676.3 (M+H)⁺ Exact mass: 675.3; SFC: Columns: ChiralpakOD-H 250 mm*4.6 mm; 5 um; Flow: 2.35 mL/min; Mobile phase: A: $CO_2$ B: Methanol (0.05% Diethylamine; 40% B in A. Isomer 18a: Rt: 5.51 min isomer 18b: Rt: 6.71 min Compound 18 (1.8 g, 2.7 mmol) was dissolved in CH$_2$Cl$_2$ (10 mL). and 4 N HCl in 1,4-dioxane (2 mL, 8.1 mmol) was added dropwise at 0-5° C. The reaction mixture was stirred at room temperature for 1 hour, filtered and the solid was washed with t-butyl methyl ether (20 mL) resulting in product 19 (1.4 g). Method D; Rt: 1.52 min. m/z: 476.3 (M+H)$^+$ Exact mass: 475.2 was adjusted to about 8 with saturated NaHCO$_3$ (aq.) CH$_3$CN was removed under reduced pressure. The aqueous layer was extracted with CH$_2$Cl$_2$ (3×200 mL). The organic layers were combined and dried under Na$_2$SO$_4$. The solution was evaporated resulting in compound 20 (0.893 g). Method B; Rt: 5.14 min. m/z: 790.4 (M+H)$^+$ Exact mass: 789.4; SFC: Column: Chiralpak AS-H 250 mm*4.6 mm; 5 um; Flow: 2.35 mL/min Mobile phase: 40% MeOH (0.05% diethylamine) in CO$_2$ 20a: Rt: 4.5 Min; 20b: Rt: 8.0 Min

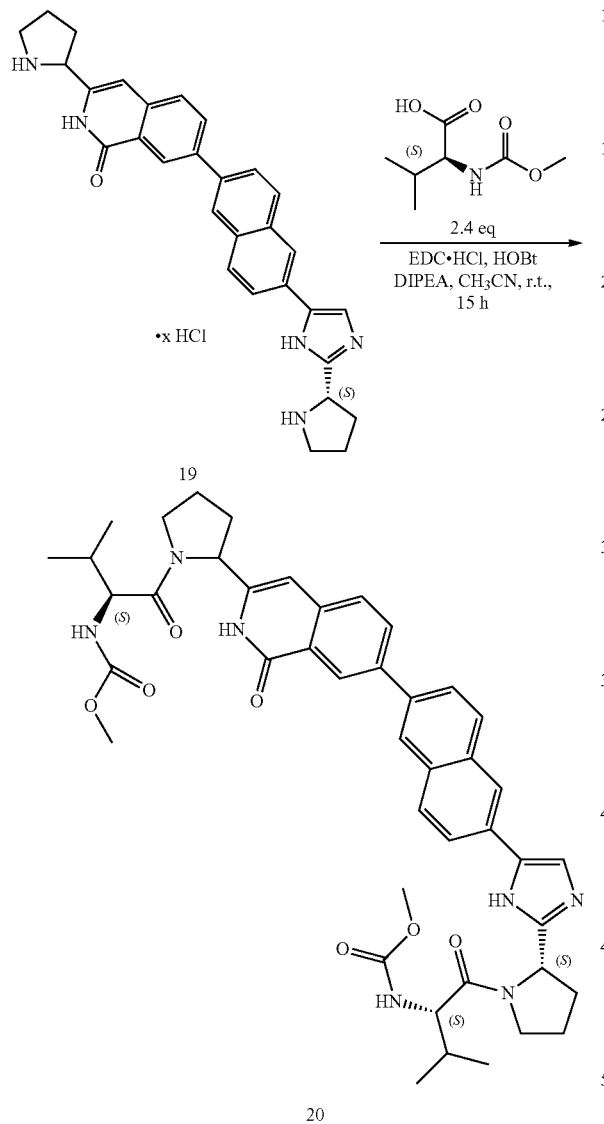

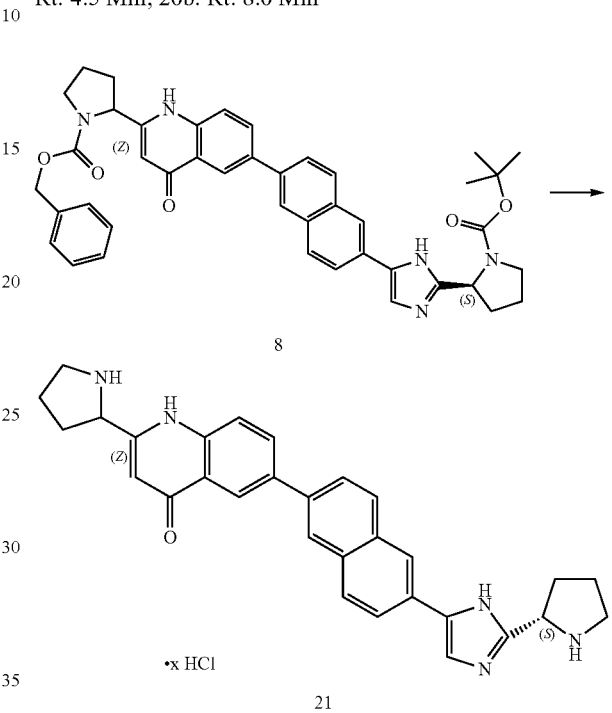

Compound 8 (1500 mg, 2.11 mmol, 1.00 equiv.) was dissolved in 5-6 N HCl in isopropanol (150 mL, 900 mmol, 426 equiv.) in a 250 mL round-bottomed flask and the reaction mixture was stirred for 20 hours at 100° C. under nitrogen atmosphere and allowed to cool to room temperature. To the slurry was added tBuOMe (100 mL). The solids were filtered and washed with tBuOMe (2×50 mL) and immediately dried under vacuum to afford 1.23 g of compound 21 as a yellow powder which was used as such in the next steps.

To a solution of compound (S)-2-(methoxycarbonylamino)-3-methylbutanoic acid (1.01 g, 5.8 mmol) in CH$_3$CN (20 mL) were added HOBT (0.8 g, 5.8 mmol) and EDC.HCl (1.08 g, 5.8 mmol). The mixture was stirred at 20° C. for 1 h. Then compound 19 (1.14 g) was added. The resulting slurry was cooled to 0° C. and DIPEA (1.3 g, 8.4 mmol) was added. The mixture was stirred at 20° C. for 15 h. The mixture was concentrated and diluted with 30 mL of CH$_2$Cl$_2$ and 15 mL of 0.5 N NaOH (aq.). The organic layer was separated and washed with brine (3×15 mL). The organic layer was dried and concentrated to give the crude product. The crude product was purified by preparative high-performance chromatography (eluent: CH$_3$CN/H$_2$O=35/65 to 70/30, 0.1% CF$_3$COOH). The desired fraction was collected and the pH of the solution

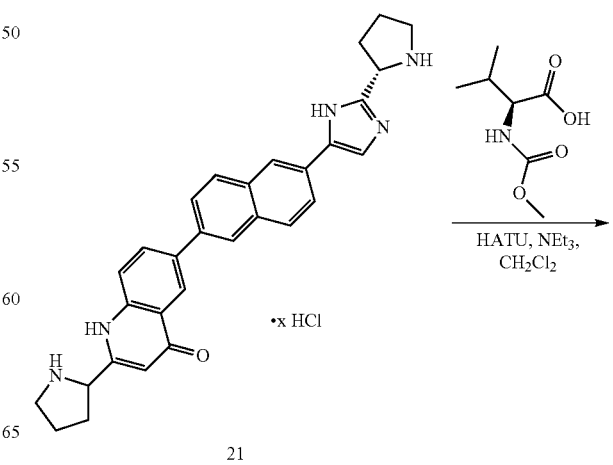

-continued

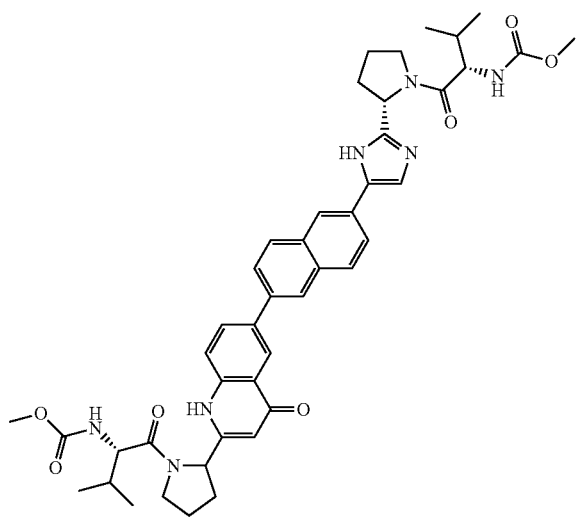

22

To (S)-2-(methoxycarbonylamino)-3-methylbutanoic acid (314 mg, 1.80 mmol) in dichloromethane (150 mL) in a 500 mL round-bottomed flask, was added triethylamine (0.713 mL, 5.13 mmol), followed by 2-(3H-[1,2,3]triazolo[4,5-b]pyridin-3-yl)-1,1,3,3-tetramethylisouronium hexafluorophosphate(V) (682 mg, 1.80 mmol) The mixture was sonicated for 10 minutes. Then, 21 (500 mg, 0.86 mmol) was added and the reaction mixture was stirred overnight at room temperature. To the reaction mixture was added HCl in iPrOH (5-6 N, 10 mL) and the resulting solution was successively washed with a saturated aqueous $Na_2CO_3$— solution (2×200 mL) and brine (100 mL). After drying on magnesium sulphate and filtration, the filtrate was evaporated to dryness to afford a white powder. The powder was purified using column chromatography ($NH_3$ (7N in MeOH)/$CH_2Cl_2$ 0-6.5%) to afford compound 22 as a white powder (diastereomeric mixture, 636 mg; 93%). Part of the diastereomeric mixture (586 mg) was recrystallized from methanol/acetonitrile/DMSO 5/2/2 (9 mL). The solids were filtered, washed with methanol (2×2 mL) and dried in a vacuum oven at 40° C. over weekend to afford isomer 22b (122 mg, 92% de) SFC: Column: (AS) 500 mm×4.6 mm; Flow: 3 mL/min; Mobile phase: 35% MeOH (containing 0.2% $iPrNH_2$) hold 15 min; Temperature: 50° C.; Rt (6.38 min) UV: 4.0% isomer 22a; UV: 96.0% isomer 22b. LC-MS (22b) Method E; Rt: 4.81 min. m/z: 790.3 $(M+H)^+$ Exact mass: 789.4;

The filtrate was cooled to 4° C. over weekend and the resulting precipitate was filtered off, washed with methanol and dried in vacuum oven at 40° C. overnight to afford isomer 22a (164 mg, 92% de) as a white powder. SFC: Column: (OD)-H 500 mm×4.6 mm; Flow: 3 mL/min; Mobile phase: 10-40% MeOH (containing 0.2% $iPrNH_2$) @ 1.6% rate/min, 40-50% MeOH (containing 0.2% $iPrNH_2$) @ 5% rate and hold 4.00 min; Temperature: 50° C.; Rt (21.74 min) UV: 95.9%, 22a; Rt (22.72 min) UV: 4.1%, 22b. LC-MS (22a): Method E; Rt: 5.04 min. m/z: 790.4 $(M+H)^+$ Exact mass: 789.4.

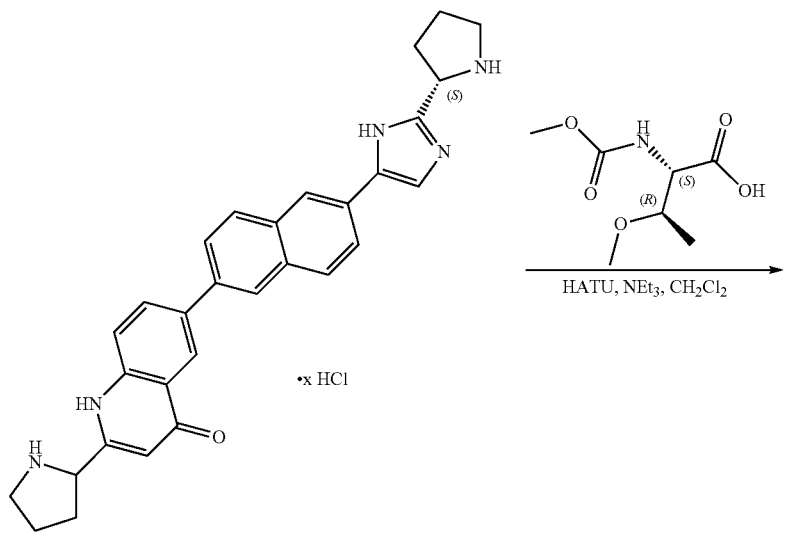

21

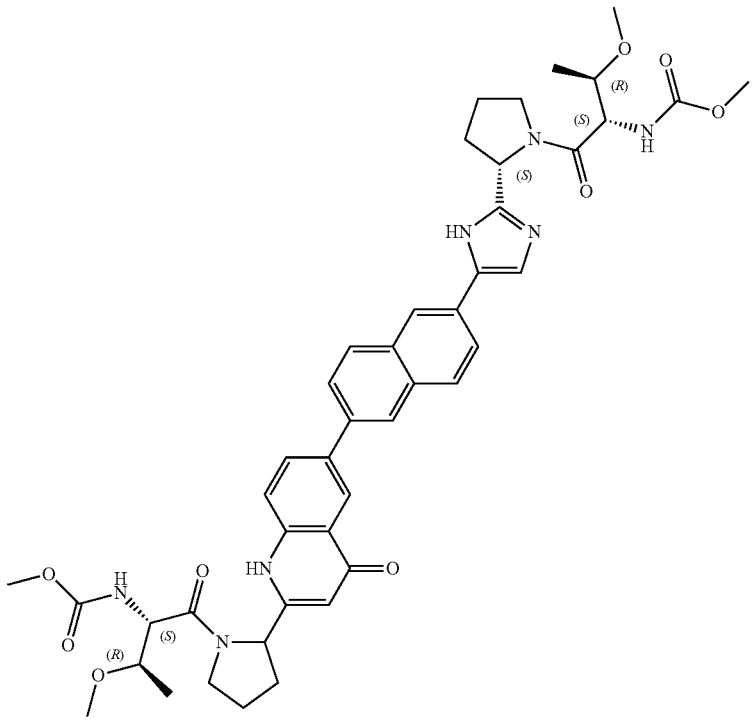

23

To (2S,3R)-3-methoxy-2-(methoxycarbonylamino)butanoic acid (251 mg, 1.31 mmol) dissolved in dichloromethane (150 mL) in a 250 mL round-bottomed flask, was added triethylamine (0.694 mL, 4.99 mmol) followed by 2-(3H-[1,2,3]triazolo[4,5-b]pyridin-3-yl)-1,1,3,3-tetramethylisouronium hexafluorophosphate(V) (498 mg, 1.31 mmol) The mixture was stirred at room temperature for 10 minutes. Compound 21 (365 mg, 0.624 mmol) was added and the reaction mixture was stirred overnight at room temperature. To the reaction mixture was then added HCl in iPrOH (5-6 N, 10 mL) and the resulting solution was successively washed with saturated aqueous $Na_2CO_3$-solution (2×200 mL) and brine (100 mL). The organic layer was dried on magnesium sulphate, filtered and the filtrate was concentrated in vacuo to afford a brown powder. The powder was purified using column chromatography ($NH_3$ (7N in MeOH)/DCM 0-8%) to afford compound 23 (390 mg; 75%) as a white powder ( ) Method D; Rt: 4.40 and 4.52 min. m/z: 822.3. (M+H)$^+$ Exact mass: 821.4;

340 mg of the diastereomeric mixture was recrystallized from methanol (8 mL). The solids were filtered and washed with methanol (2×2 mL) and dried in vacuum oven at 40° C. overnight to afford compound 23b (73 mg, 14%, 93% de) as a white powder. SFC: Column: (OD)-H 250 mm×4.6 mm; Flow: 3.5 mL/min; Mobile phase: 40% MeOH 10.00 min; Temperature: 30° C., Rt (3.58 min, 23a) UV: 3.4%; Rt (4.49 min, 23b) UV: 96.6% Method D; Rt: 4.39 min. m/z: 822.3 (M+H)$^+$ Exact mass: 821.4;

The filtrate was purified by Preparative SFC on Chiralpak Diacel OD 20×250 mm. mobile phase ($CO_2$, methanol with 0.2% i$PrNH_2$). The desired fractions were collected, evaporated, dissolved in methanol and evaporated again, yielding compound 23a (114 mg) as a white powder (22%, 100% de) SFC: Column: (OD)-H 500 mm×4.6 mm; Flow: 3 mL/min; Mobile phase: 40% MeOH (containing 0.2% i$PrNH_2$) hold 19.50 min, 40-50% MeOH (containing 0.2% i$PrNH_2$) hold 4.10 min; Temperature: 50° C.; Rt (6.5 min, 23a) UV: 100.00%; Rt (7.5 min, 23b) UV: 0.00%. LC-MS: Method E; Rt: 4.44 min. m/z: 822.5 (M+H)$^+$ Exact mass: 821.4; and compound 23b (41 mg) as a white powder (7%, 94% de). SFC: Column: (OD)-H 500 mm×4.6 mm; Flow: 3 mL/min; Mobile phase: 40% MeOH (containing 0.2% i$PrNH_2$) hold 19.50 min, 40-50% MeOH (containing 0.2% i$PrNH_2$) hold 4.10 min; Temperature: 50° C.; Rt (6.5 min, 23a) UV: 2.99%; Rt (7.5 min, 23b) UV: 97.01%

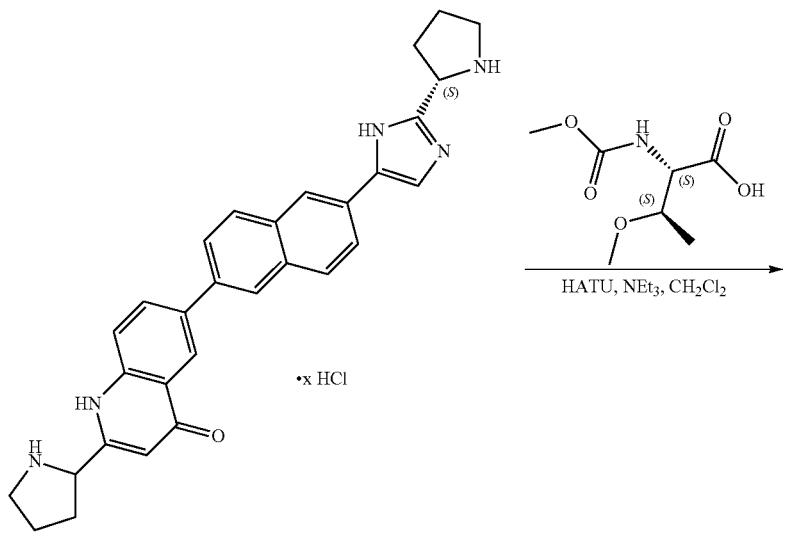

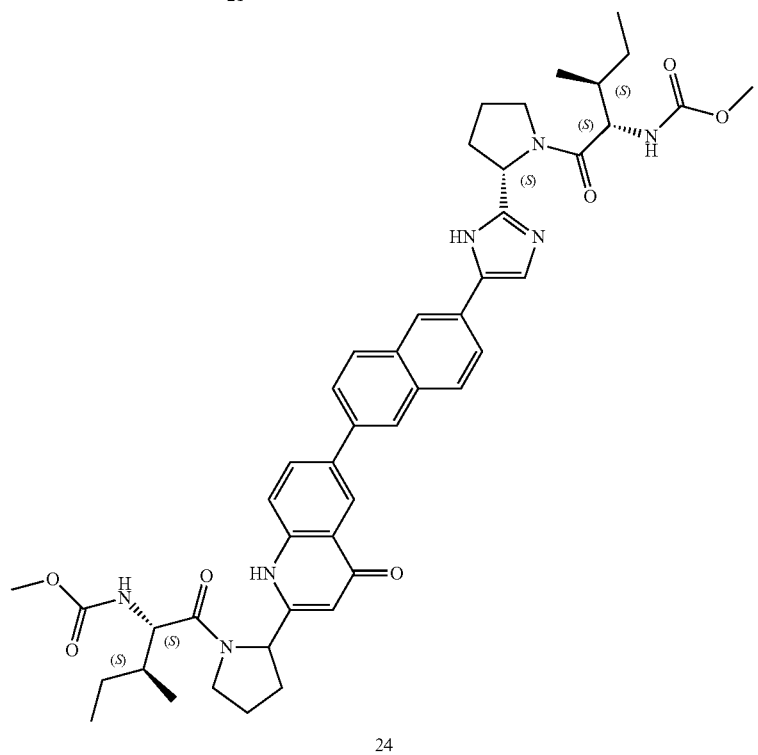

To (2S,3S)-2-(methoxycarbonylamino)-3-methylpentanoic acid (248 mg, 1.31 mmol) dissolved in dichloromethane (150 mL) in a 250 mL round-bottomed flask was added triethylamine (0.694 mL, 4.99 mmol,) followed by 2-(3H-[1,2,3]triazolo[4,5-b]pyridin-3-yl)-1,1,3,3-tetramethylisouronium hexafluorophosphate(V) (498 mg, 1.31 mmol). The mixture was stirred at room temperature for 10 minutes. Compound 21 (365 mg, 0.624 mmol) was added and the reaction mixture was stirred overnight at room temperature. To the reaction mixture was added HCl in iPrOH (5-6 N, 10 mL) and the resulting solution was washed with saturated aqueous $Na_2CO_3$— solution (2×200 mL) and dried on magnesium sulphate. After filtration, the solvent was evaporated in vacuo to afford a brown powder. The powder was purified using column chromatography ($NH_3$ (7N in MeOH)/DCM 0-6.5%) to afford the diastereomeric mixture 24 (395 mg) as a white powder. LC-MS: Method E; Rt: 5.5 and 5.7 min. m/z: 818.4 $(M+H)^+$ Exact mass: 817.4

345 mg of the diastereomeric mixture was recrystallized from methanol (5 mL). The solids were filtered, washed with methanol (2×2 mL) and dried in vacuum oven at 40° C. overnight to afford compound 24a (78 mg, 14%, 93% de) as a white powder. LC-MS: Method E; Rt: 5.7 min m/z: 818.4 $(M+H)^+$ Exact mass: 817.4

SFC: Column: (OD)-H 250 mm×4.6 mm; Flow: 3.5 mL/min; Mobile phase: 40% MeOH 10.00 min Temperature: 30° C.; Rt (3.29 min, 24a) UV: 97.7%; Rt (4.55 min, 24b) UV: 2.3%

The filtrate was purified by Preperative SFC (Chiralpak Diacel OD 20×250 mm; mobile phase (CO₂, methanol with 0.2% iPrNH₂)). The desired fractions were collected and evaporated yielding compound 24a (54 mg, 10%, 100% de) as a white powder.

LC-MS: Method E; Rt: 5.7 min m/z: 818.4 (M+H)⁺ Exact mass: 817.4; SFC Column: (OD)-H 500 mm×4.6 mm; Flow: 3 mL/min; Mobile phase: 40% MeOH (containing 0.2% iPrNH₂) hold 19.50 min, 40-50% MeOH (containing 0.2% iPrNH₂) hold 4.10 min; Temperature: 50° C.; Rt (6.8 min, 24a) UV: 100.00; Rt (8.0 min, 24b) UV: 0.00% and 24b as a white powder (130 mg 25%, 100% de). LC-MS: Method E; Rt: 5.5 min m/z: 818.4 (M+H)⁺ Exact mass: 817.4; Column: (OD)-H 500 mm×4.6 mm; Flow: 3 mL/min; Mobile phase: 40% MeOH (containing 0.2% iPrNH₂) hold 19.50 min, 40-50% MeOH (containing 0.2% iPrNH₂) hold 4.10 min; Temperature: 50° C.; Rt (6.8 min); UV: 0.0%; Rt (8.0 min, 24b) UV: 100.0%

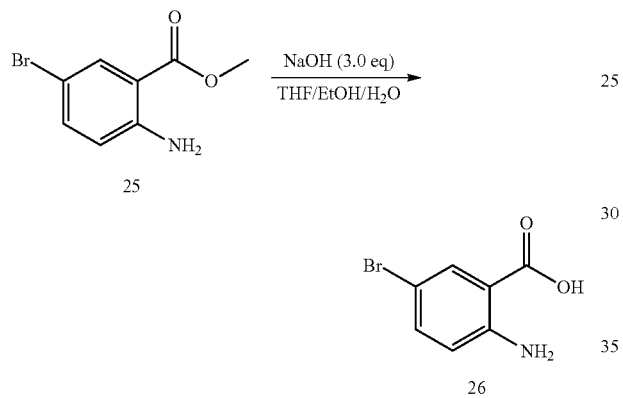

Compound 25 (10 g, 43.5 mmol) and NaOH (5.2 g, 130.4 mmol) were dissolved in H₂O (60 mL), CH₃CH₂OH (60 mL) and THF (180 mL). The reaction mixture was stirred for 12 hours at room temperature. The organic solvent was removed in vacuo. The mixture was then extracted with ethyl acetate (2×100 mL). The water layer was neutralized with 1 N HCl (till pH=4) and extracted with ethyl acetate (3×100 mL). The combined organic layers were concentrated under vacuum resulting in compound 26 (9.1 g, 97% yield).

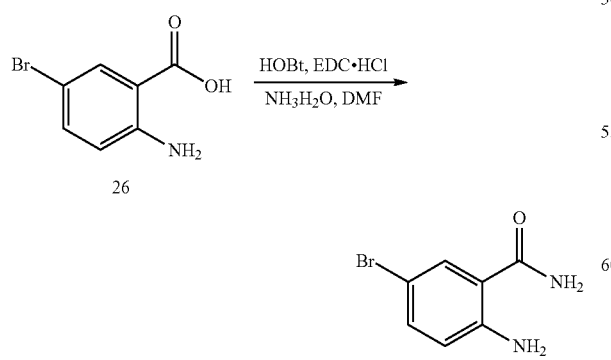

Compound 26 (9.1 g, 42.1 mmol), HOBT (13.6 g, 101.1 mmol) and EDC.HCl (19.4 g, 101.1 mmol) were dissolved in DMF (60 mL) and NH₃.H₂O (30 mL) was added slowly. The reaction mixture was stirred for 15 hours at room temperature. The solvent was then removed in vacuo. The residue was dissolved in ethyl acetate (100 mL) and washed with 1 N NaOH (20 mL), followed by brine, dried over Na₂SO₄ and concentrated under vacuum resulting in compound 27 (7.6 g, 84% yield).

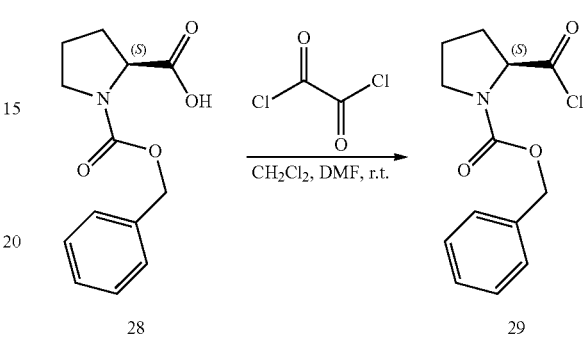

Compound 28 (15.7 g, 63.1 mmol) was dissolved in dry CH₂Cl₂ (250 mL) and DMF (1.5 mL) was added to the solution. Oxalyl chloride (13.5 mL, 157.5 mmol) was added drop wise at room temperature. The reaction mixture was stirred for 0.5 hour at room temperature. The reaction mixture was concentrated under vacuum and the residue (22 g) was used directly without further purification.

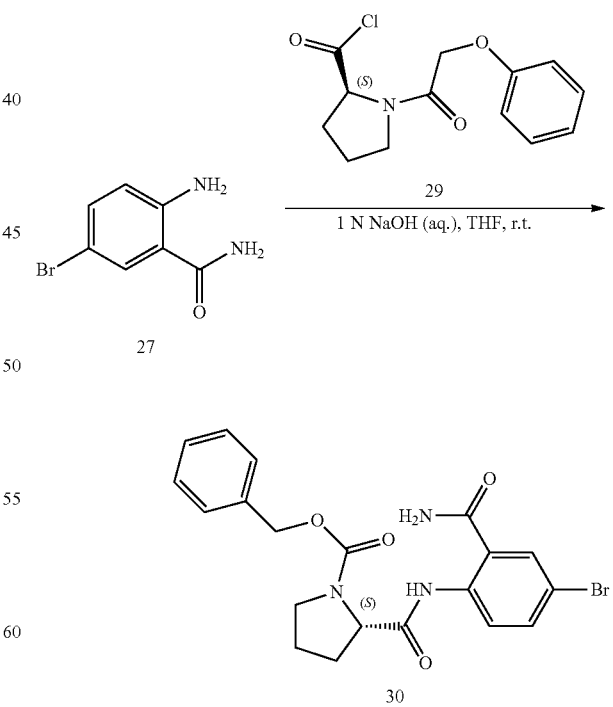

To the solution of Compound 29 (22 g, crude mixture) in dry THF (250 mL), compound 27 (7.6 g, 35.3 mmol) and 1 N NaOH (aq. 85 mL, 85 mmol) were added. The mixture was stirred for 1 hour at room temperature. The reaction mixture was then extracted with ethyl acetate (3×100 mL). The combined organic layers were washed with 1 N NaOH in water (15 mL), brine, dried over Na$_2$SO$_4$ and concentrated under vacuum resulting in compound 30.

Method A1; Rt: 1.36 min. m/z=: 446.1 (M+H)$^+$ Exact mass: 445.1

$[\alpha]_{589}^{20}$=0.75 (CH$_2$Cl$_2$, 9.47 mg/mL)

SFC: Columns: Chiralpak OD-3 50 mm*4.6 mm; 3 um; Flow: 4 mL/min; Mobile phase: A: CO$_2$ B: EtOH (0.05% Diethylamine; 5 to 40% B in A, Temperature 40° C.; Rt: 1.4 min SFC: Columns: Chiralpak AS-H 150 mm*4.6 mm; 5 um; Flow: 3 mL/min; Mobile phase: A: CO$_2$ B: MeOH (0.05% Diethylamine; 5 to 40% B in A, Temperature 40° C.; Rt: 4.4 min

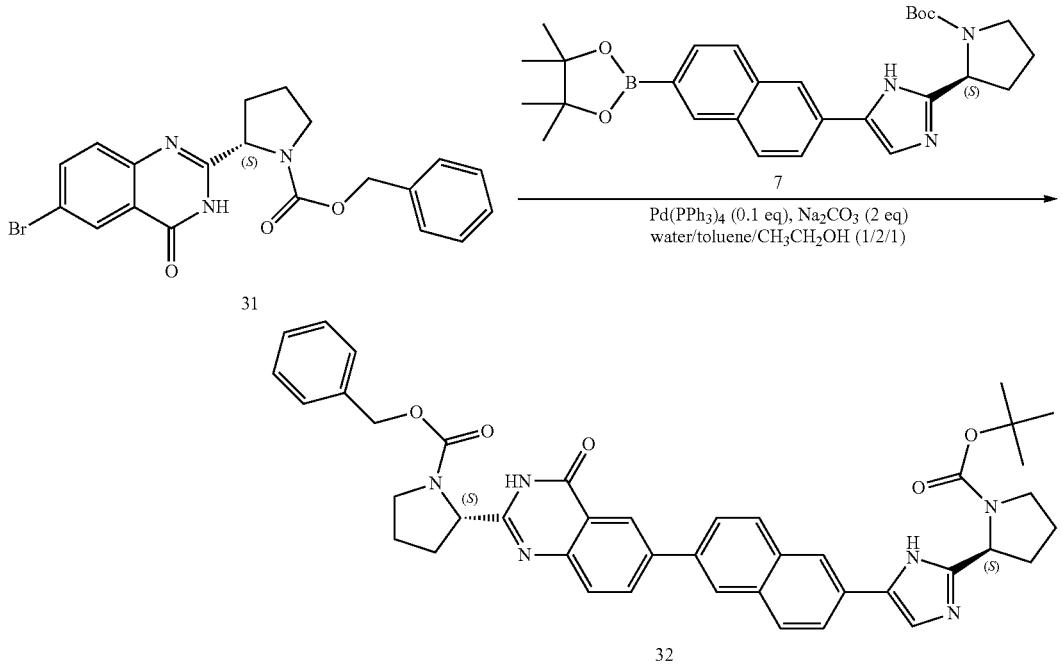

Pd(PPh$_3$)$_4$ (3.0 g, 2.6 mmol) was added to the mixture of compound 31 (11 g, 25.7 mmol), compound 7 (12.5 g, 25.7 mmol), Na$_2$CO$_3$ (5.4 g, 51.4 mmol), water (110 mL), CH$_3$CH$_2$OH (110 mL) and toluene (220 mL) in one portion under nitrogen. The mixture was stirred for 10 hours at 80° C. The organic solvent was removed under vacuum and the water layer was extracted by ethyl acetate (3×200 mL). The combined organic layers were washed by brine and then dried over Na$_2$SO$_4$ and concentrated to dryness. The residue was purified by column chromatography (petroleum ether/ethyl acetate=2/1 to 1/2). The obtained product was further purified by preparative high-performance chromatography (eluent: CH$_3$CN/H$_2$O=20/80 to 70/30, 0.1% CF$_3$COOH). The desired fraction was collected and the pH value of the solution was adjusted to about 8 by adding K$_2$CO$_3$. Then the organic solvent was removed under reduced pressure. The aqueous layer was extracted with ethyl acetate (3×300 mL). The organic layers were combined and dried under Na$_2$SO$_4$. The solution was evaporated resulting in compound 32 (23% yield).

Method C; Rt: 4.21 min. m/z=: 711.3 (M+H)$^+$ Exact mass: 710.3

SFC: Columns: Chiralpak OJ-H 250 mm×4.6 mm; 5 um; Flow: 2.5 mL/min; Mobile phase: A: CO$_2$ B: MeOH (0.05% Diethylamine; 40% B in A, Temperature 40° C.: Rt: 5.47 min $[\alpha]_{589}^{20}$=−44.54 (CH$_2$Cl$_2$, 5.25 mg/mL)

SFC: Columns: Chiralpak AS-H 250 mm*4.6 mm; 5 um; Flow: 2.5 mL/min; Mobile phase: A: CO$_2$ B: MeOH (0.05% Diethylamine; 40% B in A, Temperature 40° C.: Rt: 4.25 min

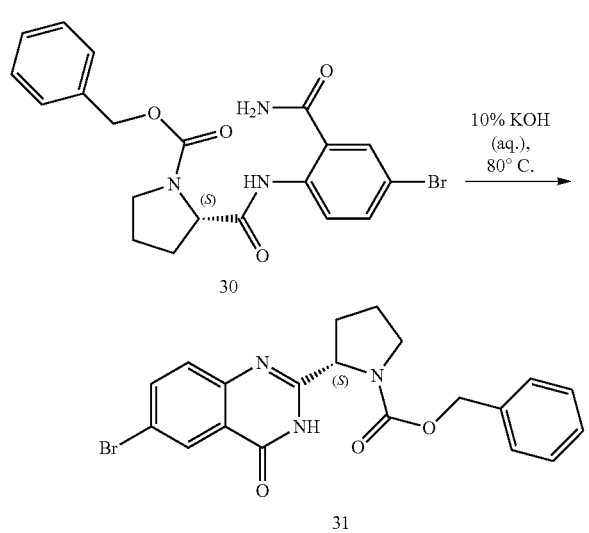

Compound 30 (17 g, 38.1 mmol) in CH$_3$CH$_2$OH (200 mL) and 10% KOH (34 mL) was heated to 80° C. for 3 hours. The reaction mixture was cooled to 0° C. and neutralized to pH=7 by carefully adding concentrated HCl. The resulting precipitate was collected by filtration and washed by ethyl acetate/hexane (5/1) resulting in compound 31 (12.6 g; 77%). Method C; Rt: 4.27 min. m/z=: 428.0 (M+H)$^+$ Exact mass: 427.1

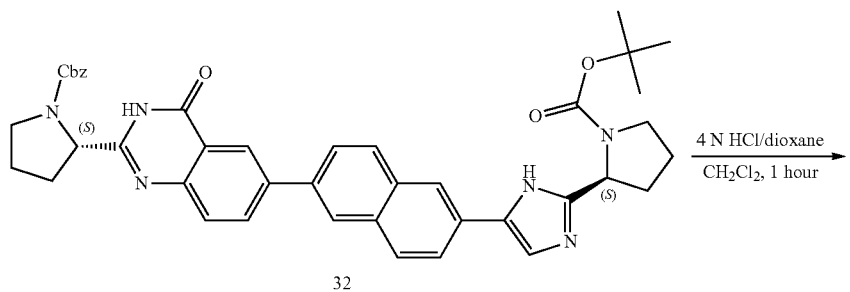

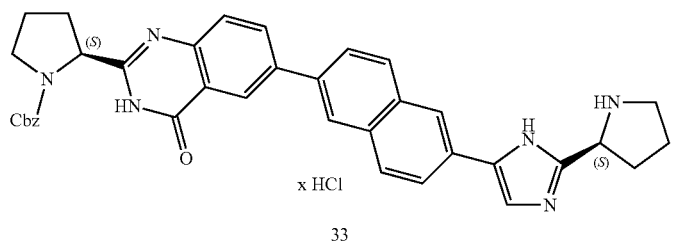

To the solution of compound 32 (3.2 g, 4.5 mmol) in CH$_2$Cl$_2$ (20 mL) was added dropwise 4 N HCl in dioxane (5.6 mL) at 0° C. When the starting material was consumed completely, the solvent was removed under vacuum. The residue was washed by t-butyl methyl ether (2×10 mL) to afford compound 33 (2.47 g).

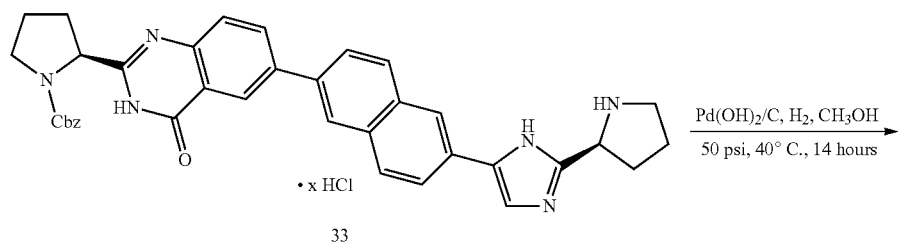

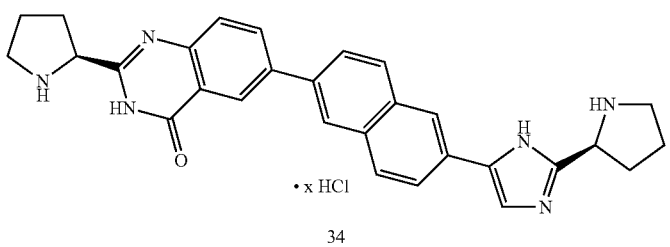

Pd(OH)$_2$/C (0.3 g, 0.43 mmol) was added to the solution of Compound 33 (2.47 g, 3.82 mmol) in CH$_3$OH under nitrogen. The resulting mixture was hydrogenated at 40° C. under the H$_2$ (50 psi) for 14 hours. The mixture was filtered on celite and concentrated. The residue (1.2 g, compound 34) was used directly in next step without further purification.

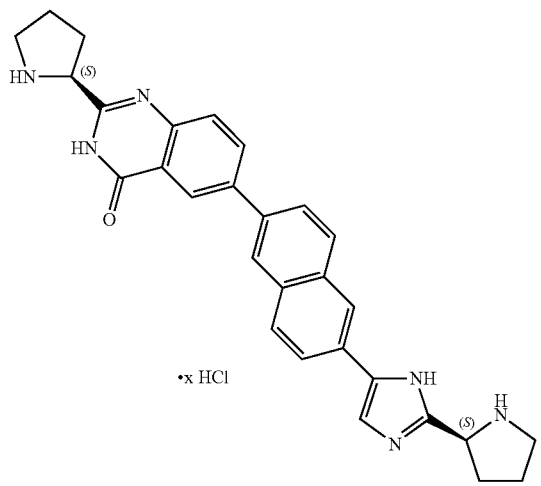

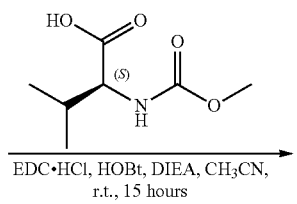

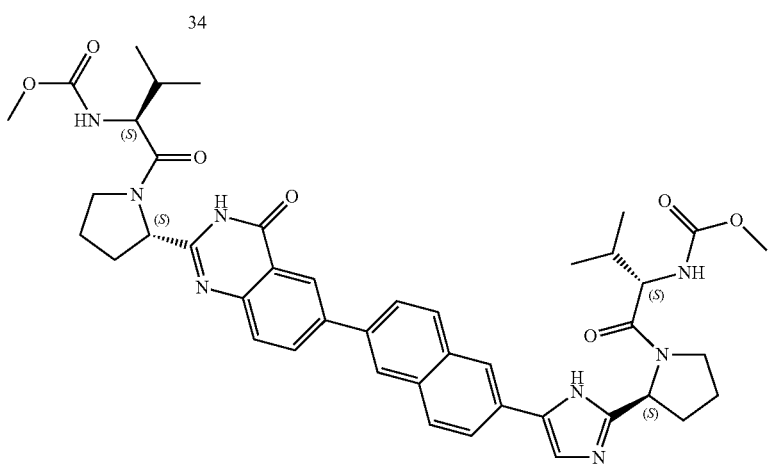

To a solution of (S)-2-(methoxycarbonylamino)-3-methylbutanoic acid (1.05 g, 6 mmol) in CH$_3$CN (20 mL) were added HOBT (0.81 g, 6 mmol) and EDC.HCl (1.14 g, 6 mmol). The mixture was stirred at 20° C. for 1 hour. Then, compound 34 (1.2 g) was added. The slurry was cooled to 0° C. and diisopropylethylamine (1.6 g) was added. The mixture was stirred at 20° C. for 15 hours. The mixture was concentrated and diluted with CH$_2$Cl$_2$ (30 mL) and aqueous 0.5 N NaOH (15 mL). The organic layer was separated and washed with brine (3×15 mL). The combined organic layers were dried over Na$_2$SO$_4$ and concentrated to give the crude product. The crude product was purified by preparative high-performance chromatography (eluent: CH$_3$OH/H$_2$O=40/60 to 70/30, 0.1% CF$_3$COOH). The desired fraction was collected and the pH value of the solution was adjusted to about 8 with K$_2$CO$_3$. Then CH$_3$OH was removed under reduced pressure and the aqueous layer was extracted by ethyl acetate (3×300 mL). The organic layers were combined and dried over Na$_2$SO$_4$. The solution was evaporated resulting in compound 35 (1.0 g).

$^1$H NMR (400 MHz, DMSO-d$_6$, main isomer described) δ ppm 11.79-12.44 (m, 2 H, two main singlets at 11.84 and 12.34) 7.82-8.49 (m, 8 H) 7.56-7.68 (m, 2 H) 7.23-7.33 (m, 2 H) 5.09-5.17 (m, 1 H) 4.78-4.87 (m, 1 H) 4.07-4.17 (m, 2 H) 3.73-3.96 (m, 4 H) 3.55 (2×s, 6 H) 1.89-2.36 (m, 10 H) 0.79-1.07 (m, 12 H)

Method C; Rt: 3.97 min. m/z=: 791.5 (M+H)$^+$ Exact mass: 790.4; SFC: Columns:

Chiralpak OJ-H 250 mm×4.6 mm; 5 um; Flow: 2.5 mL/min; Mobile phase: A: CO$_2$ B: MeOH (0.05% Diethylamine; 40% B in A, Temperature 40° C.: Rt: 3.05 min [α]$_{589}^{20}$=−24.25 (CH$_2$Cl$_2$, 2.55 mg/mL).

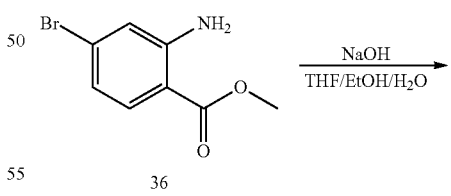

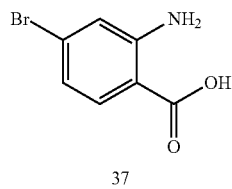

Compound 36 (10 g, 43.5 mmol) and NaOH (5.2 g, 130.4 mmol) were dissolved in H$_2$O (40 mL), CH$_3$CH$_2$OH (40 mL) and THF (120 mL). The reaction mixture was stirred for 3 hours at 50° C. The organic solvent was then removed under vacuum. The residue was extracted with ethyl acetate (3×50 mL). The water layer was acidified with con. HCl until pH=2 and extracted with ethyl acetate (3×100 mL). The combined organic layers were concentrated under vacuum to afford product 37 (9.3 g, 98% yield).

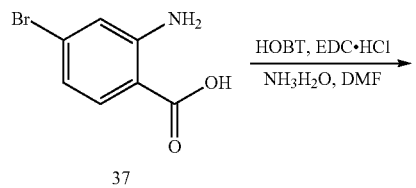

Compound 37 (9.3 g, 43.1 mmol), HOBT (13.4 g, 99 mmol) and EDC.HCl (19 g, 99 mmol) were dissolved in DMF (40 mL). The solution was stirred at 20° C. for 30 minutes. To the solution, NH$_3$.H$_2$O (20 mL). was slowly added The reaction mixture was stirred for 15 hours at room temperature. The solvent was removed in vacuo. The residue was dissolved in ethyl acetate (100 mL). The mixture was washed with saturated NaHCO$_3$ and NH$_4$Cl aqueous solution. The organic layer was dried over Na$_2$SO$_4$ and concentrated under vacuum to give the compound 38 (6.2 g, 67% yield).

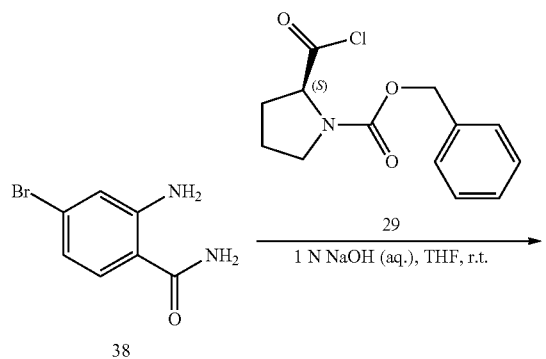

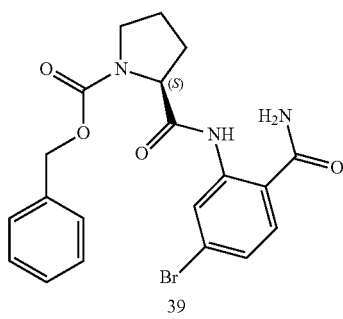

To the solution of compound 29 (7.0 g, 26.1 mmol) in dry THF (100 mL) was added compound 38 (5.6 g, 26.1 mmol) and 1 N NaOH (aq. 52 mL, 52.2 mmol). The mixture was stirred for 1 hour at room temperature. The reaction mixture was extracted with ethyl acetate (3×50 mL). The combined organic layers were washed with 1 N NaOH in water (50 mL), brine, dried over Na$_2$SO$_4$ and concentrated under vacuum resulting in compound 39 (8.3 g, 71% yield). Method A1; Rt: 1.37 min. m/z=: 468.1 (M+Na)$^+$ Exact mass: 445.1

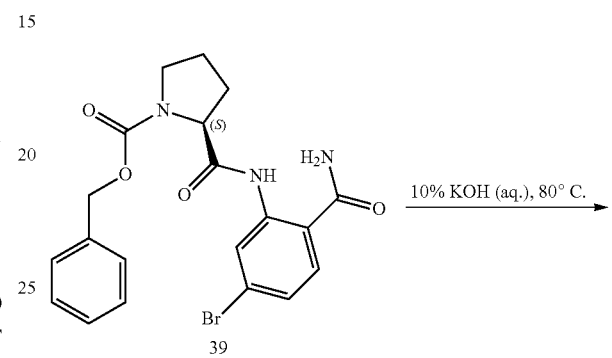

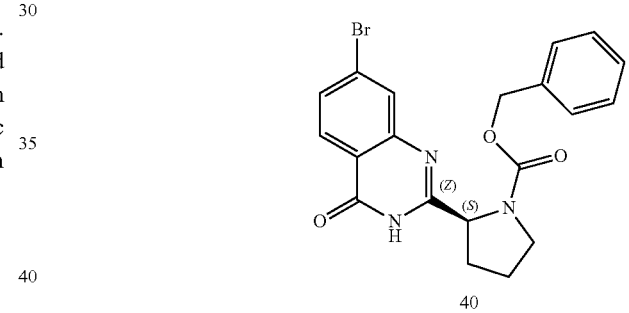

The solution of compound 39 (8.3 g, 18.6 mmol) in CH$_3$CH$_2$OH (100 mL) and 10% KOH (17 mL) was heated to 80° C. for 3 hours. The reaction mixture was cooled to 0° C. and neutralized to pH=7 with 10 N HCl aqueous solution. The mixture was filtrated and the filtrate was concentrated. The residue was dissolved in CH$_2$Cl$_2$ (80 mL) and washed with brine. The organic layer was dried over Na$_2$SO$_4$ and concentrated under vacuum. The residue was purified by flash column (eluent: petroleum ether/ethyl acetate=10/1 to 1/3) resulting in compound 40 (1.8 g, 21% yield). Method A; Rt: 1.42 min. m/z=: 428.1 (M+H)$^+$ Exact mass: 427.1

SFC: Columns: Chiralpak AD-H 50 mm*4.6 mm; 3 um; Flow: 4 mL/min; Mobile phase: A: CO$_2$ B: EtOH (0.05% Diethylamine; 5% to 40% B in A, Temperature 40° C.: Rt: 1.98 min SFC: Columns: Chiralpak OD-H 50 mm*4.6 mm; 3 um; Flow: 4 mL/min; Mobile phase: A: CO$_2$ B: EtOH (0.05% Diethylamine; 5% to 40% B in A, Temperature 40° C.: Rt: 1.45 min

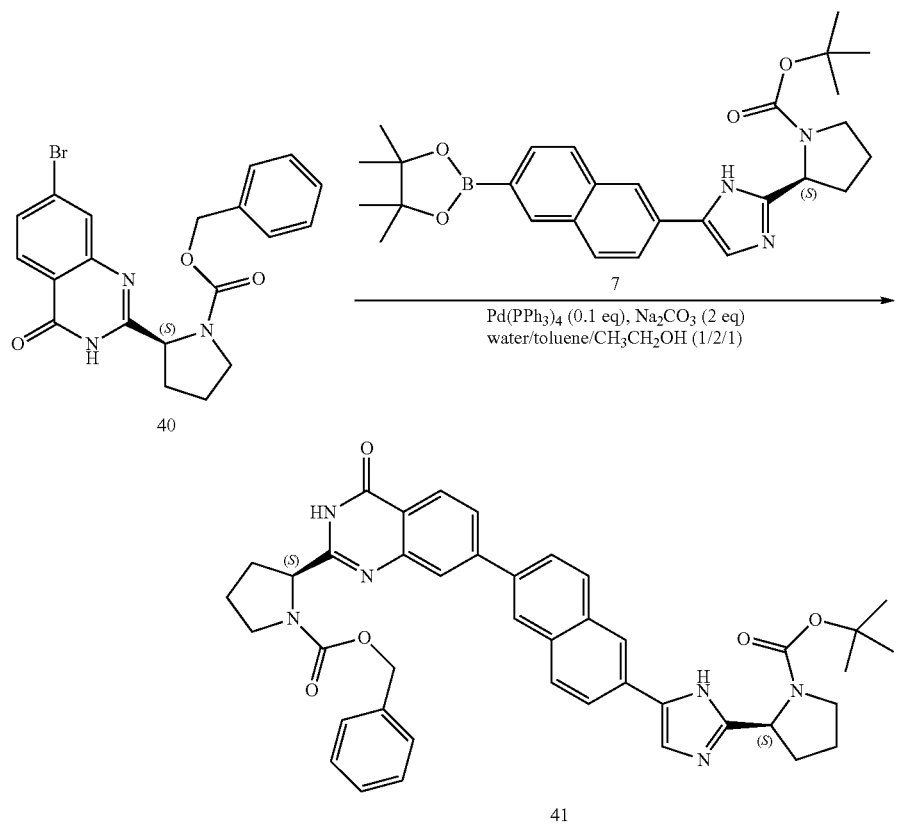

Pd(PPh₃)₄ (0.27 g, 0.23 mmol) was added to the mixture of compound 40 (1 g, 2.33 mmol), compound 7 (1.14 g, 2.33 mmol), Na₂CO₃ (0.5 g, 4.67 mmol), water (11.3 mL), CH₃CH₂OH (10 mL) and toluene (20 mL) in one portion under nitrogen. The mixture was stirred for 10 hours at 90° C. The organic solvent was removed under vacuum. The residue was purified by column (eluent: petroleum ether/ethyl acetate=10/1 to 1/3). The obtained compound 41 was re-purified by preparative high-performance liquid chromatography (eluent: CH₃CN/H₂O=30/70 to 60/40, 0.1% CF₃COOH). The desired fraction was collected and the pH of the solution was adjusted to about 10 with K₂CO₃. Then CH₃CN was removed under reduced pressure. The aqueous layer was extracted with CH₂Cl₂ (3×15 mL) and the organic layers were combined and dried over Na₂SO₄. The solution was evaporated and the residue was dried under vacuum resulting in compound 41 (0.58 g, 35% yield).

Method C; Rt: 4.11 min. m/z=: 711.3 (M+H)⁺ Exact mass: 710.3

SFC: Columns: Chiralpak OD-H 250 mm*4.6 mm; 5 um; Flow: 2.35 mL/min; Mobile phase: A: CO₂ B: EtOH (0.05% Diethylamine; 40% B in A, Temperature 40° C.: Rt: 8.45 min SFC: Columns: Chiralpak OJ-H 250 mm*4.6 mm; 5 um; Flow: 2.35 mL/min; Mobile phase: A: CO₂ B: MeOH (0.05% Diethylamine; 40% B in A, Temperature 40° C.: Rt: 5.72 min

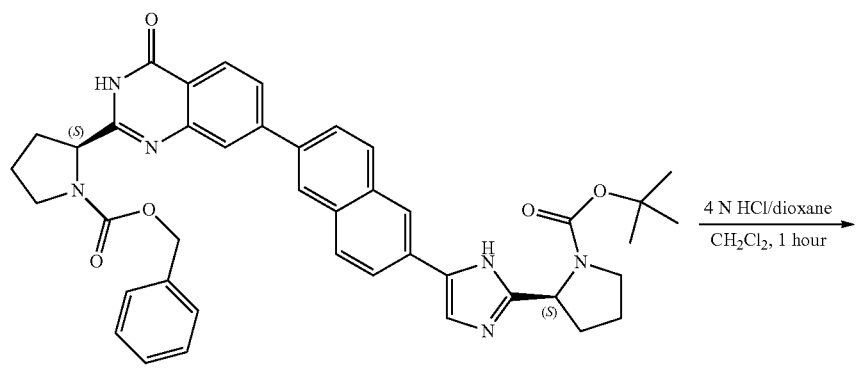

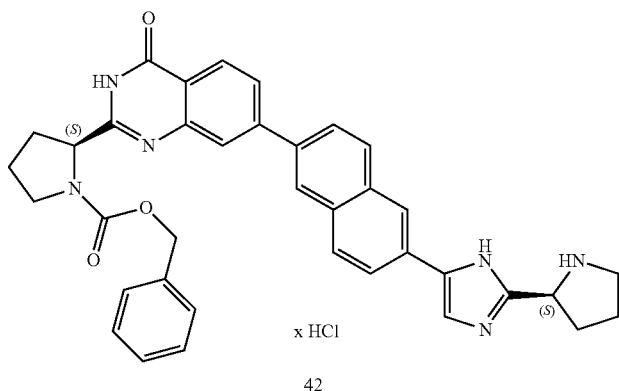

42

To the solution of compound 41 (0.58 g, 0.82 mmol) in CH$_2$Cl$_2$ (5 mL), 4 N HCl in dioxane (0.35 mL) was added dropwise at 0° C. After complete conversion to compound 42, the solvent was removed in vacuo. The residue was washed with t-butyl methyl ether (2×3 mL) resulting in compound 42 (0.5 g). Method A; Rt: 0.98 min. m/z=: 611.5 (M+H)$^+$ Exact mass: 610.3

Pd(OH)$_2$/C (0.15 g, 0.22 mmol) was added to the solution of Compound 42 (0.5 g) in CH$_3$OH under nitrogen. The resulting mixture was hydrogenated at 40° C. under the pressure of 50 psi for 18 hours. The mixture was filtered on celite and concentrated. The residue was used directly in next step without further purification (0.38 g).
Method A; Rt: 1.02 min. m/z=: 477.3 (M+H)$^+$ Exact mass: 476.2

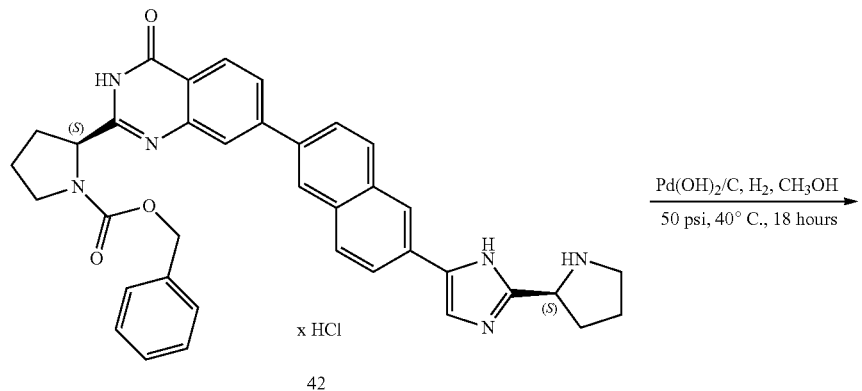

42

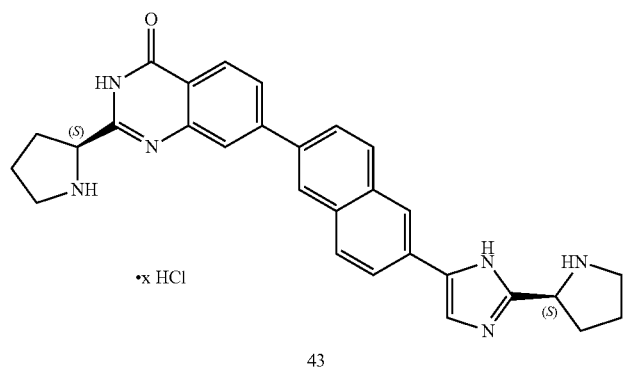

43

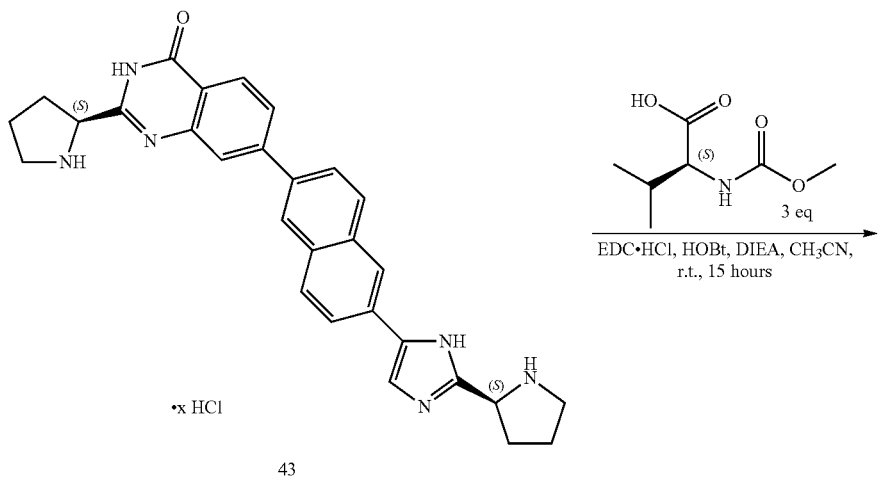

43

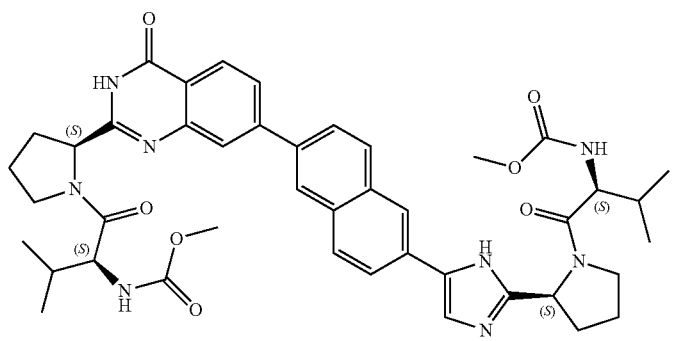

44

To a solution of (S)-2-(methoxycarbonylamino)-3-methylbutanoic acid (0.43 g, 2.4 mmol) in CH₃CN (10 mL) were added HOBT (0.43 g, 3.2 mmol) and EDC.HCl (0.63 g, 3.2 mmol). The mixture was stirred at 20° C. for 1 hour. Then compound 43 (0.38 g) was added. The slurry was cooled to 0° C. and diisopropylethylamine (0.51 g, 4.0 mmol) was added. The mixture was stirred at 20° C. for 15 hours. The mixture was concentrated and diluted with CH₂Cl₂ (50 mL) and 0.5 N NaOH (20 mL; aq.). The organic layer was separated and washed with brine (3×10 mL). After evaporation of the volatiles, the crude product was purified by preparative high-performance liquid chromatography (eluent: CH₃CN/H₂O=30/70 to 60/40, 0.1% CF₃COOH). The desired fraction was collected and the pH of the solution was adjusted to about 6 with 0.5N citric acid. Then CH₃CN was removed under reduced pressure. The aqueous layer was extracted with CH₂Cl₂ (3×50 mL) and the organic layers were combined and dried under Na₂SO₄. The solution was evaporated and the residue was dried under vacuum resulting in compound 44 (181 mg). Method C; Rt: 3.86 min. m/z=: 791.5 (M+H)⁺ Exact mass: 790.4; SFC: Columns: Chiralpak OD-H 50 mm*4.6 mm; 3 um; Flow: 4 mL/min; Mobile phase: A: CO₂ B: MeOH (0.05% Diethylamine; 40% B in A, Temperature 40° C.: Rt: 1.42 min SFC: Columns: Chiralpak AS-H 150 mm*4.6 mm; 5 um; Flow: 3 mL/min; Mobile phase: A: CO₂ B: EtOH (0.05% Diethylamine; 5% to 40% B in A, Temperature 40° C.: Rt: 5.26 min $[\alpha]_{589}^{20}$=−228.0 (CH₂Cl₂, 1 mg/mL)

¹H NMR (400 MHz, DMSO-d₆, main isomer described) δ ppm 11.67-12.44 (2 H, m, two main singlets at 11.82 and 12.26) 7.61-8.36 (10 H, m) 7.23 (2 H, d, J=8.3 Hz) 5.08-5.16 (1 H, m) 4.82 (1 H, dd, J=4.9, 7.7 Hz) 4.06-4.17 (2 H, m) 3.70-3.98 (4 H, m) 3.55 (3H, s) 3.54 (3 H, s) 1.85-2.35 (10 H, m) 0.8-1.05 (12 H, m)

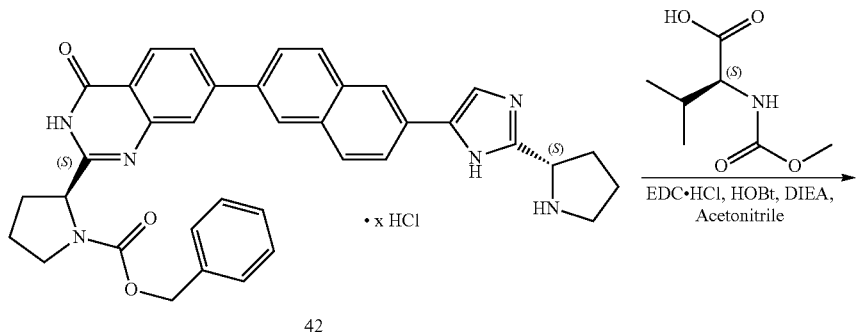

42

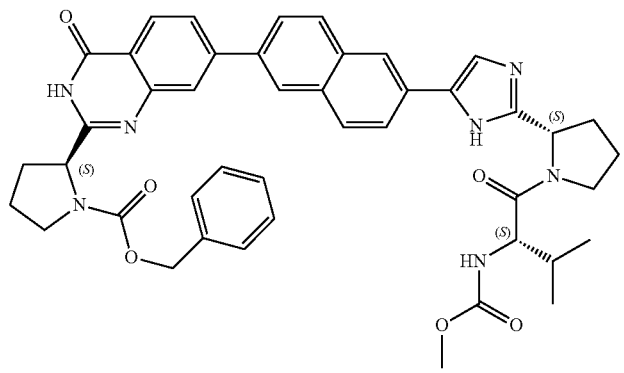

42a

EDC.HCl (0.63 g, 3.3 mmol) and HOBt (0.45 g, 3.3 mmol) were added to a solution of (S)-2-(methoxycarbonylamino)-3-methylbutanoic acid (0.58 g, 3.3 mmol) in acetonitrile (45 mL). The mixture was stirred at 10° C. for 1 hour and then compound 42 (0.9 g) was added. The mixture was cooled to 0° C. and after addition of diisopropyl-ethylamine (0.72 g, 5.6 mmol) the mixture was stirred at 10° C. for 48 hours. After filtration of the reaction mixture, the filtrate was concentrated in vacuo and the resulting residue was diluted with $CH_2Cl_2$ (20 mL) and 1 N HCl (15 mL). The solid was filtered, washed with t-butyl methyl ether (5 mL) and dried under high vacuum, to afford compound 42a (0.4 g). The organic layer was separated and washed with saturated aqueous $NaHCO_3$ (15 mL) and brine and dried on $Na_2SO_4$. After filtration, the solvent was removed in vacuo. The residue was washed with butyl methyl ether (10 mL) and dried under high vacuum resulting in more compound 42a (0.3 g).

Method A2; Rt: 0.84 min. m/z=: 767.8 (M+H)$^+$ Exact mass: 767.3

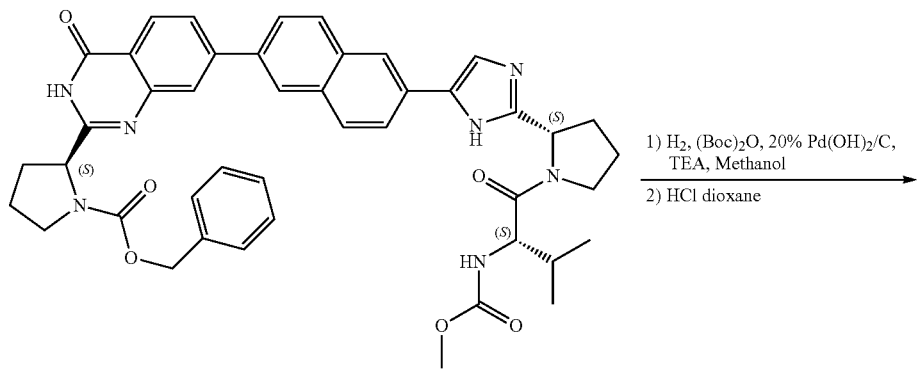

42a

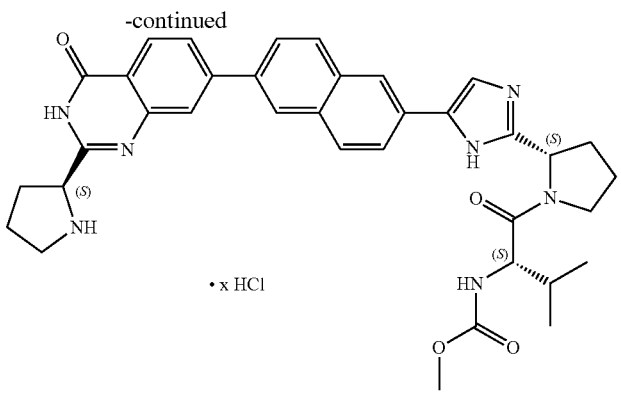

42b

A mixture of compound 42a (0.56 g), (Boc)₂O (0.34 g, 1.54 mmol, 2 eq), triethylamine (0.33 mL, 2.31 mmol) and dry 20% Pd(OH)₂/C (0.5 g) in methanol (5 mL) was stirred under hydrogen atmosphere at 10° C. for 3 hours. The mixture was filtrated and the filtrate was evaporated in vacuo. The obtained residue was dissolved in CH₂Cl₂ (10 mL) and washed with H₂O (5 mL). The organic layer was dried on Na₂SO₄ and after filtration, the filtrate was concentrated in vacuo. The obtained residue was washed with tert-butyl methyl ether (3 mL). The solid (0.47 g) was filtrated and dried under high vacuum.

Method A2; Rt: 1.00 min. m/z=: 734.4 (M+H)⁺ Exact mass: 733.4. The solid was dissolved in CH₂Cl₂ (5 mL) and 4 N HCl/dioxane (3 mL, 12 mmol) was added dropwise at 0° C. The mixture was stirred at 10° C. for 1 hour. The solvent was removed in vacuo and the residue was solidified with t-butyl methyl ether (2 mL). The solid was filtrated and dried under high vacuum to afford compound 42b (0.36 g).

Method A2; Rt: 0.82 min. m/z=: 634.1 (M+H)⁺ Exact mass: 633.3.

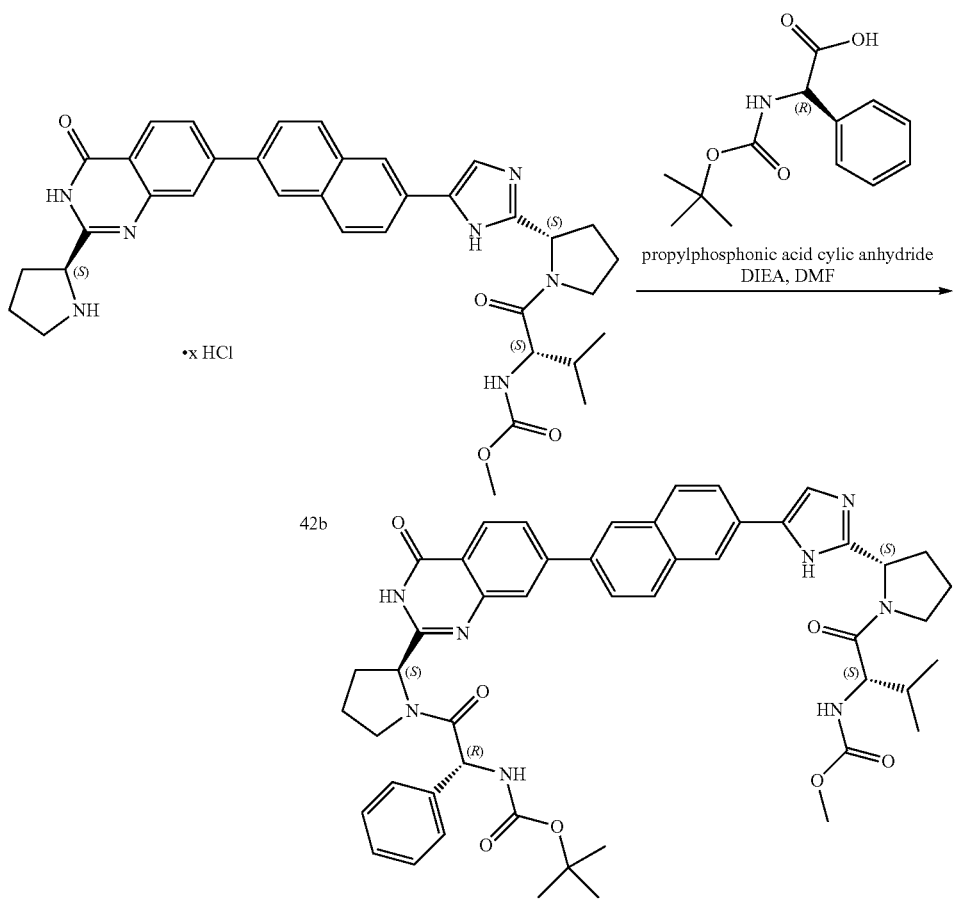

44-1

A mixture of compound 42b (0.3 g), (R)-2-(tert-butoxycarbonylamino)-2-phenylacetic acid (0.25 g, 0.99 mmol), propylphosphonic acid cylic anhydride (0.9 mL, 1.69 mmol,), diisopropylethylamine (0.6 mL, 2.7 mmol, 6 eq) and DMF (6 mL) was stirred at 10° C. for 1 hour. CH$_2$Cl$_2$ (5 mL) and saturated NaHCO$_3$ solution (3 mL) were added. The organic layer was washed with brine (2×3 mL) and dried on Na$_2$SO$_4$. After filtration, the solvent was removed in vacuo. The obtained residue was washed with tert-butyl methyl ether (3 mL). The solid was filtrated and dried under high vacuum. The residue was purified by high-performance liquid chromatography (Column: Grace Vydac 250×20 mm×5 um; Mobile phase A: water (containing 0.075% TFA, VAT) Mobile phase B: acetonitrile (containing 0.025% TFA, VAT) Flow rate: 30 mL/min, Gradient: 35-50% (v/v) B in A from 0 to 11 min). The pure fractions were collected and basified with NaHCO$_3$ to pH=8. The volatiles were removed in vacuo. The residue was extracted with CH$_2$Cl$_2$ (2×20 mL). The organic layer was washed with brine (10 mL) and dried on Na$_2$SO$_4$. After filtration, the solvent was removed in vacuo to afford compound 44-1 (0.11 g). Method C; Rt: 4.10 min. m/z=: 867.5 (M+H)$^+$ Exact mass: 866.4

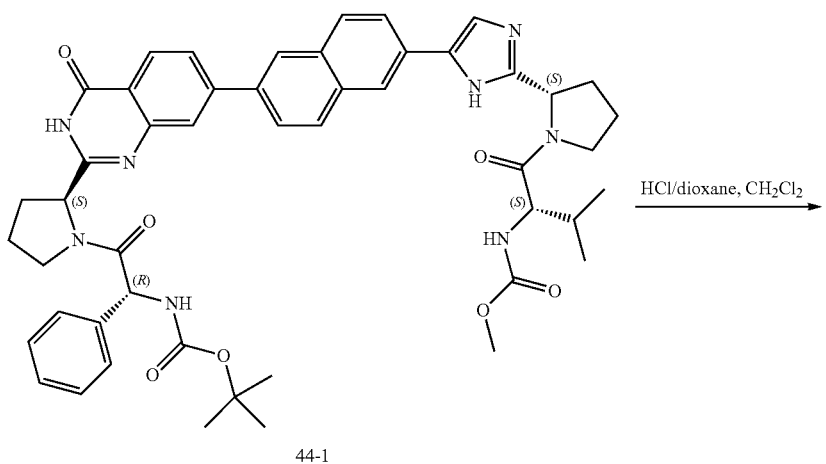

44-1

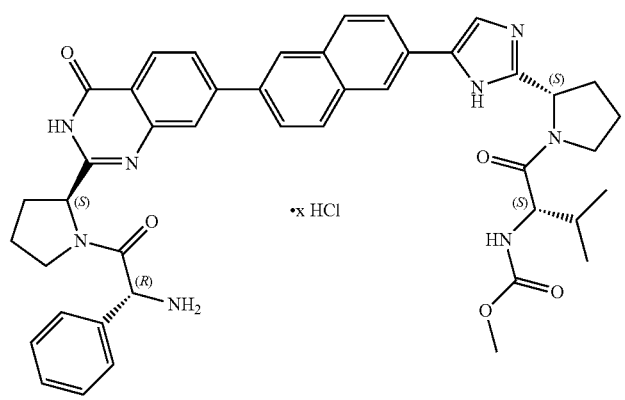

44-1a

Compound 44-1 (1.8 g, crude) was dissolved in CH₂Cl₂ (20 mL) and HCl/dioxane (6 mL, 24 mmol) was added dropwise at 0° C. The mixture was stirred at 0° C. for 2 hours. The solvent was removed in vacuo. The residue was washed with diethyl ether (3 mL) and CH₂Cl₂ (5 mL). The solid was dried under high vacuum to afford compound 44-1a (0.82 g). Method A2; Rt: 0.85 min. m/z=: 767.3 (M+H)⁺ Exact mass: 766.4

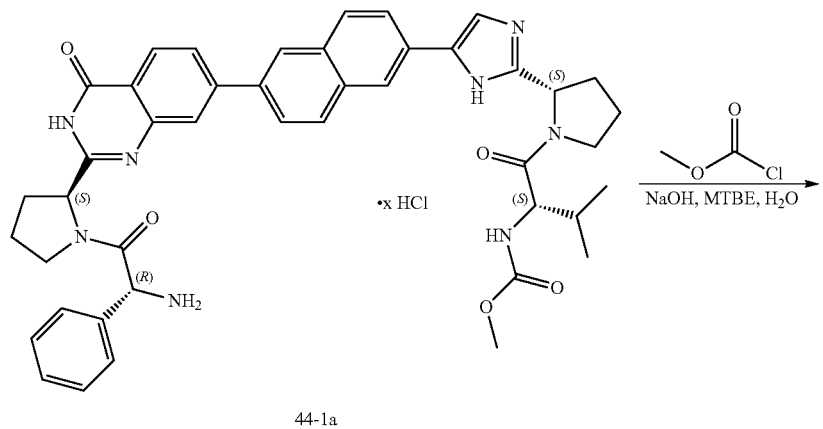

44-1a

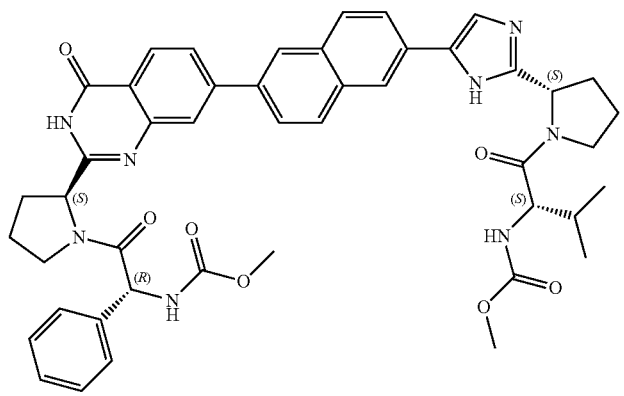

44-2

Methyl chloroformate (0.33 g, 3.49 mmol) was added to the mixture of compound 441a in H₂O (10 mL) and tert-butyl methyl ether (10 mL) at 0° C. NaOH (0.12 g, 3.1 mmol) was added. The mixture was stirred at 0° C. for 1 hour and then CH₂Cl₂ (10 mL) was added. The organic layer was washed with H₂O (10 mL) and dried (Na₂SO₄). After filtration, the solvent was evaporated in vacuo. The residue was purified by high-performance liquid chromatography (Column: Grace Vydac 250×20 mm×5u, Mobile phase A: water (containing 0.075% TFA, V/V) Mobile phase B: acetonitrile (containing 0.025% TFA, V/V), Flow rate: 30 mL/min, Gradient: 35-50% B (v/v) in A from 0 to 11 min). The pure fractions were collected and basified with saturated NaHCO₃ solution to pH=8. The volatiles were removed in vacuo. The residue was extracted with CH₂Cl₂ (2×15 mL). The organic layer was washed with brine (10 mL) and dried on Na₂SO₄. After filtration, the solvent was removed in vacuo. The resulting residue was further dried in vacuo to afford compound 44-2 (45 mg) as a white powder. Method B; Rt: 5.05 min. m/z=: 825.5 (M+H)⁺ Exact mass: 824.4

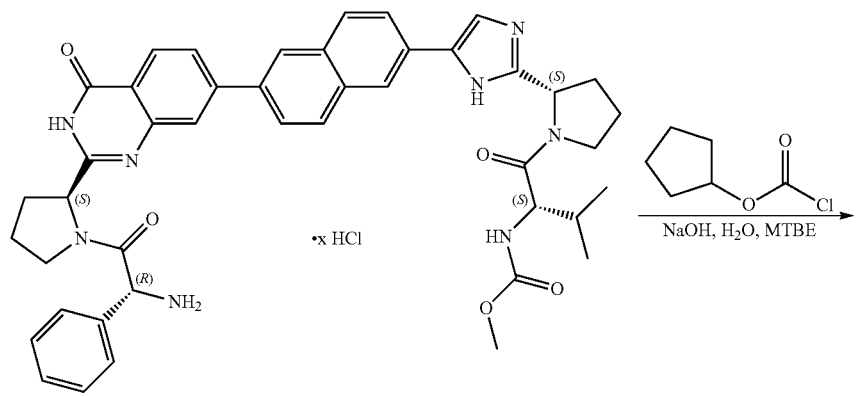

44-1a

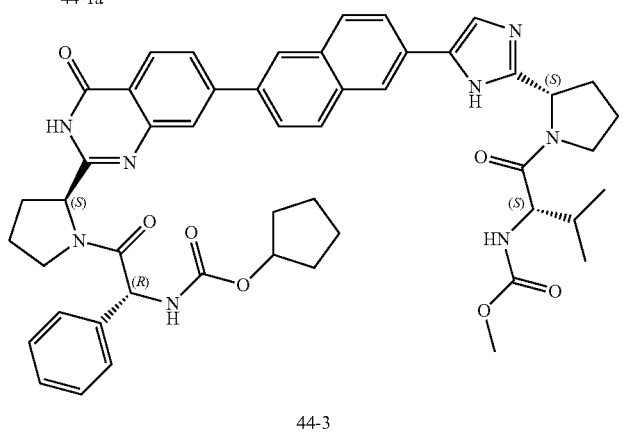

44-3

Cyclopentyl chloroformate (0.44 g, 3 mmol) was added to the mixture of compound 44-1a (0.2 g), H₂O (5 mL) and MTBE (5 mL) at 0° C. NaOH (0.1 g, 2.5 mmol) in H₂O (0.5 mL) was added. The mixture was stirred at 0° C. for 1 hour. 1 N HCl was added to until Ph=3 followed by CH₂Cl₂ (10 mL). The organic layer was washed with H₂O (10 mL). The solvent was removed in vacuo and the obtained residue was purified by high-performance liquid chromatography (Column: Grace Vydac 250×20 mm×5u, Mobile phase A: water (containing 0.075% TFA, V/V), Mobile phase B: acetonitrile (containing 0.025% TFA, V/V), Flow rate: 30 mL/min, Gradient: 35-50% B (v/v) in A from 0 to 11 min). The pure fractions were collected and basified with NaHCO₃ to pH=8. The volatiles were removed in vacuo and the obtained residue was extracted with CH₂Cl₂ (2×15 mL). The organic layer was washed with brine (10 mL) and dried on Na₂SO₄. After filtration, the solvent was removed in vacuo. The resulting residue was lypholized resulting in compound 44-3 (34 mg). Method B; Rt: 5.35 min. m/z=: 879.6 (M+H)⁺ Exact mass: 878.4

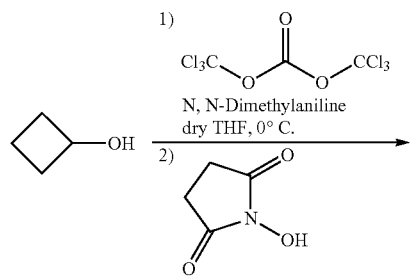

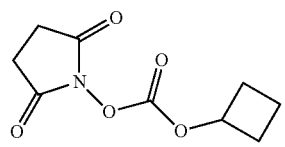

Cyclobutanol (2 g, 27.7 mmol) and N,N-Dimethylaniline (3.69 g, 30.5 mmol) were slowly added to a mixture of triphosgene (8.22 g, 27.7 mmol, 1 eq) in dry THF (20 mL) at 0° C. After 10 minutes, the reaction was warmed to 10° C. and stirred for 12 hour. Dry CH₂Cl₂ (20 mL) was added and the mixture was poured slowly into a solution of N-hydroxysuccinimide (4.14 g, 36 mmol) in dry CH₂Cl₂ (20 mL) at 0° C. The mixture was stirred at 10° C. for 10 hours. H₂O (20 mL) was added and the mixture was stirred for 3 hours. The mixture was extracted with ethyl acetate (2×30 mL). The organic layer was washed with brine (20 mL) and dried over Na₂SO₄. The solvent was removed under vacuum resulting in cyclobutyl 2,5-dioxopyrrolidin-1-yl carbonate (1 g, 16% yield).

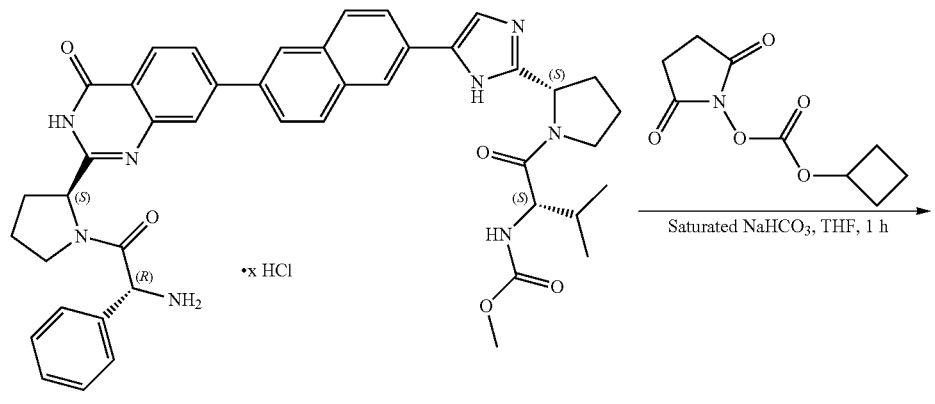

44-1a

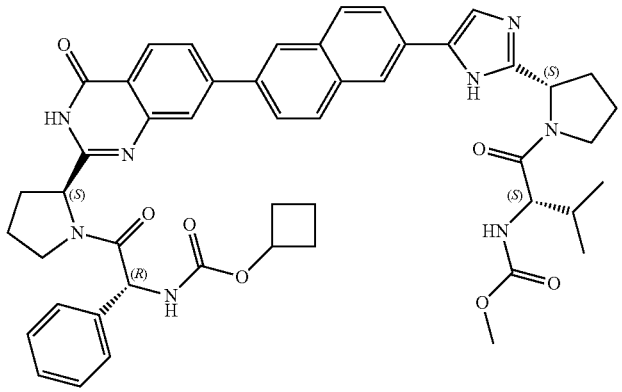

44-4

To 44-1a (0.1 g) in THF (5 mL), a saturated NaHCO₃ solution (1.25 mL) was added dropwise. Next, cyclobutyl 2,5-dioxopyrrolidin-1-yl carbonate (0.03 g) in THF (2 mL) was added dropwise. The mixture was stirred at 10° C. for 1 hour and 10% aqueous citric acid (3 mL) was added. The mixture was extracted with ethyl acetate (2×5 mL). The combined organic layers were washed with brine (2 mL) and dried over Na₂SO₄. The solvent was removed under vacuum. The residue was purified by high-performance liquid chromatography (Column: Grace Vydac 250*20 mm*5 um Mobile phase A: water (containing 0.075% TFA, V/V %) Mobile phase B: acetonitrile (containing 0.025% TFA, V/V %) Flow rate: 30 mL/min; Gradient: 35-50% B (v/v) in A from 0 to 11 min). The pure fractions were combined and basified with saturated NaHCO₃ to Ph=8. The volatiles were removed in vacuo. The resulting mixture was extracted with CH₂Cl₂ (2×15 mL). The organic layers were combined, washed with brine (10 mL) and dried over Na₂SO₄. The solvent was removed in vacuo, resulting in compound 44-4 (0.023 g)

Method B; Rt: 5.16 min. m/z=: 865.3 (M+H)⁺ Exact mass: 864.4

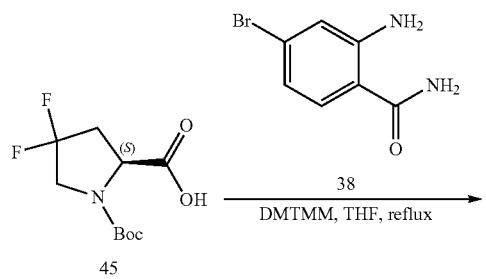

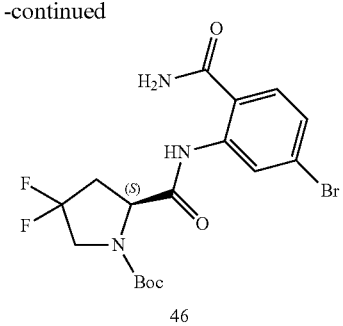

46

Compound 45 (4 g, 15.9 mmol) and 38 (3.8 g, 17.7 mmol) were dissolved in dry THF (250 mL). The mixture was heated to 80° C. and stirred for 1 hour. Then 4-(4,6-Dimethoxy [1.3.5] triazin-2-yl)-4-methylmorpholinium chloride hydrate (DMTMM, 1.2 eq) was added and the mixture was stirred at 80° C. overnight. The mixture was concentrated, water (60 mL) was added and then extracted with CH₂Cl₂ (3×150 mL). The organic phase was separated, dried over Na₂SO₄, filtered and the solvent was removed under vacuum. The crude product was purified by preparative high-performance liquid chromatography (column: C18, eluent: CH₃CN/H₂O from 47/53 to 77/23, 0.1% CF₃COOH). The desired fraction was collected and basified by saturated NaHCO₃ (aq.). The mixture was concentrated and extracted with CH₂Cl₂ (2×200 mL). The organic layer was dried over Na₂SO₄ and the solvent was evaporated under vacuum. The pure product was dried under vacuum (4.2 g, 59%). Method F; Rt: 1.63 min. m/z=: 470.0 (M+Na)⁺ Exact mass: 447.1

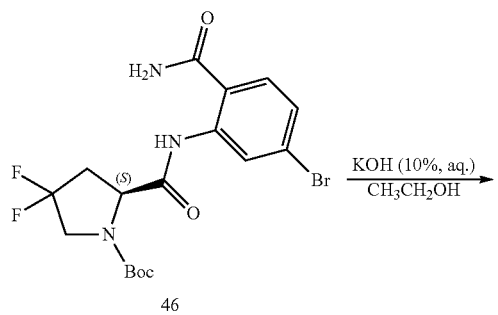

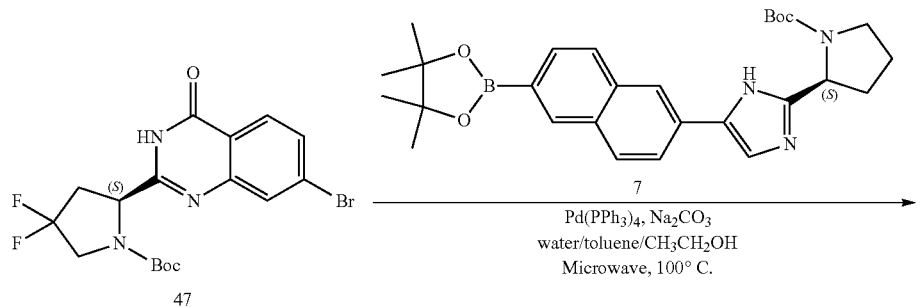

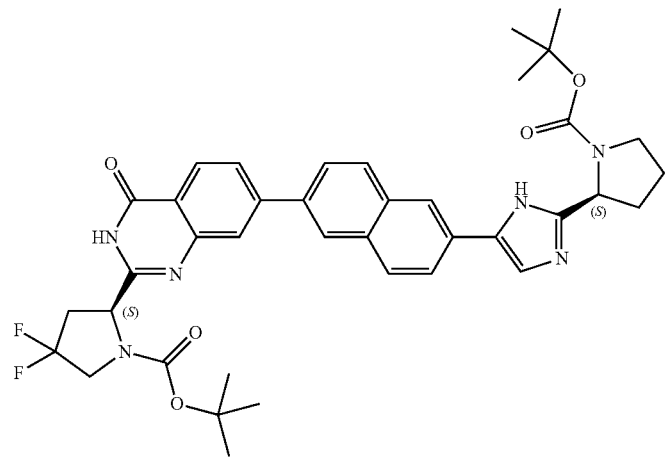

organic layers were dried over Na$_2$SO$_4$ and the solvent was removed under vacuum. The compound 47 was dried in vacuo (3.2 g, 79%). Method C; Rt: 4.31 min. m/z=: 430.0 (M+H)$^+$ Exact mass: 429.1

SFC: Columns: Chiralpak OJ-H 250 mm*4.6 mm; 5 um; Flow: 2.5 mL/min; Mobile phase: A: CO$_2$ B: MeOH (0.05% Diethylamine; 5% to 40% B in A, Temperature 40° C.:

Rt: 4.27 min

SFC: Columns: Chiralpak AD-3 150 mm*4.6 mm; 3 um; Flow: 2.5 mL/min; Mobile phase: A: CO$_2$ B: isopropanol (0.05% Diethylamine; 5% to 40% B in A, Temperature 40° C.: Rt: 5.64 min $[\alpha]_{589}^{20}=-96.8$ (CH$_3$OH, 2.5 mg/mL)

-continued

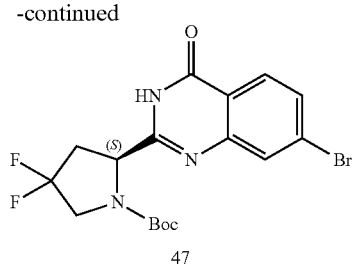

A solution of compound 46 (4.2 g, 9.4 mmol) and KOH (10% aq., 3 eq) in CH$_3$CH$_2$OH (120 mL) was stirred at 20° C. overnight. The mixture was concentrated and water (40 mL) was added. The mixture was extracted with CH$_2$Cl$_2$ (3×120 mL) and the combined organic layers were separated. The organic layers were dried over Na$_2$SO$_4$ and the solvent was removed under vacuum. The compound 47 was dried in vacuo (3.2 g, 79%).

Pd(PPh$_3$)$_4$ (0.2 eq) was added in portion to a mixture of compound 47 (2 g, 4.6 mmol), compound 7 (2.4 g, 1.1 eq) and Na$_2$CO$_3$ (2.0 eq) in H$_2$O/toluene/CH$_3$CH$_2$OH (1/2/1) (32 mL, 16 mL/batch) under nitrogen. The mixture was stirred at 100° C. under microwave for 2 hours. The mixture was concentrated and water (30 mL) was added. The mixture was extracted with CH$_2$Cl$_2$ (3×80 mL). The combined organic layers were separated, dried over Na$_2$SO$_4$ and the solvent was removed under vacuum. The crude product was purified by preparative high performance liquid chromatography preparative high-performance liquid chromatography (column: C18, eluent: CH$_3$CN/H$_2$O from 35/65 to 60/40, 0.1% CF$_3$COOH).

The desired fraction was collected and basified by saturated NaHCO$_3$ (aq.). The mixture was concentrated and extracted with CH$_2$Cl$_2$ (3×100 mL). The organic layer was separated, dried over Na$_2$SO$_4$ and the solvent was removed under vacuum. Compound 48 was dried in vacuo (1.9 g, 58%). Method F; Rt: 1.55 min. m/z=: 713.5 (M+H)$^+$ Exact mass: 712.3

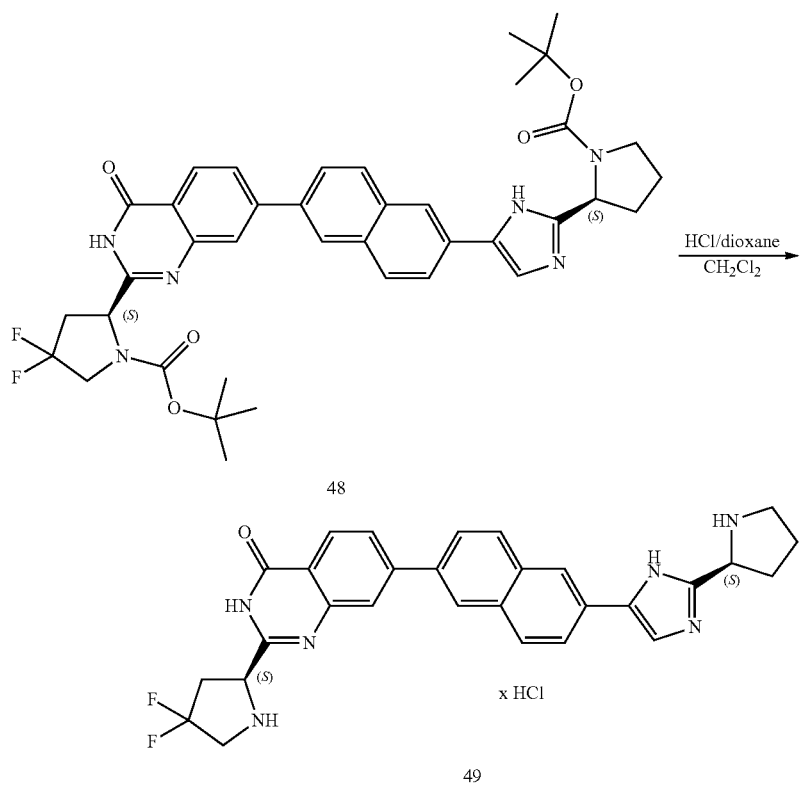
Compound 48 (1.8 g, 2.5 mmol) was dissolved in CH$_2$Cl$_2$ (30 mL) and cooled to 0° C. HCl in dioxane (4 N, 10 mL) was added dropwise at 0-5° C. and the reaction mixture was stirred at room temperature for 1 hour. The mixture was then filtered and the solid was washed with t-butyl methyl ether (20 mL). The residue (1.8 g) was used directly in next step. Method F; Rt: 1.14 min. m/z=: 513.1 (M+H)$^+$ Exact mass: 512.2
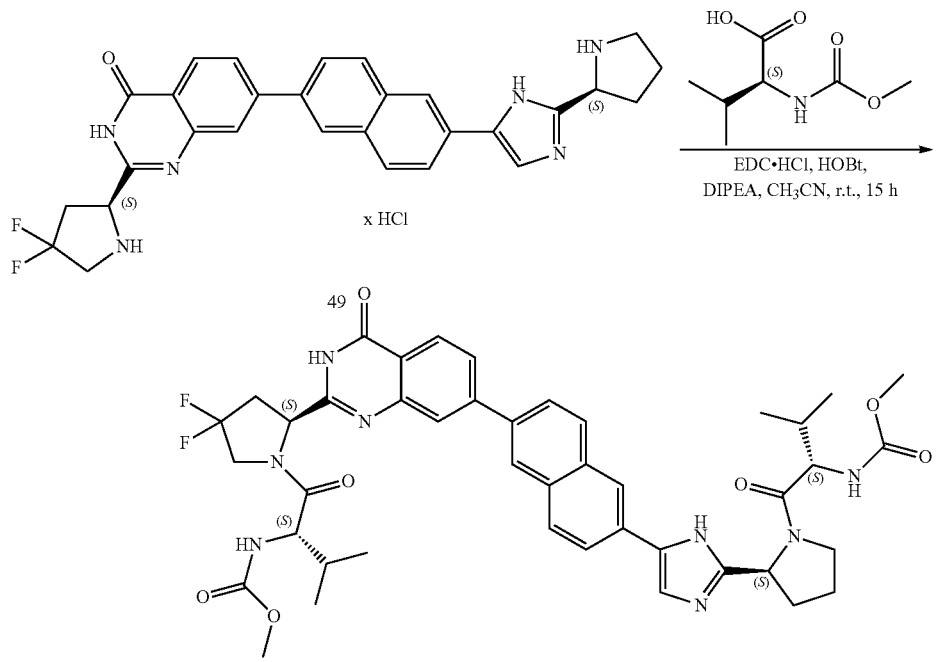

To a solution of (S)-2-(methoxycarbonylamino)-3-methylbutanoic acid (1.23 g, 7.0 mmol) in CH₃CN (50 mL) were added EDC.HCl (7.0 mmol) and HOBt (7.0 mmol,). The mixture was stirred at 0° C. for 1 hour and then compound 49 (1.7 g) was added. The slurry was then cooled to 0° C. and DIPEA (1.5 g) was added. The mixture was stirred at 20° C. for 15 hours. The mixture was concentrated and diluted with CH₂Cl₂ (30 mL) and of 0.5 N NaOH (aq.) (15 mL). The organic layer was separated and washed with brine (3×15 mL). The combined organic layer was dried over Na₂SO₄ and concentrated to give the crude product. The crude product was purified by preparative high-performance liquid chromatography (column: C18, eluent: CH₃CN/H₂O from 35/65 to 50/50, 0.1% CF₃COOH). The desired fraction was collected and basified by saturated NaHCO₃ (aq.) till pH~8. The mixture was concentrated and extracted with CH₂Cl₂ (2×100 mL). The organic layer was dried over Na₂SO₄ and the solvent was removed under vacuum. The pure product was then further purified by super-fluid chromatography (Column: Chiralpak AS 250×25 mm I.D., 20 μm Mobile phase: A: CO₂, B: Methanol (0.5% DEA); B in A from 5% to 40%, Flow: 50 mL/min). The solvent was removed under vacuum and compound 50 was obtained after lyophilization (640 mg). Method C; Rt: 3.84 min. m/z=: 827.3 (M+H)⁺ Exact mass: 826.4

$[\alpha]_{589}^{20}$=−232.8 (CH₂Cl₂, 2.5 mg/mL)

¹H NMR (400 MHz, DMSO-d₆, main isomer described) δ ppm 11.79-12.44 (m, 2 H two main singlets at 11.86 and 12.33) 8.12-8.34 (m, 3 H) 7.83-8.05 (m, 6 H) 7.63-7.69 (m, 1 H) 7.49 (d, 1 H; J=8.0 Hz) 7.31 (d, 1 H, J=8.5 Hz) 5.08-5.16 (m, 1 H) 4.94-5.05 (m, 1 H) 4.50-4.65 (m, 1 H) 4.21-4.39 (m, 1 H) 4.04-4.16 (m, 1 H) 3.93-4.04 (m, 1 H) 3.75-3.89 (m, 2 H) 3.55 (s, 6 H) 2.88-3.04 (m, 1 H) 2.60-2.77 (m, 1 H) 2.10-2.26 (m, 2 H) 1.83-2.10 (m, 4 H) 0.79-1.07 (m, 12 H)

SFC: Columns: Chiralpak AS-H 150 mm*4.6 mm; 5 um; Flow: 3 mL/min; Mobile phase: A: CO₂ B: MeOH (0.05% Diethylamine); 5 to 40% B in A,: Rt: 5.73 min SFC: Columns: Chiralpak OD-3 150 mm*4.6 mm; 3 um; Flow: 2.5 mL/min; Mobile phase: A: CO₂ B: MeOH (0.05% Diethylamine); 40% B in A,: Rt: 5.98 min SFC: Columns: Chiralpak OJ-H 250 mm*4.6 mm; 5 um; Flow: 2.5 mL/min; Mobile phase: A: CO₂ B: MeOH (0.05% Diethylamine); 40% B in A,: Rt: 3.49 min

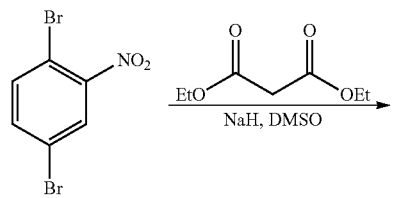

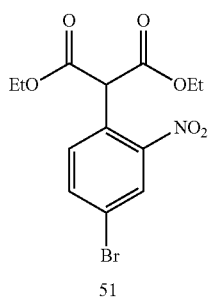

51

NaH (60%, 3.13 g, 78 mmol, 2 equiv.) was added to DMSO (100 mL) followed by dropwise addition of diethyl malonate (12.54 g, 78 mmol, 2 equiv.). The reaction mixture was heated to 100° C. for 40 minutes. The mixture was cooled to room temperature, 1,4-dibromo-2-nitrobenzene (10 g, 35.60 mmol) was added, stirring was continued for 30 minutes at room temperature, and then heated to 100° C. for 1 hour. The reaction mixture was quenched with aq sat.NH₄Cl (50 mL). Then, EtOAc (150 mL) was added, and the organic layer was separated and washed with water (50 mL) and brine (50 mL). The organic layer was dried, filtrated and then concentrated resulting in compound 51 (15 g), which was used without further purification in the next step.

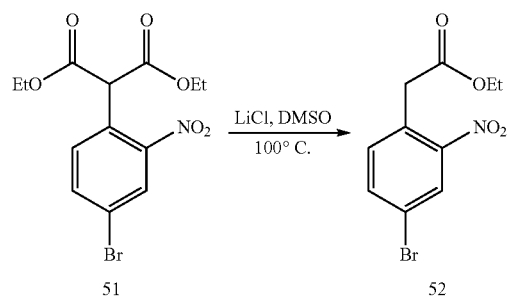 [SMILES: CCOC(=O)C(C(=O)OCC)c1ccc(Br)cc1[N+](=O)[O-] ; CCOC(=O)Cc1ccc(Br)cc1[N+](=O)[O-]]

Crude compound 51 (15 g) was dissolved in DMSO (100 mL). LiCl (3.0 g, 70 mmol) and H₂O (0.64 g, 35.6 mmol) were added and the reaction was heated to 100° C. for 3 hours. The reaction was cooled and poured into EtOAc (200 mL) and brine (200 mL). The phases were separated and the organic phase was washed with brine, dried over Na₂SO₄, and the filtrate was concentrated. The obtained residue was purified by silica gel chromatography (eluent: petroleum ether/ethyl acetate=50/1) resulting in product 52 (9.0 g).

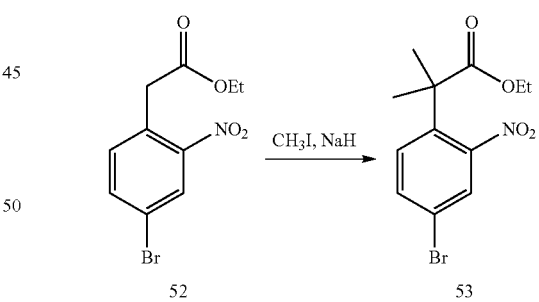

NaH (60%, 3.75 g, 93 mmol) was added to a stirred suspension of compound 52 (8.0 g, 27.8 mmol) in DMF (90 mL) at room temperature. After 15 minutes, MeI (22.2 g, 156 mmol) was added. The reaction mixture was stirred at room temperature overnight.

The mixture was poured into ice water (200 mL) and EtOAc (200 mL). The organic layer was washed with water (3×200 mL), brine, dried, and concentrated. The residue was purified by silica gel chromatography (eluent: petroleum ether/ethyl acetate=200:1) resulting in compound 53 (7.0 g., 80% yield).

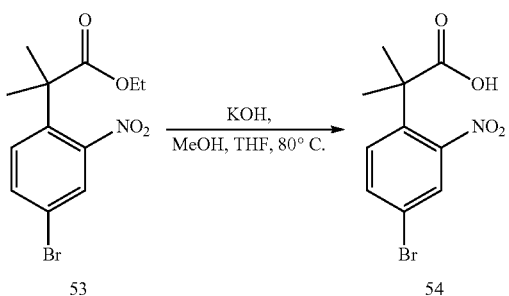 [SMILES: CCOC(=O)C(C)(C)c1ccc(Br)cc1[N+](=O)[O-] ; CC(C)(C(=O)O)c1ccc(Br)cc1[N+](=O)[O-]]

To compound 53 (7.0 g, 22.1 mmol), dissolved in MeOH (80 mL) and THF (40 mL), KOH (2 M, 80 mL, 160 mmol, 2.7 equiv.) was added. The reaction mixture was heated to 80° C. for 5 hours and then concentrated in vacuo. The residue was diluted with water (50 mL), and washed with methyl-t-butyl ether (50 mL). The aqueous layer was acidified to pH 2 by addition of 6 M HCl and then extracted with EtOAc (3×50 mL). The organic layer was washed with brine, dried and concentrated, resulting in compound 54 (5.0 g, 79%).

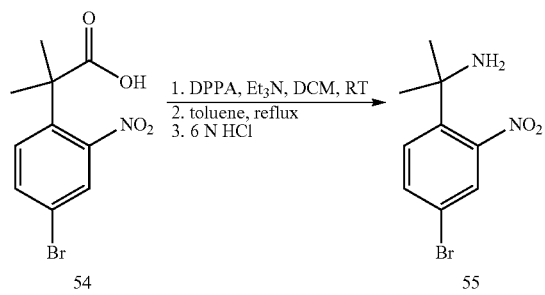

Compound 54 (8.8 g, 30.5 mmol) was dissolved in CH$_2$Cl$_2$ (200 mL) under N$_2$. After addition of triethylamine (4.01 g, 39.6 mmol.), the mixture was stirred at room temperature for 15 minutes. Diphenylphosphoryl azide (DPPA) (11 g, 40.0 mmol,) was added and the reaction mixture was stirred at room temperature for 3 hours. After removal of the volatiles in vacuo, the obtained residue was diluted with toluene (200 mL) and the mixture was heated at reflux for 2 hours. The reaction mixture was cooled to room temperature and HCl (6 M, 100 mL) was added. The resulting solution was heated at reflux for 3 hours. The crude mixture was concentrated in vacuum, diluted with ice water and basified with aq. NaOH(5 M), extracted with EtOAc (500 mL), washed with brine and dried over NaSO$_4$, then concentrated in vacuum. The residue was purified by chromatography (petroleum ether: ethyl acetate=10:1) resulting in compound 55 (7.1 g, 89%).

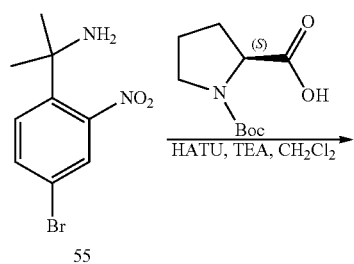

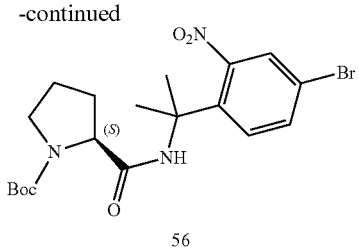

(S)-1-(tert-butoxycarbonyl)pyrrolidine-2-carboxylic acid (6.42 g, 29.8 mmol) was dissolved in dichloromethane (150 mL), HATU (20.6 g, 54.2 mmol) and triethylamine (8.22 g, 81.4 mmol.) were added. The resulting solution was stirred at room temperature for 15 minutes, then compound 55 (7.1 g, 27.4 mmol) was added. The reaction mixture was stirred at room temperature for 1 hour, and then water (150 mL) was added. The organic layer was separated, washed with brine, dried, and after filtration, concentrated in vacuo. The obtained residue was purified by silica gel column chromatography (petroleum ether:ethyl acetate=20:1) resulting in compound 56 (8.9 g, 72%). Method A2; Rt: 1.30 min. m/z=: 477.9 (M+Na)$^+$ Exact mass: 455.1

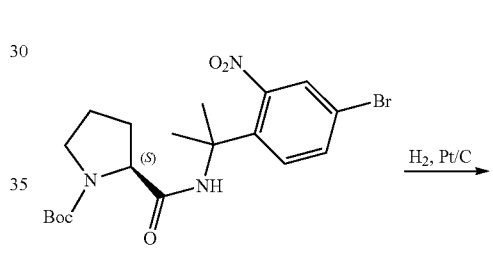

The compound 56 (8.9 g, 19.5 mmol) was dissolved in MeOH (50 mL), Pt/C (1.0 g) was added and the mixture was stirred under H$_2$ (20 PSI) overnight. Filtration and removal of the volatiles resulted in compound 57 (8.3 g, 100%)

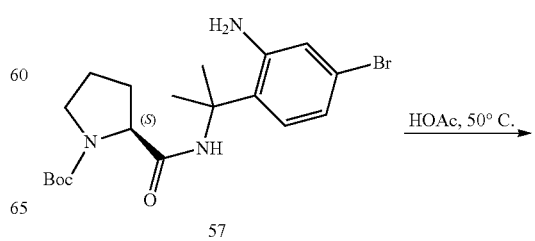

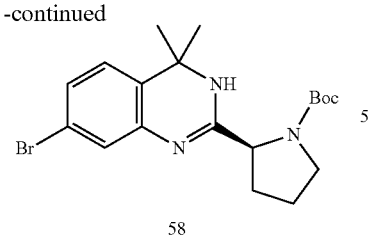

58

Compound 57 (8.3 g, 19.5 mmol) was dissolved in HOAc (100 mL). The reaction mixture was heated to 50° C. for 1 hour and then concentrated in vacuo. The obtained residue was purified by silicagel column chromatography (petroleum ether:ethyl acetate=7:1) resulting in compound 58 (1.5 g).
$[\alpha]_{589}^{20}$=−93.12 (CH$_3$OH, 2.50 mg/mL)
Method G1; Rt: 1.19 min. m/z=: 408.1 (M+H)$^+$ Exact mass: 407.1

Method A2; Rt: 1.01 min. m/z=: 691.5 (M+H)$^+$ Exact mass: 690.4

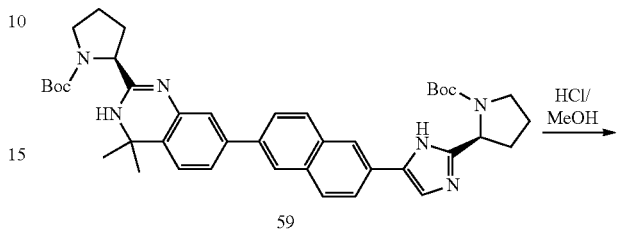

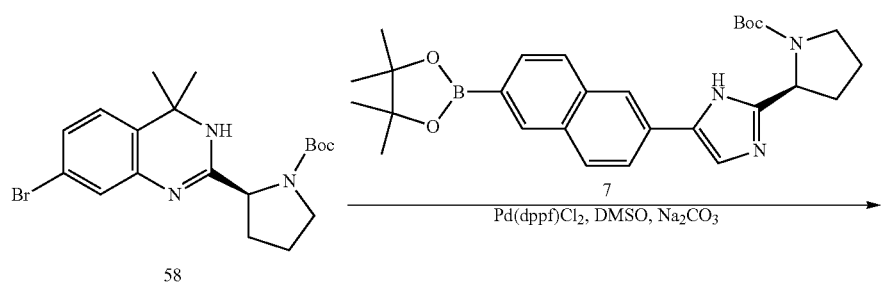

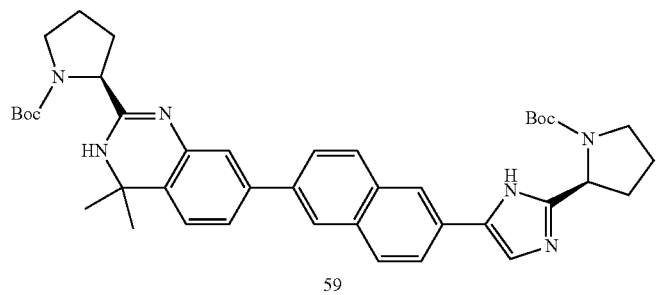

To a stirred mixture of compound 58 (730 mg, 1.79 mmol) in DMSO (10 mL) was added compound 7 (1.05 g, 2.15 mmol) and a solution of Na$_2$CO$_3$ (2 M, 2.68 mL,) and then added Pd(dppf)Cl$_2$ (105 mg, 0.143 mmol) under N$_2$ at room temperature. After the addition, the mixture was stirred at 60-70° C. for 1 hour. After completing, dichloromethane (50 mL) was added and the mixture was washed with water (3×100-mL) and brine. The organic layer were dried over Na$_2$SO$_4$ and concentrated in vacuo. The residue was purified over silica gel on thin layer chromatography (eluent: petroleum ether/ethyl acetate=1/100) resulting in compound 59 (778 mg; 63%).

-continued

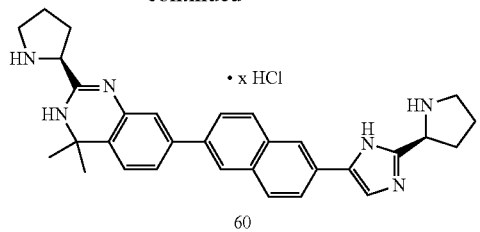

60

To the solution of compound 59 (500 mg, 0.72 mmol) was added methanol/HCl (10 mL) at room temperature. The mixture was stirred for 1 hour at room temperature. The mixture was washed by methyl-t-butyl ether (20 mL) and filtrated resulting in compound 60 (355 mg, 99%). Method A2; Rt: 0.81 min. m/z=: 491.1 (M+H)$^+$ Exact mass: 490.3

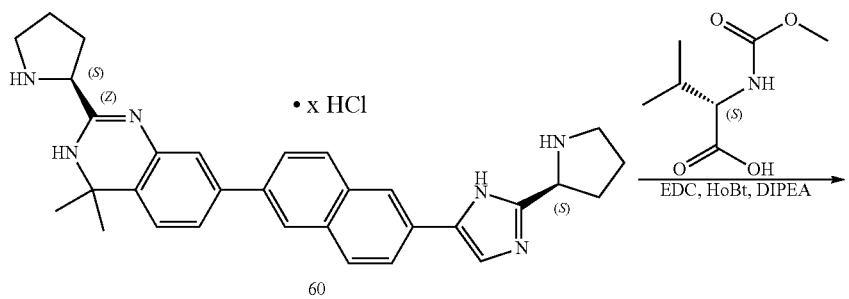

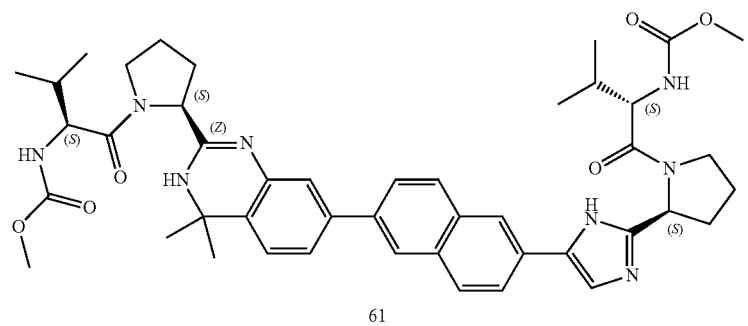

To a solution of compound 60 (355 mg, 0.72 mmol) in CH₃CN (30 mL), HOBt (234 mg, 1.73 mmol), EDC (333 mg, 1.73 mmol), (S)-2-(methoxycarbonylamino)-3-methylbutanoic acid (304 mg, 1.73 mmol) and diisopropylethylamine (560 mg, 4.34 mmol) were added at room temperature under N₂. After conversion to compound 61, the mixture was diluted with CH₂Cl₂ (50 mL) and was washed with aqueous NaOH (0.5 N, 50 mL) and brine. The organic layer was dried and after filtration, concentrated in vacuo. The obtained crude product was purified by high-performance liquid chromatography (Phenomenex Gemini C18 150*30 mm*5 um (eluent: (0.05% NH₃ in H₂O)/CH₃CN 44/64 v/v)) resulting in compound 61 (231 mg, 40% yield).

Method C; Rt: 3.53 min. m/z=: 805.4 (M+H)⁺ Exact mass: 804.4

[α]$_{589}^{20}$=−146.67 (CH₃OH, 1.07 mg/mL)

SFC: Columns: Chiralcel OD-H 150 mm*4.6 mm; 5 um; Flow: 2.35 mL/min; Mobile phase: A: CO₂ B: EtOH (0.05% Diethylamine); 5 to 40% B in A,: Rt: 9.10 min SFC: Columns: Chiralcel OJ-H 250 mm*4.6 mm; 5 um; Flow: 2.35 mL/min; Mobile phase: A: CO₂ B: EtOH (0.05% Diethylamine); 5 to 40% B in A,: Rt: 7.71 min.

¹H NMR (600 MHz, DMF+droplet TFA) δ ppm 0.87 (d, J=6.7 Hz, 3 H), 0.93 (d, J=6.7 Hz, 3 H), 0.95 (d, J=6.7 Hz, 3 H), 1.00 (d, J=6.9 Hz, 3 H), 1.77 (s, 3 H), 1.85 (s, 3 H), 2.05-2.16 (m, 2 H), 2.17-2.38 (m, 6 H), 2.48-2.59 (m, 2 H), 3.62 (s, 3 H), 3.62 (s, 3 H), 3.91 (dd, J=12.8, 8.6 Hz, 1 H), 3.96-4.01 (m, 1 H), 4.01-4.07 (m, 2 H), 4.32 (dd, J=8.5, 6.7 Hz, 2 H), 4.85 (t, J=7.8 Hz, 1 H), 5.42 (dd, J=7.8, 6.5 Hz, 1 H), 7.07 (d, J=8.7 Hz, 1 H), 7.17 (d, J=8.8 Hz, 1 H), 7.70 (d, J=8.2 Hz, 1 H), 7.84 (dd, J=8.1, 1.8 Hz, 1 H), 7.89 (d, J=1.2 Hz, 1 H), 7.96 (dd, J=8.7, 1.8 Hz, 1 H), 8.08 (dd, J=8.7, 1.8 Hz, 1 H), 8.10 (d, J=8.7 Hz, 1 H), 8.13 (d, J=8.4 Hz, 1 H), 8.21 (s, 1 H), 8.34 (s, 1 H), 8.58 (s, 1 H), 10.76 (br. s., 1 H), 12.83 (br. s., 1 H)

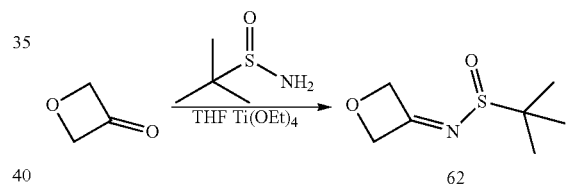

To Oxetan-3-one (5 g, 69 mmol) in THF (50 mL) 2-methylpropane-2-sulfinamide (8.34 g, 69 mmol) and Ti(OEt)₄ (20 mL) were added sequentially. The reaction was heated to 50° C. for 5 hours. The reaction was cooled to room temperature and quenched with water (200 mL). The precipitate was filtered and the filtrate was extracted with CH₂Cl₂ (2×50 mL). The combined organic layer was separated and washed with water (50 mL) and brine (50 mL). The organic layer was dried and concentrated. The crude product was purified by column chromatography (CH₂Cl₂) to afford compound 62 (5.5 g, 46% yield).

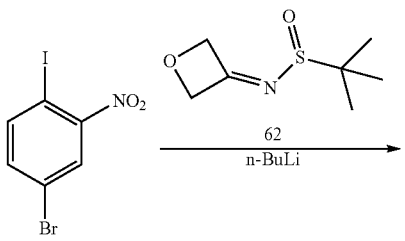

-continued

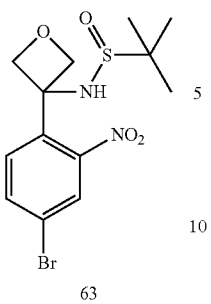

63

4-bromo-1-iodo-2-nitrobenzene (3 g, 9.18 mmol) was dissolved in anhydrous THF (20 mL) under N₂ atmosphere, and the flask was cooled to −78° C. The mixture was stirred for 5 minutes and n-BuLi (4.4 mL, 2.5 mol/L) was slowly added. The reaction mixture turned dark and stirring was continued at −78° C. for 15 minutes. Then, compound 62 (1.92 g, 11 mmol) was slowly added to the mixture. The reaction was stirred for 30 minutes at −78° C. and then warmed to room temperature. The mixture was poured into water (50 mL) and extracted with CH₂Cl₂ (2×20 mL). The organic phases were separated and washed with brine, dried over Na₂SO₄ and concentrated to dryness. The resulting residue was purified by silica gel column chromatography (eluent: petroleum ether/ethyl acetate=3/1), resulting in compound 63 (1.3 g, 38% yield).

Method A2; Rt: 1.04 min. m/z=: 378.7 (M+H)⁺ Exact mass: 378.0

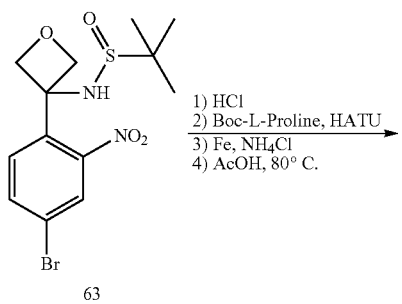

-continued

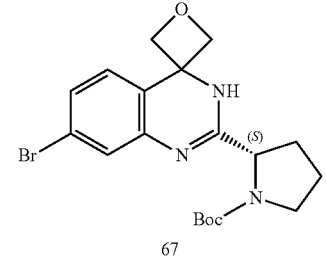

67

Compound 63 (1.3 g, 3.45 mmol) was dissolved in MeOH (10 mL) and HCl/dioxane (4N, 10 mL) was slowly added. The reaction was stirred at room temperature for 30 minutes and the mixture was concentrated, resulting in intermediate 64 (0.89 g).

Method A2; Rt: 0.60 min. m/z=: 272.7 (M+H)⁺ To intermediate 64 (0.89 g) in a 50 mL flask, HATU (1.49 g, 3.94 mmol), triethylamine (0.66 g, 6.56 mmol) and (S)-1-(tert-butoxycarbonyl)pyrrolidine-2-carboxylic acid (0.84 g, 3.94 mmol,) were added. The residue was dissolved in CH₂Cl₂ (10 mL). The reaction mixture was stirred at room temperature for 40 minutes. The mixture was quenched with water (20 mL) and extracted with CH₂Cl₂ (2×10 mL). The phases were separated and the organic phase was washed with brine, dried over Na₂SO₄ and then concentrated. The obtained residue was purified by silica gel chromatography (eluent: petroleum ether/ethyl acetate=2/1) resulting in intermediate 65 (1.27 g). Intermediate 65 (1 g, 2.1 mmol) was dissolved in MeOH/water (20 mL 1:1), Fe powder (0.35 g, 6.3 mmol) and NH₄Cl (0.55 g, 10.5 mmol) were added and the mixture was stirred at reflux for 3 hours. The reaction mixture was cooled to room temperature and then concentrated to dryness. The obtained residue was washed with water (10 mL), and extracted with CH₂Cl₂ (2×10 mL). The organic layer was separated and concentrated in vacuo, resulting in intermediate 66 (0.77 g). Method A2; Rt: 1.07 min. m/z=: 464.0 (M+Na)⁺ Exact mass: 441.1. Intermediate 66 (0.77 g, 1.75 mmol) was dissolved in AcOH (20 mL). The resulting solution was stirred at 80° C. for 30 minutes. The reaction mixture was concentrated under vacuum and the resulting residue was purified by column chromatography (petroleum ether:ethyl acetate=1:1) resulting in compound 67 (0.49 g, 66%). Method B; Rt: 4.06 min. m/z=: 422.0 (M+H)⁺ Exact mass: 421.1

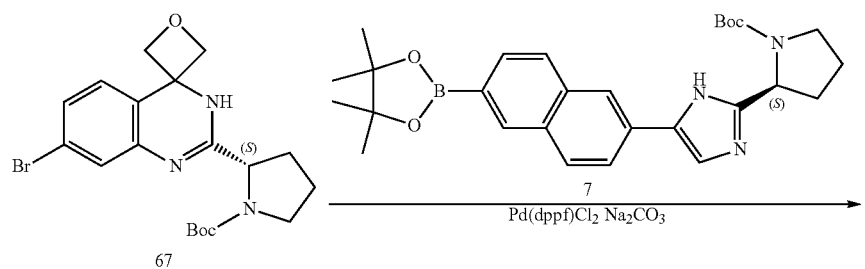

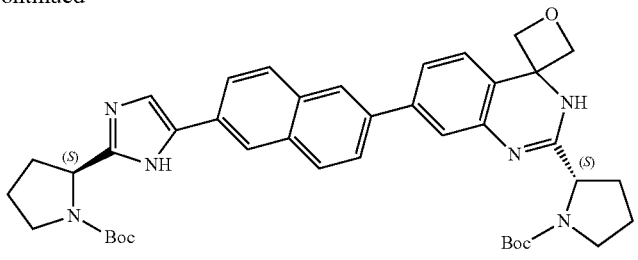

68

To a 20 mL flask containing compound 67 (0.49 g, 1.16 mmol), compound 7 (0.68 g, 1.4 mmol,) and Pd(dppf)Cl₂ (45 mg, 0.058 mmol), THF (10 mL) and aqueous Na₂CO₃ (2 mL, 2 N) were added. The mixture was flushed three times with nitrogen gas. The reaction mixture was stirred at 80° C. for 15 minutes. The mixture was quenched with water (10 mL) and extracted with CH₂Cl₂ (2×5 mL). The phases were separated, the organic phase was washed with brine, dried over Na₂SO₄, and concentrated. The obtained residue was purified by column chromatography on silica (eluent: CH₂Cl₂/methanol=10/1) resulting in compound 68 (0.37 g, 45%). Method A2; Rt: 0.92 min. m/z=: 705.4 (M+H)⁺ Exact mass: 704.4

-continued

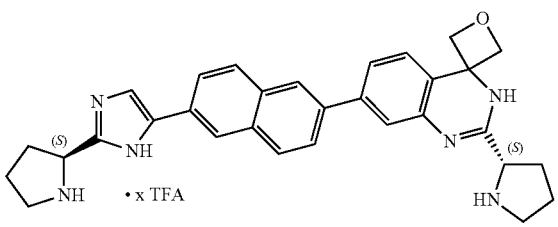

69

Compound 68 (0.2 g, 0.28 mmol) was dissolved in CH₂Cl₂ (5 mL) and TFA (5 mL) was slowly added. The reaction was stirred at room temperature for 30 minutes and the mixture was concentrated in vacuo, resulting in compound 69.

Method A2; Rt: 0.77 min. m/z=: 505.1 (M+H)⁺ Exact mass: 504.3

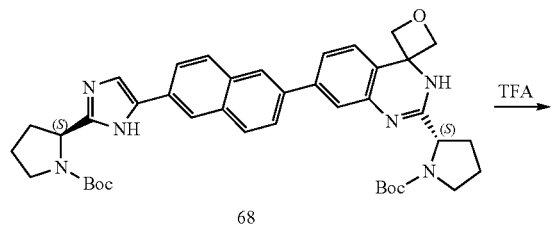

68

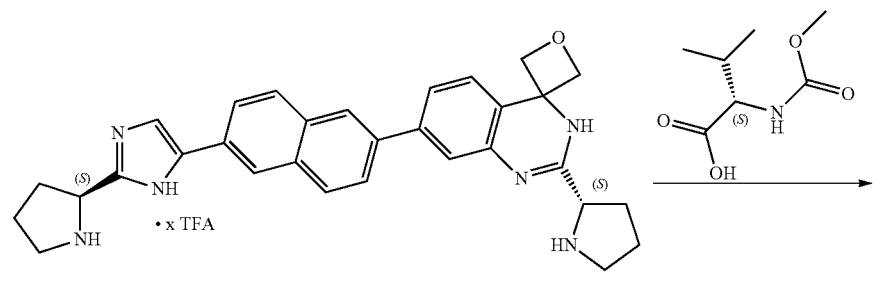

69

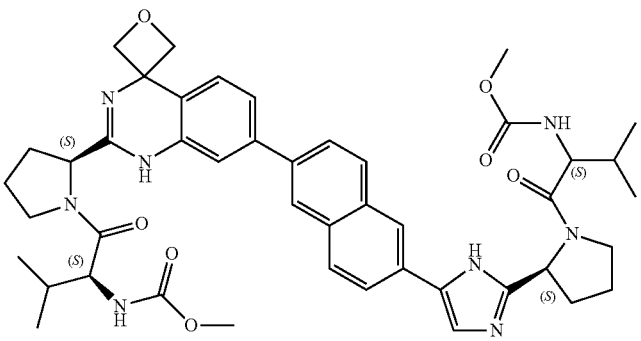

70

To a solution of compound 69 (200 mg) in CH$_2$Cl$_2$ (10 mL), (S)-2-(methoxycarbonyl-amino)-3-methylbutanoic acid (140 mg, 0.80 mmol), EDC (170 mg, 0.94 mmol), HOBt (10 mg, 0.076 mmol) and triethylamine (154 mg, 1.52 mmol) were added. The mixture was stirred at room temperature overnight. The mixture was washed with water (10 mL) and extracted with CH$_2$Cl$_2$ (2×10 mL). The combined organic layer was dried and concentrated and the obtained residue was purified by high-performance liquid chromatography (YMC-pack ODS-AQ 150×30 mm×5 um Mobile phase: A: water+0.1% TFA B: acetonitrile. Elute from 26% B to 52% B in A for total 15 min. Flow rate: 25mL/min). To the appropriate fractions, Na$_2$CO$_3$ was added until pH value was 9. The solution was concentrated to remove acetonitrile and the mixture was extracted with CH$_2$Cl$_2$ (2×20 mL). The organic layer was separated and concentrated to dryness to afford the compound 70 (92 mg).

Method C; Rt: 3.37 min. m/z=: 819.4 (M+H)$^+$ Exact mass: 818.4

SFC: Columns: Chiralcel OD-3 150 mm*4.6 mm; 3 um; Flow: 2.5 mL/min; Mobile phase: A: CO$_2$ B: MeOH (0.05% Diethylamine); 40% B in A,: Rt: 5.66 min SFC: Columns: Chiralcel OJ-H 250 mm*4.6 mm; 5 um; Flow: 2.5 mL/min; Mobile phase: A: CO$_2$ B: MeOH (0.05% Diethylamine); 40% B in A,: Rt: 3.44 min.

$^1$H NMR (600 MHz, DMF-d$_7$+droplet TFA) δ ppm 0.87 (d, J=6.7 Hz, 3 H), 0.93 (d, J=6.7 Hz, 3 H), 0.95 (d, J=6.9 Hz, 3 H), 1.00 (d, J=6.7 Hz, 3 H), 2.07-2.16 (m, 2 H), 2.18-2.25 (m, 1 H), 2.26-2.37 (m, 4 H), 2.37-2.43 (m, 1 H), 2.49-2.58 (m, 2 H), 3.62 (s, 3 H), 3.63 (s, 3 H), 3.91 (dd, J=14.2, 8.0 Hz, 1 H), 3.96-4.12 (m, 3 H), 4.32 (dd, J=8.4, 6.9 Hz, 1 H), 4.35 (dd, J=8.6, 6.7 Hz, 1 H), 4.91 (t, J=8.1 Hz, 1 H), 4.98 (d, J=7.2 Hz, 1 H), 5.00 (d, J=7.3 Hz, 1 H), 5.10 (d, J=7.2 Hz, 1 H), 5.24 (d, J=7.3 Hz, 1 H), 5.42 (dd, J=7.8, 6.5 Hz, 1 H), 7.08 (d, J=8.7 Hz, 1 H), 7.19 (d, J=8.8 Hz, 1 H), 7.94 (d, J=1.2 Hz, 1 H), 7.99 (dd, J=8.5, 1.8 Hz, 1 H), 8.00 (dd, J=8.1, 1.8 Hz, 1 H), 8.09 (dd, J=8.7, 1.8 Hz, 1 H), 8.10 (d, J=8.1 Hz, 1 H), 8.12 (d, J=8.7 Hz, 1 H), 8.15 (d, J=8.7 Hz, 1 H), 8.23 (s, 1 H), 8.38 (s, 1 H), 8.59 (s, 1 H), 11.64 (br. s., 1 H), 13.33 (br. s., 1 H)

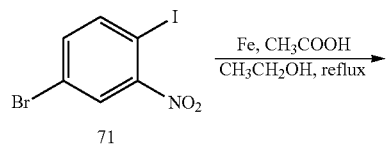

71

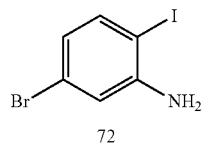

72

A mixture of compound 71 (6.5 g, 19.8 mmol) and Fe (4.98 g, 89.2 mmol) in CH$_3$COOH (30 mL) and CH$_3$CH$_2$OH (30 mL), was refluxed for 1.5 hours. The mixture was cooled to room temperature and after addition of saturated NaHCO$_3$ (aq.), extracted with ethyl acetate (3×150 mL). The combined organic layer was separated, dried over Na$_2$SO$_4$ and the solvent was removed in vacuo, resulting in compound 72 (5.9 g).

Method A2; Rt: 1.17 min. m/z=: 299.6 (M+H)$^+$ Exact mass: 298.9

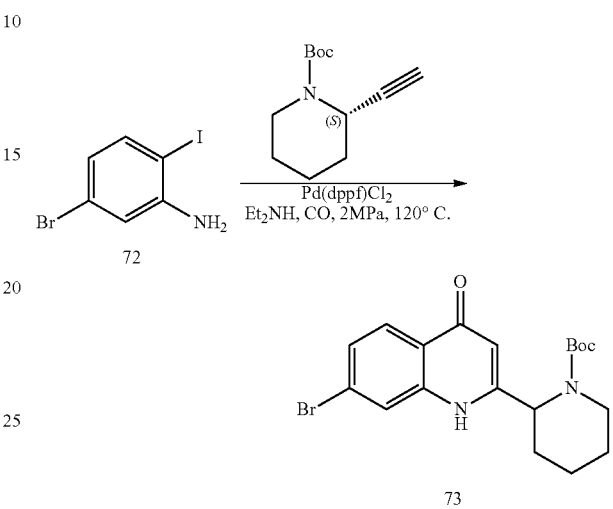

73

The mixture of compound 72 (2.0 g, 6.7 mmol), 2-ethynyl-piperidine-1-carboxylic acid tert-butyl ester (2.8 g, 13.4 mmol) and Pd(dppf)Cl$_2$ (0.245 g, 0.335 mmol) in diethylamine (30 mL) was stirred under carbon monoxide at the pressure of 2 MPa. at 120° C. After 6 hours, the mixture was concentrated under reduce pressure. The residue was dissolved in CH$_2$Cl$_2$ (50 mL) and washed with brine (2×20 mL). Then, the organic layer was dried over Na$_2$SO$_4$ and concentrated. The residue was purified by silica gel chromatography (eluent: petroleum ether/ethyl acetate=30/1 to 1/30). The desired section was collected and concentrated. The residue was triturated by CH$_3$OH and the solid (impurity) was removed by filtration. The filtrate was concentrated and the obtained residue was purified by high-performance liquid chromatography (eluent: CH$_3$CN/H$_2$O=30/70 to 60/40, 0.05% trifluoroacetic acid). Then the pH of the solution was adjusted to about 7-8 with NaHCO$_3$ and acetonitrile was removed under reduced pressure. The aqueous layer was extracted with CH$_2$Cl$_2$ (3×50 mL) and the organic layers were combined and dried on Na$_2$SO$_4$. After filtration, the filtrate was evaporated and the obtained residue was dried under vacuum resulting in compound 73 (0.21 g, 8% yield).

Method A2; Rt: 1.10 min. m/z=: 408.9 (M+H)$^+$ Exact mass: 408.1

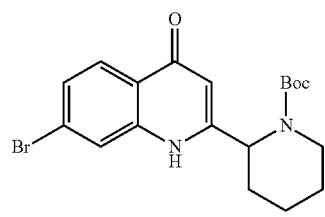

73

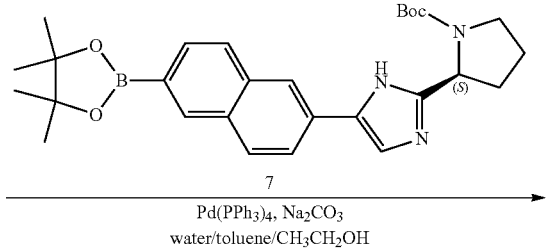

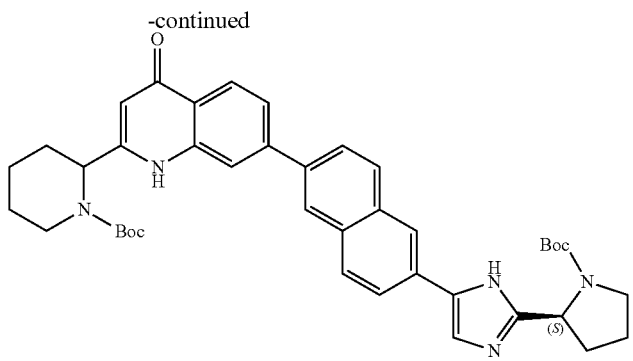

74

Pd(PPh$_3$)$_4$ (59 mg, 0.051 mmol) was added to the mixture of compound 73 (0.21 g, 0.51 mmol), compound 7 (0.25 g, 0.51 mmol), Na$_2$CO$_3$/H$_2$O (0.11 g, 1 mL), toluene (2 mL) and CH$_3$CH$_2$OH (1 mL) in one portion under nitrogen. The mixture was stirred for 10 hours at 90° C. Then the solution was cooled to room temperature and filtered. The filtrate was concentrated in vacuo. The obtained residue was dissolved in CH$_2$Cl$_2$ (20 mL) and washed with water (3×5 mL). The organic fractions was dried over Na$_2$SO$_4$ and concentrated under reduced pressure. The obtained residue was purified by high-performance liquid chromatography (eluent: CH$_3$CN/ H$_2$O=30/70 to 60/40, 0.05% trifluoroacetic acid). The pH of the obtained solution was adjusted to about 7-8 with NaHCO$_3$ and acetonitrile was removed under reduced pressure. The aqueous layer was extracted with CH$_2$Cl$_2$ (3×50 mL) and the organic layers were combined and dried with Na$_2$SO$_4$. After filtration, the filtrate was concentrated in vacuo, resulting in compound 74 (0.11 g, 31%).

Method A2; Rt: 1.02 min. m/z=: 690.4 (M+H)$^+$ Exact mass: 689.4

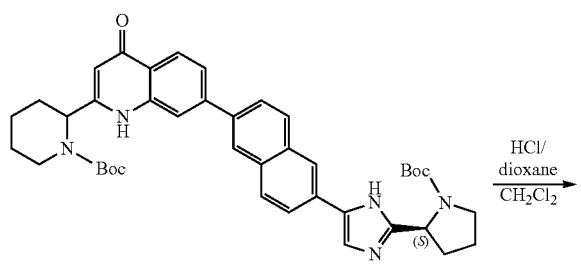

74

-continued

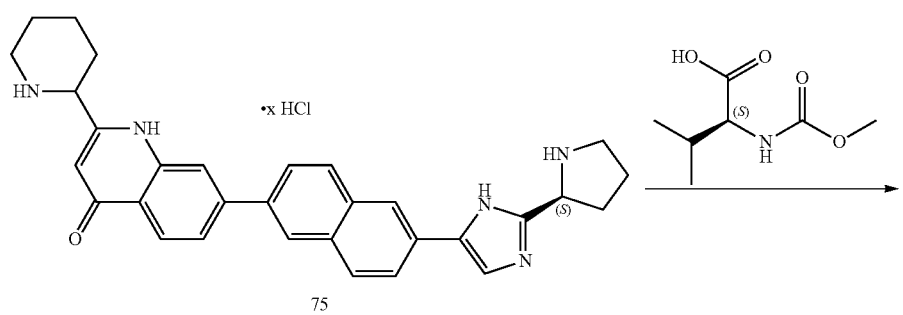

75

4N HCl/dioxane (0.16 mL, 0.64 mmol) was added to the solution of compound 74 (0.11 g, 0.16 mmol) in CH$_2$Cl$_2$ (2 mL) at 0° C. The mixture was then stirred at room temperature for 1 hour. The formed precipitate was filtered and the cake was washed with methyl tert-butyl ether (2×10 mL) to obtain the crude compound 75 (78 mg).

Method A2; Rt: 0.76 min. m/z=: 490.2 (M+H)$^+$ Exact mass: 489.3

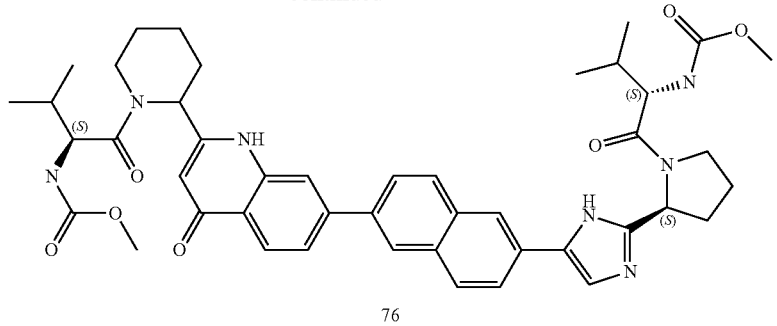

76

To a solution of (S)-2-(methoxycarbonylamino)-3-methylbutanoic acid (84 mg, 0.48 mmol) in acetonitrile (3 mL) was added EDC.HCl (122.7 mg, 0.64 mmol) and HOBt (86.5 mg, 0.64 mmol). The mixture was stirred at 20° C. for 1 hour. Then compound 75 (78 mg) was added. The resulting slurry was cooled to 0° C. and diisopropylethylamine (103.4 mg, 0.8 mmol) was added. The mixture was stirred at room temperature for 15 hours. The mixture was concentrated and then diluted with $CH_2Cl_2$ (20 mL) and 0.5 N NaOH (aq.) (5 mL). The organic layer was separated and washed with 13% aqueous NaCl (3×10 mL). The solvent was removed and the obtained residue was purified by preparative high-performance liquid chromatography (eluent: $CH_3CN/H_2O$=30/70 to 60/40, 0.1% $CF_3COOH$). The desired fraction was collected and the pH of the solution was adjusted to about 6 with citric acid (0.5 N, aq.). Then the acetonitrile was removed under reduced pressure. The aqueous layer was extracted with $CH_2Cl_2$ (3×50 mL) and the organic layers were combined and dried on $Na_2SO_4$. After filtration, the solvent was removed and the residue was dried in vacuo, resulting in compound 76 (33 mg).

Method B; Rt: 5.11 min and 5.03 min. m/z=: 804.2 (M+H)$^+$
Exact mass: 803.4

SFC: Columns: Chiralcel OJ-H 250 mm*4.6 mm; 5 um; Flow: 2 mL/min; Mobile phase: A: $CO_2$ B: MeOH (0.05% Diethylamine); 30% B in A,: Rt: 3.71 min and 4.87 min.

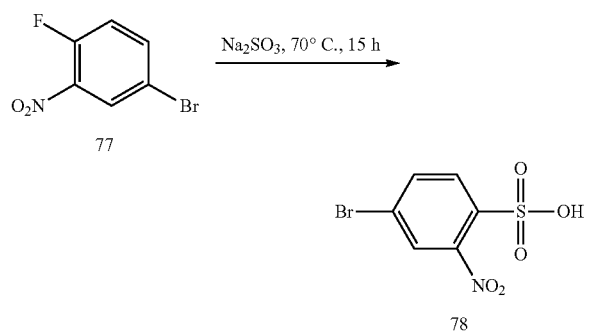

Compound 77 (50 g, 227 mmol) was dissolved in ethanol (600 mL). Subsequently, a suspension of $Na_2SO_3$ (71.6 g, 568 mmol) in ethanol (1000 mL) and water (1250 mL) was added. The suspension was stirred at 70° C. for 15 hours. Then, at room temperature, the reaction mixture was acidified with HCl (2N) to pH=2 and concentrated in vacuo. The remaining residue was dissolved under reflux in brine (1000 mL). Subsequently, water (100 mL) was added and the solution was cooled in an ice bath. The precipitate was collected by filtration, resulting in compound 78 (57.3 g, 89%).

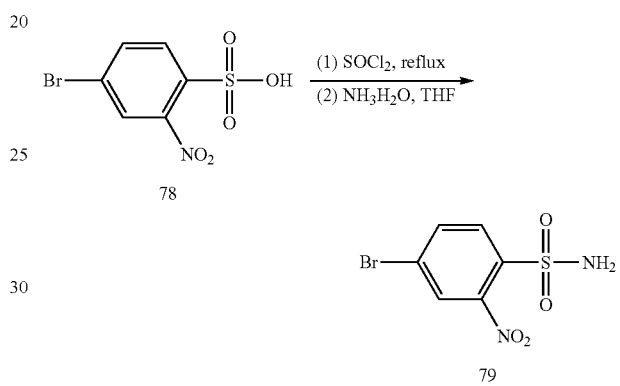

To a solution of thionyl chloride (50 mL) was added compound 78 (30 g, 106 mmol) and DMF (1 drop) and the reaction mixture was heated to reflux for 4 hours. Upon cooling, the reaction mixture was azeotroped with toluene for three times. The residue was dissolved in a minimal amount of toluene and then the resulting mixture was added to a mixture of concentrated aqueous ammonium hydroxide solution (1 mL) and THF (10 mL) at −10° C. After stirring for 2 hours the reaction was quenched by adding a solution of 6 M aqueous hydrochloric acid until pH=4. The organic layer was separated and then dried and concentrated in vacuo. Petroleum ether was added to the resulting slurry and the product was collected by vacuum filtration to afford compound 79.

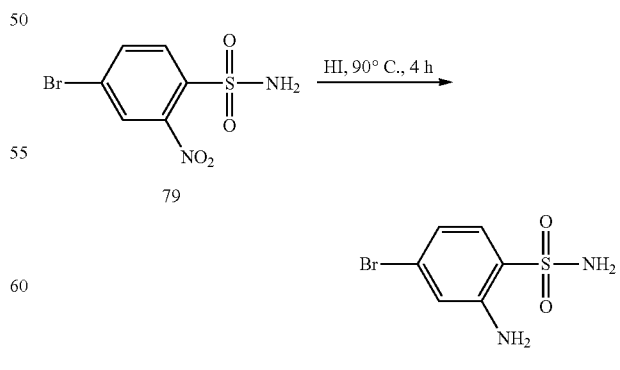

A suspension of compound 79 (21.2 g, 75 mmol) in 57% HI (250 mL) was heated at 90° C. for 4 hours. After cooling to room temperature, the dark purple mixture was diluted with ethyl acetate (500 mL) and next washed successively by saturated aq Na$_2$S$_2$O$_3$, saturated aq NaHCO$_3$ and brine. The colorless organic layer was dried on anhydrous MgSO$_4$, filtrated and concentrated to dryness. The crude product was purified by high-performance liquid chromatography (eluent: CH$_3$CN/H$_2$O from 22/78 to 52/48 with 0.01% NH$_3$H$_2$O as buffer). Resulting in compound 80 (18.6 g).

Method B; Rt: 3.36 min. m/z=: 250.9 (M+H)$^+$ Exact mass: 249.9

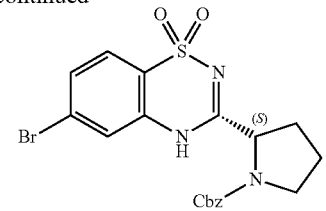

81

Triethylamine (40.5 mL, 296 mmol) was added to a solution of compound 80 (18.6 g, 74 mmol) in acetone (200 mL). Compound 29 (12.8 g, 48 mmol) was added to the reaction mixture under cooling. After stirring for 5 hours, the reaction mixture was diluted with water and acidified by 2 N HCl to pH 4. The resulting precipitate was collected by filtration and then transferred to another flask. A solution of K$_2$CO$_3$ (15 g) in water (100 mL) was added and the reaction mixture was reflux for 2 hours until the reaction became homogeneous. The reaction mixture was acidified by 2 N HCl until pH=4. The precipitate was filtered off and washed with water. The crude product was purified by high performance liquid chromatography (eluent: CH$_3$CN/H$_2$O from 35/65 to 65/35 with 0.75% CF$_3$COOH as buffer), resulting in compound 81 (8.3 g, 45%)

Method A2; Rt: 1.05 min. m/z=: 487.8 (M+Na)$^+$ Exact mass: 465.0

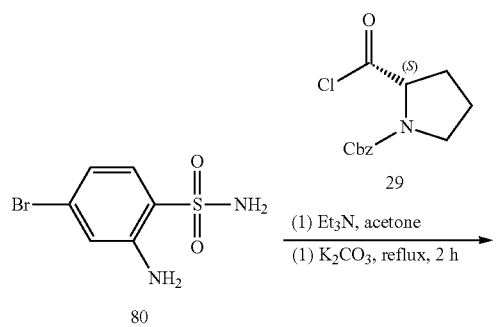

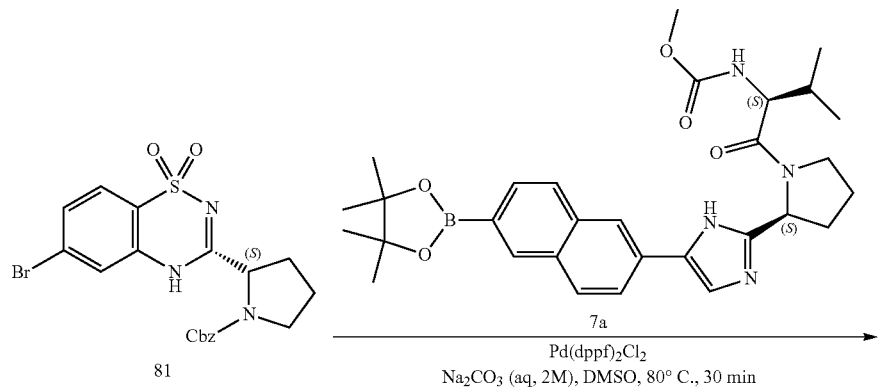

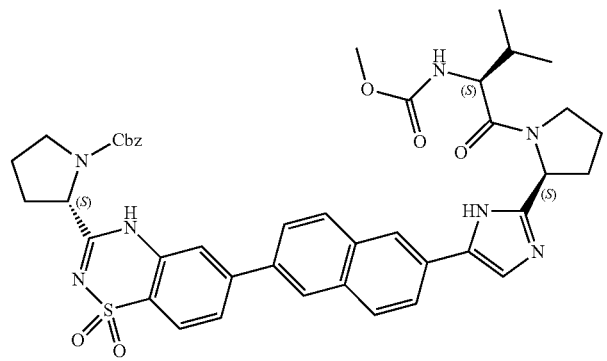

Pd(dppf)₂Cl₂ (140 mg) was added to a mixture of compound 81 (1 g, 2.1 mmol), and compound 7a (1.4 g, 2.5 mmol) in a solution of aq. Na₂CO₃ (2 M, 4 mL) and DMSO (8 mL) under nitrogen. The mixture was stirred at 80° C. for 30 min. The mixture was concentrated and water (30 mL) was added. The resulting mixture was extracted with CH₂Cl₂ (3×80 mL). The combined organic layers were separated, dried on Na₂SO₄ and after filtration, the solvent was removed in vacuo. The resulting solid (1.75 g) was used directly in the next step. Method A2; Rt: 0.99 min. m/z=: 804.4 (M+H)⁺ Exact mass: 803.3

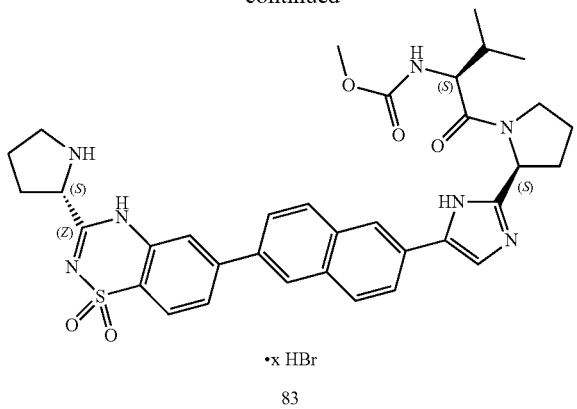

83 ·x HBr

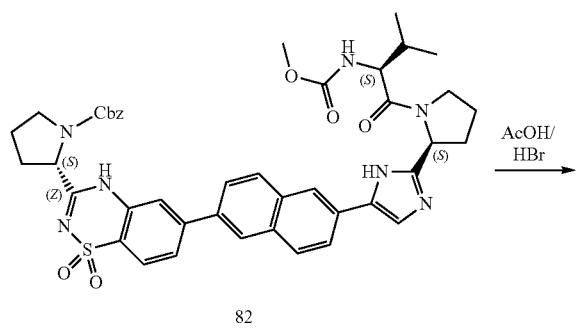

82

Compound 82 (1.5 g, 1.86 mmol) was dissolved in a mixture of AcOH (10 mL) and aq. HBr (5 mL). The mixture was stirred at 60° C. for 4 hours. The mixture was concentrated and the obtained residue was washed by acetonitrile. The resulting solid was filtered off to afford compound 83 as a HBr salt (0.9 g). Method A2; Rt: 0.94 min. m/z=: 670.3 (M+H)⁺ Exact mass: 669.3

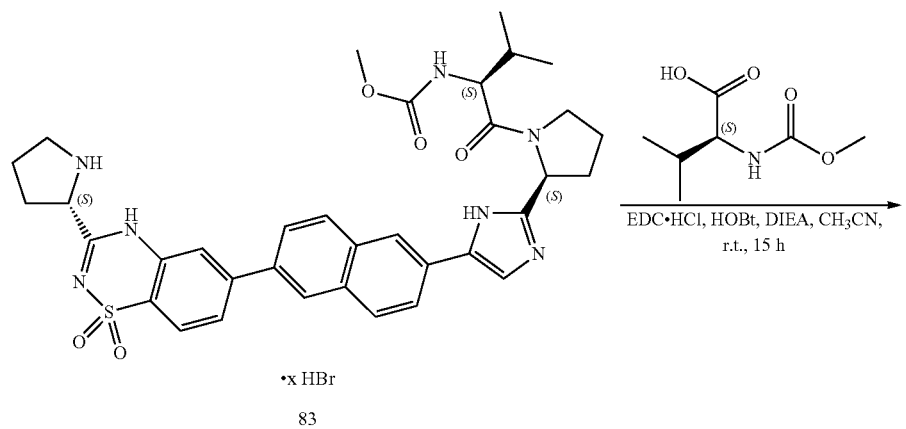

·x HBr

83

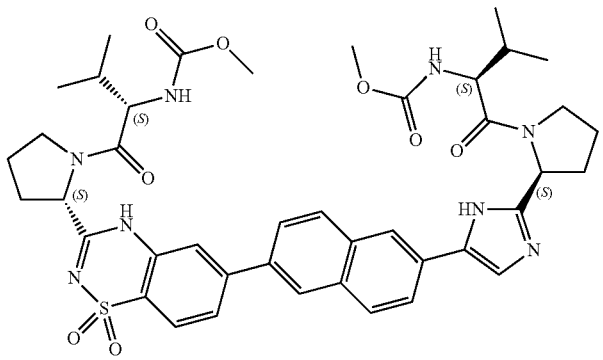

84

To a solution of (S)-2-(methoxycarbonylamino)-3-methylbutanoic acid (125 mg, 0.7 mmol) in CH$_3$CN (10 mL) EDC.HCl (137 mg, 0.7 mmol) and HOBt (97 mg, 0.7 mmol) were added. The mixture was stirred at 0° C. for 1 hour and compound 83 (0.4 g) was added. The slurry was cooled to 0° C., diisopropylethylamine (0.3 g, 2.3 mmol) was added and the mixture was further stirred at 20° C. for 15 hours. The volatiles were removed. The mixture was diluted with CH$_2$Cl$_2$ (30 mL) and 0.5 N NaOH (aq.) (15 mL), the organic layer was separated and then washed with brine (3×15 mL). The combined organic layer was dried on Na$_2$SO$_4$ and after filtration, concentrated. The obtained crude product was purified by high-performance liquid chromatography (eluent: CH$_3$CN/H$_2$O from 35/65 to 65/35 with 0.75% CF$_3$COOH as buffer). The desired fraction was collected and basified by saturated NaHCO$_3$ (aq.) till pH~8. The mixture was concentrated and then extracted with CH$_2$Cl$_2$ (3×100 mL). The organic layer was dried on Na$_2$SO$_4$ and the solvent was removed in vacuo resulting in compound 84 (86 mg).

Method B; Rt: 4.83 min. m/z=: 827.6 (M+H)$^+$ Exact mass: 826.4

SFC: Columns: Chiralcel AS-H 250 mm*4.6 mm; 5 um; Flow: 2.5 mL/min; Mobile phase: A: CO$_2$ B: MeOH (0.05% Diethylamine); 40% B in A,: Rt: 2.73 and 3.55 min SFC: Columns: Chiralcel OJ-H 250 mm*4.6 mm; 5 um; Flow: 2.5 mL/min; Mobile phase: A: CO$_2$ B: MeOH (0.05% Diethylamine); 40% B in A,: Rt: 2.58 and 3.05 min.

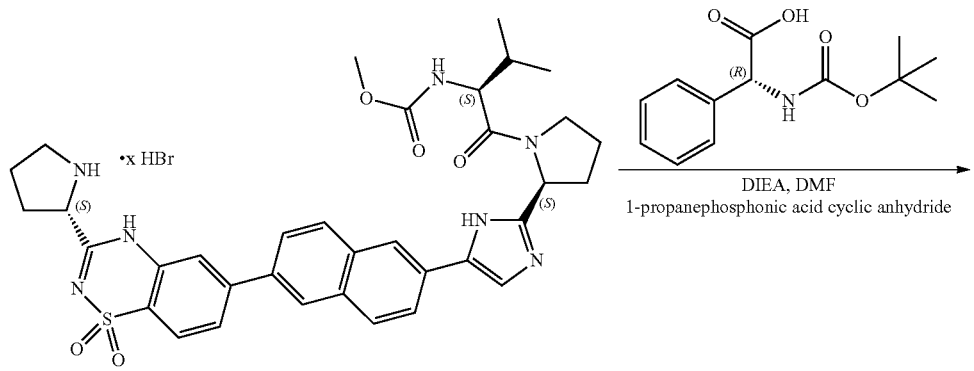

83

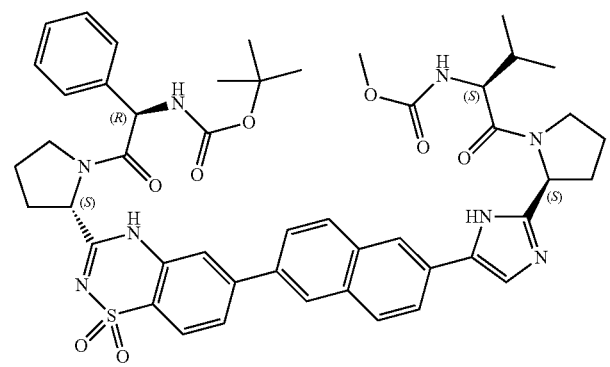

85

To a solution of compound 83 (1.2 g, 1.79 mmol) in DMF (15 mL) were added (R)-2-(tert-butoxycarbonylamino)-2-phenylacetic acid (0.54 g, 2.15 mmol), 1-propane-phosphonic acid cyclic anhydride and (3.8 mL, 6.62 mmol) and diisopropylethylamine (0.92 g, 7.16 mmol). The mixture was stirred at 20° C. for 15 hours. The mixture was concentrated and diluted with CH$_2$Cl$_2$ (50 mL) and 0.5 N NaOH (aq., 15 mL). The organic layer was separated and washed with brine (3×20 mL). The combined organic layer was dried on Na$_2$SO$_4$ and after filtration, concentrated in vacuo. The obtained crude product was purified by high-performance liquid chromatography (eluent: CH$_3$CN/H$_2$O from 32/68 to 62/38 with 0.75% CF$_3$COOH as buffer). The desired fraction was collected and basified by saturated NaHCO$_3$ (aq.) till pH~8. The mixture was concentrated and the resulting mixture was extracted with CH$_2$Cl$_2$ (3×100 mL). The organic layer was dried on Na$_2$SO$_4$ and the solvent was removed in vacuo resulting in compound 85 (750 mg).

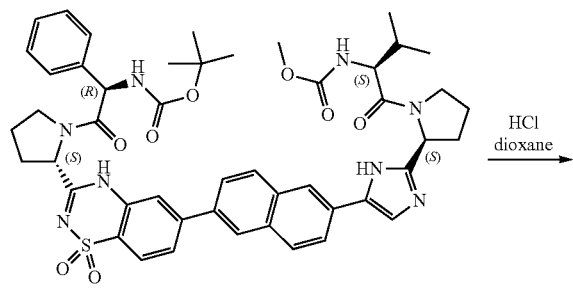

85

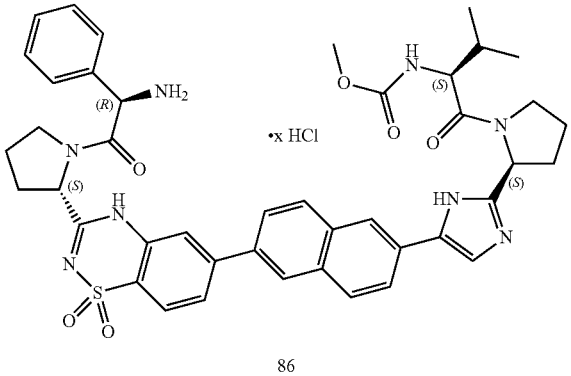

86

Compound 85 (600 mg, 0.66 mmol) was dissolved in HCl dioxane (10 mL). The mixture was stirred at 20° C. for 1.5 hours and concentrated, resulting in compound 86 (625 mg).

Method G1; Rt: 0.89 min. m/z=: 803.1 (M+H)$^+$ Exact mass: 802.3

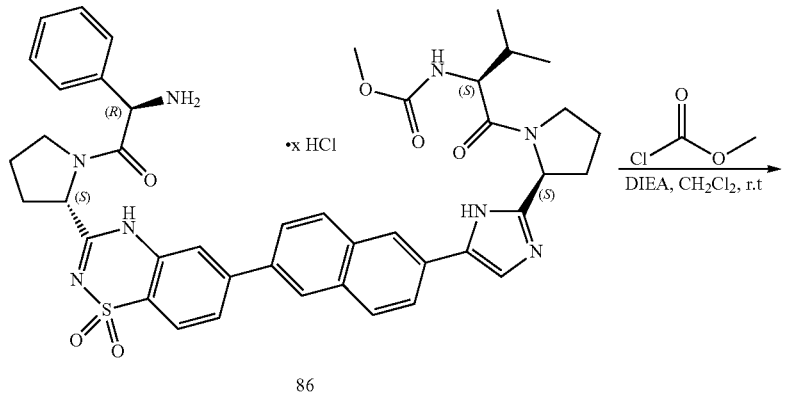

86

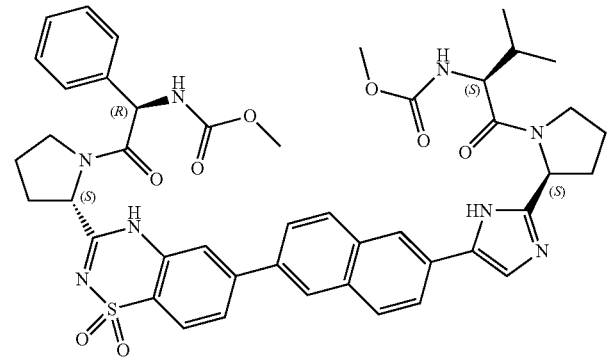

87

Disopropylethylamine (369.7 mg, 2.87 mmol) was added dropwise to the solution of compound 86 (600 mg, 0.72 mmol) in $CH_2Cl_2$ (15 mL) at 0° C. Methyl chloroformate (81.2 mg, 0.86 mmol) was added. The mixture was stirred at 20° C. for 1 hour and then washed by aqueous KOH (15 mL), $NaHCO_3$ (15 mL) and brine (15 mL). The organic layer was dried on $Na_2SO_4$ and after filtration, the filtrate was concentrated. The obtained crude product was purified by high-performance liquid chromatography (eluent: $CH_3CN/H_2O$ from 31/69 to 61/39 with 0.75% $CF_3COOH$ as buffer). The desired fraction was collected and basified by saturated (3×100 mL). The organic layer was dried on $Na_2SO_4$ and after filtration, the solvent was removed in vacuo. The product was further purified by SFC (eluent: Supercritical $CO_2$/ $CH_3CH_2OH$ from 65/35 at 80 mL/min with 0.05% DEA as buffer, Column Temp: 38° C., Nozzle Pressure: 100 Bar, Nozzle Temp: 60° C., Evaporator Temp: 20° C., Trimmer Temp: 25° C., Wavelength: 220 nm). The organic layer was concentrated to dryness, resulting in compound 87 (113 mg) Method B; Rt: 4.91 min. m/z=: 861.3 $(M+H)^+$ Exact mass: 860.3

SFC: Columns: Chiralcel OJ-H 250 mm*4.6 mm; 5 um; Flow: 2.35 mL/min; Mobile phase: A: $CO_2$ B: EtOH (0.05% Diethylamine); 40% B in A,: Rt: 5.39 min

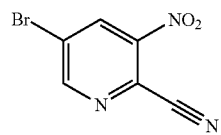

88

1) TBAF, DMF, -15° C.
2) 2N HCl

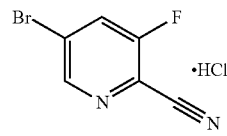

89

To a solution of tetrabutyl-ammonium fluoride (TBAF, 51.2 g, 197.4 mmol, 1.5 eq) in DMF (100 mL), 4 A Molecular sieves powder (30 g) were added. The resulting mixture was stirred for 30 minutes. The mixture was filtered and the filtrate was transferred into a 1000 mL reaction flask. A solution of compound 88 (30 g, 131.6 mmol, 1.0e q) in DMF (50 mL) was added to the above solution via a addition funnel over 10 minutes, while maintaining the internal temperature below −15° C. After stirring for 20 minutes, 2 N HCl (60 mL) was added over 5 minutes. After aging for 1 hour, the mixture was cooled to 2.5° C. and filtered. The filtration cake was washed by DMF/water (10% (v/v), 2×36 mL). The filtrate was combined and concentrated in vacuo. The resulting residue was re-crystallized from 2-propanol (50 mL) to afford the desired compound 89 (13 g).

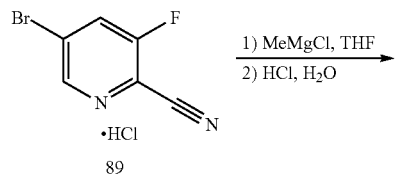

89

1) MeMgCl, THF
2) HCl, $H_2O$

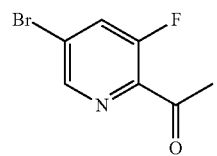

90

The solution of compound 89 (7.5 g) in toluene (100 mL) was cooled to −10° C. and MeMgCl (3N in ethyl ether, 25 mL, 74.6 mmol) was added over 2 minutes under $N_2$, during which the temperature raised to 0° C. The mixture was allowed to stir at −10° C. for 1 hour. Then 3 N hydrochloric acid (91 mL, 274 mmol) was added over 3 minutes via a addition funnel. The mixture was stirred at room temperature for 18 hours. The reaction was quenched with 0.5 M $NaHCO_3$ (30 mL) and the obtained mixture was stirred at room temperature for 30 minutes. The organic layer was washed with water, 10% aqueous $Na_2SO_4$ (2×5 mL), and water (2×5 mL). The combined layer was concentrated and next co-concentrated with toluene (50 mL) and MeOH (50 mL). The residue was purified by silica gel column chromatography (gradient eluent: petroleum ether: ethyl acetate=20:1 to 8:1). The desired section was collected, the volatiles were removed in vacuo to afford compound 90 (6.4 g). Method A2; Rt: 0.88 min. m/z=: 219.7 $(M+H)^+$ Exact mass: 219.0

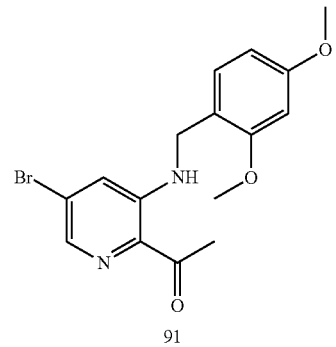

91

2,4-Dimethoxy-benzylamine (4.3 g, 25.6 mmol) was added to compound 90 (5.6 g, 25.6 mmol, 1.0 eq) in DMF (12 mL). The reaction mixture was stirred under microwave irradiation for 0.5 hour at 120° C. under nitrogen. The solvent was removed under vacuum. The residue was solidified by methanol (10 mL), resulting in compound 91 (6.8 g, 73%) Method A2; Rt: 1.33 min. m/z=: 366.8 $(M+H)^+$ Exact mass: 366.0

121

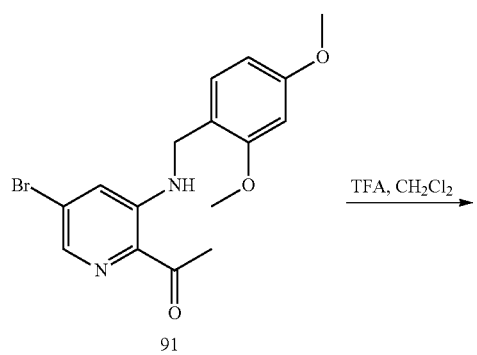

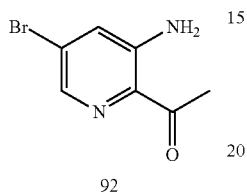

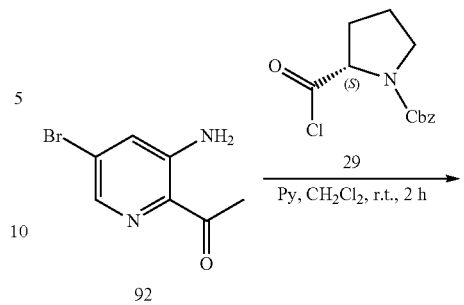

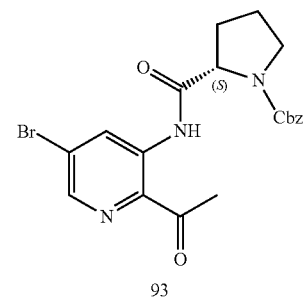

Trifluoro-acetic acid (6.4 g, 55.9 mmol) was added to a solution of compound 91 (6.8 g, 18.6 mmol) in CH₂Cl₂ (68 mL). The mixture was stirred for 0.5 hour after which the solvent was removed. To the obtained residue, tert-butylmethyl ether (50 mL) was added and the mixture was filtered. The filtrate was collected and washed with saturated Na₂CO₃ aqueous solution. The organic layer was dried over MgSO₄, filtered and concentrated resulting in compound 92 (3.6 g) Method A2; Rt: 1.00 min. m/z=: 216.6 (M+H)⁺ Exact mass: 216.0

To the solution of compound 92 (5.74 g, 16.7 mmol) and compound 29 (3.6 g, 16.7 mmol) in CH₂Cl₂ (25 mL), pyridine (25 mL) was added dropwise. The mixture was stirred for 1 hour at room temperature. Then the solution was concentrated in vacuo. The residue was purified by silica gel chromatography (eluent: petroleum ether/ethyl acetate=2.5/1), resulting in compound 93 (3.8 g, 51%).
Method A2; Rt: 1.22 min. m/z=: 445.8 (M+H)⁺ Exact mass: 445.1

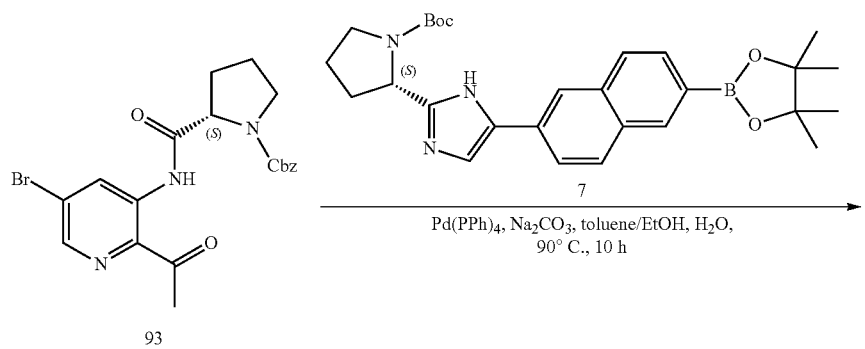

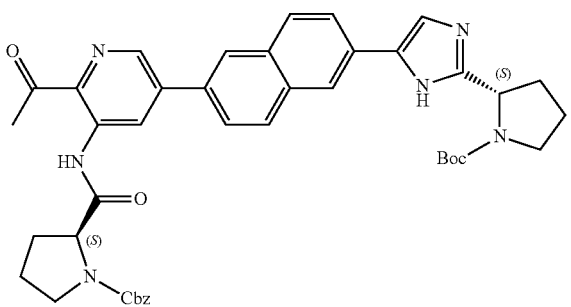

Na$_2$CO$_3$ (0.95 g, 9 mmol) in H$_2$O (15 mL) was added to a mixture of compound 93 (2.0 g, 4.8 mmol), compound 7 (2.2 g, 4.8 mmol), ethanol (15 mL) and toluene (30 mL). Pd(PPh$_3$)$_4$ (0.52 mg, 0.45 mmol) was next added in one portion under nitrogen. The mixture was stirred for 10 hours at 90° C. Then, the solution was cooled to room temperature and filtered. The filtrate was concentrated in vacuo. The residue was dissolved in CH$_2$Cl$_2$ (20 mL) and washed with water (3×10 mL). The solution was dried over Na$_2$SO$_4$ and concentrated under reduced pressure. The residue was purified by silica gel column chromatography (gradient eluent: ethyl acetate/dichloromethane=1/5 to 3/1), resulting in compound 94 (2.0 g, 61%). Method A2; Rt: 1.08 min. m/z=: 728.3 (M+H)$^+$ Exact mass: 729.2 dioxane (14 mL) was added via a syringe. The mixture was stirred in a preheated oil bath at 110° C. for 1.5 hours. The mixture was allowed to cool to room temperature, after which ethanol was added. The solution was concentrated in vacuo and the obtained residue was purified by preparative high-performance liquid chromatography (eluent: CH$_3$CN/ H$_2$O=30/70 to 60/40, 0.1% CF$_3$COOH). The desired fraction was collected and the pH of the solution was adjusted to about 8 with saturated NaHCO$_3$. Then the acetonitrile was removed under reduced pressure. The aqueous layer was extracted with CH$_2$Cl$_2$ (3×50 mL) and the organic layers were combined and dried on Na$_2$SO$_4$. The solution was concentrated

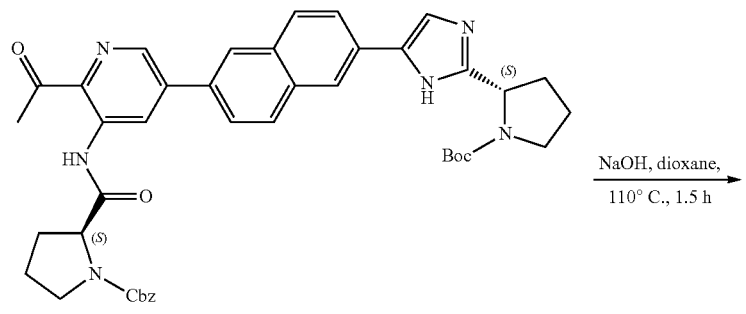

An oven-dried tube with a stirring bar was charged with compound 94 (1.44 g, 1.98 mmol, 1.0 eq) and crushed NaOH (0.276 g, 6.9 mmol, co-evaporated with dry toluene). Dry and the obtained residue was dried in vacuo, resulting in compound 95 (0.22 g, 16%). Method A2; Rt: 0.92 min. m/z=: 711.2 (M+H)$^+$ Exact mass: 710.3

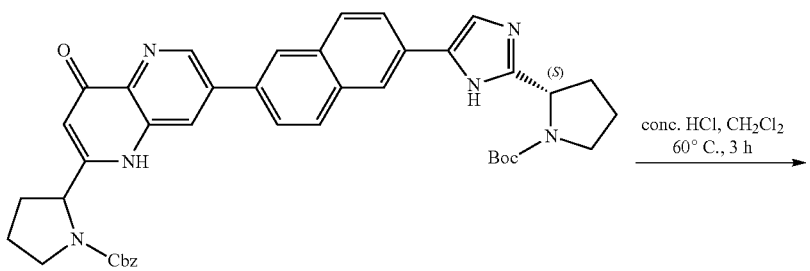

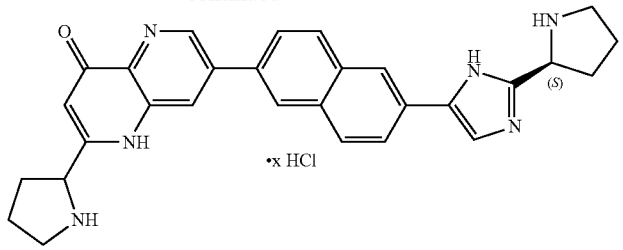

96

Compound 95 (0.2 g, 0.28 mmol) was dissolved in CH₂Cl₂ (5 mL) and concentrated HCl (5 mL) was added dropwise. The mixture was stirred at 60° C. for 3 hours. The solvent was evaporated in vacuo. The residue was washed with a mixture of tert-butyl methyl ether and methanol (1:1). The solid was filtered and dried under high vacuum. Crude compound 96 (0.138 g) was used in the next step as such.

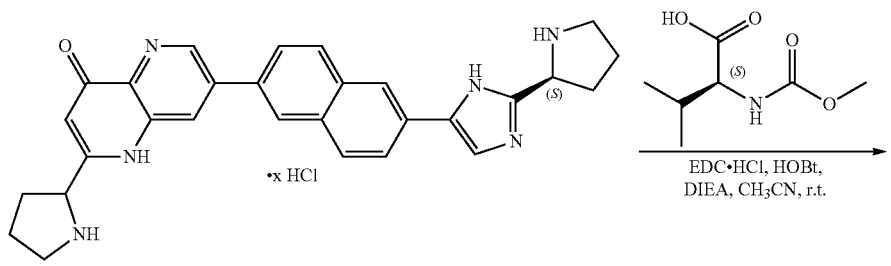

96

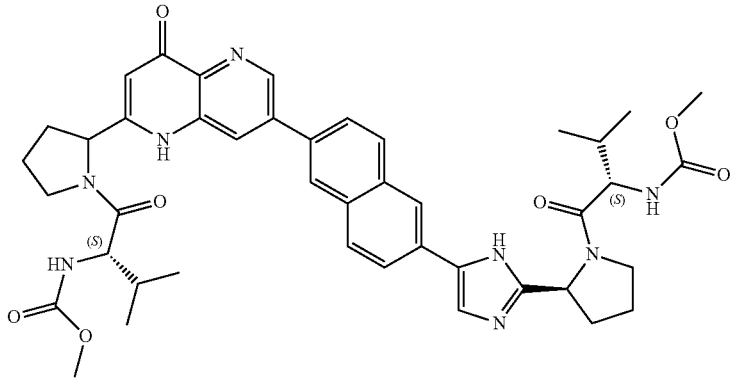

97

EDC.HCl (0.116 g, 0.604 mmol) and HOBT (0.081 g, 0.604 mmol) were added to the solution of (S)-2-(methoxycarbonylamino)-3-methylbutanoic acid (0.106 g, 0.604 mmol) in acetonitrile (5 mL). The mixture was stirred at 20° C. for 1 hour. Then compound 96 (0.138 g) was added. The slurry was cooled to 0° C. and DIEA (0.13 g, 1.0 mmol) was added. The mixture was stirred at room temperature for 15 hours. The mixture was concentrated and diluted with CH₂Cl₂ (20 mL) and 1 N HCl (5 mL). The organic layer was separated and washed with saturated NaHCO₃ and brine. The crude product obtained after concentration of the organic layer was purified by preparative high-performance liquid chromatography (eluent: CH₃CN/H₂O=30/70 to 60/40, 0.1% CF₃COOH). The desired fraction was collected and the pH of the solution was adjusted to about 8 with NaHCO₃. Then, acetonitrile was removed under reduced pressure and the aqueous layer was extracted with CH₂Cl₂ (3×50 mL). The organic layers were combined and dried on Na₂SO₄. The obtained solution was concentrated and the thus obtained residue was dried in vacuo resulting in compound 97 (3.0 mg). Method B; Rt: 4.38 min. m/z=: 791.1 (M+H)⁺ Exact mass: 790.4; Chiral HPLC: Columns: OJ-R 250 mm*4.6 mm; 5 um; Flow: 0.5 mL/min; Mobile phase: A: H₂O (0.069% TFA), B: Acetonitrile A/B=80/20 Rt: 15.5 min.; Chiral HPLC: Columns: AS-R 250 mm*4.6 mm; 5 um; Flow: 0.5 mL/min; Mobile phase: A: H₂O (0.069% TFA), B: Acetonitrile A/B=80/20 Rt: 14.9 min

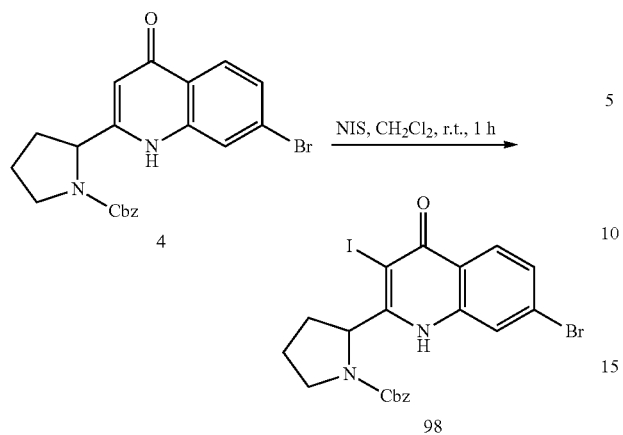

Compound 4 (1 g, 2.3 mmol) was dissolved in CH₂Cl₂ (20 mL). NIS (0.44 g, 2.6 mmol) was added and the resulting mixture was stirred at room temperature for 1 hour. The mixture was washed by 10% Na₂SO₃ and then by brine. The solvent was removed in vacuo. The resulting residue was purified by flash column. (Eluent: ethyl acetate/petrol ether, 1:1). The collected fractions were combined and concentrated in vacuo. The resulting solid was suspended by ethyl acetate (3 mL) and stirred for 30 minutes. Compound 98 (yellow powder, 0.5 g, 39%) was collected by filtration and dried in a high vacuum oven.

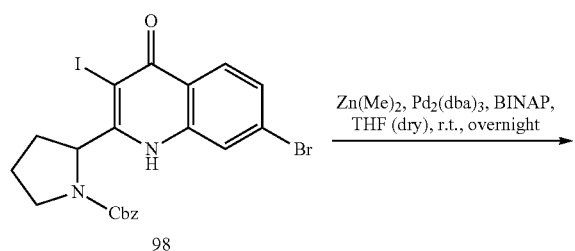

A mixture of compound 98 (0.28 g, 0.506 mmol), Zn(Me)₂ (1M in heptane, 1 mL, 1.012 mmol), Pd₂(dba)₃ (28 mg, 0.0304 mmol) and BINAP (19 mg, 0.0304 mmol) in dry THF (4.5 mL) was stirred under N₂ overnight at 20° C. More Zn(Me)₂ (1 M in heptane, 1 mL), Pd₂(dba)₃ (28 mg) and BINAP (20 mg) were added. The mixture was stirred for another 3 hour at 20° C., followed by addition of more Zn(Me)₂ (1 mL), Pd₂(dba)₃ (28 mg) and BINAP (20 mg). The mixture was stirred under N₂ overnight at 20° C. The mixture was quenched with saturated aqueous NH₄Cl and the mixture was extracted with dichloromethane (2×20 mL). The combined organic layers were washed with brine and dried over Na₂SO₄. The solvent was removed in vacuo. The residue was purified by flash column (gradient eluent: petroleum ether/ethyl acetate: from 100/0 to 1/3), resulting in compound 99 (75 mg, 34%).

Method A2; Rt: 1.07 min. m/z=: 441.0 (M+H)⁺ Exact mass: 440.1

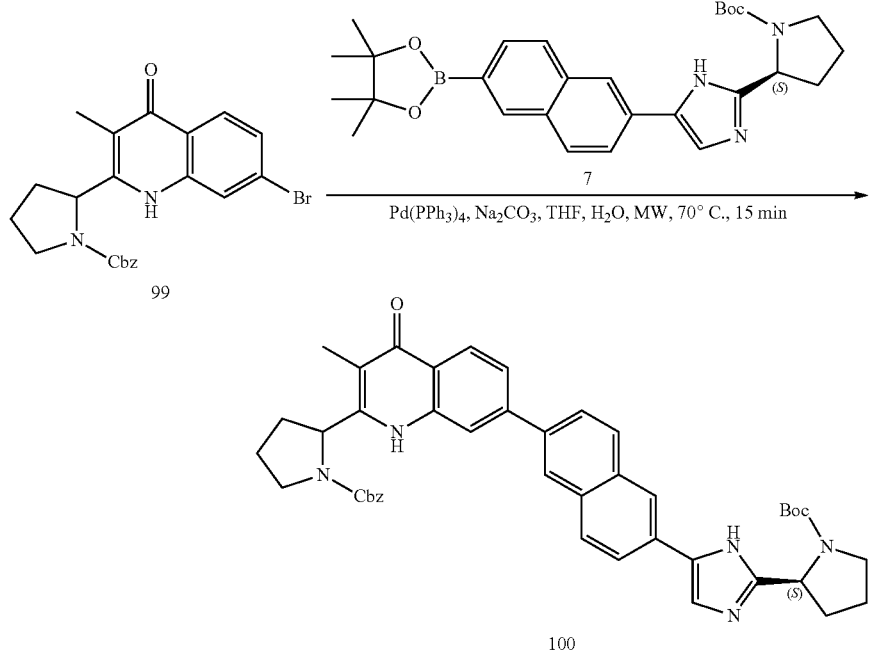

Compound 99 (75 mg, 0.170 mmol) and compound 7 (0.1 g, 0.204 mmol) were dissolved in THF (1.6 mL) and a solution of $Na_2CO_3$ (72 mg, 0.68 mmol) in $H_2O$ (0.4 mL) was added, followed by $Pd(PPh_3)_4$ (40 mg, 0.034 mmol) under $N_2$. The mixture was stirred under microwave irradiation for 15 min at 70° C. under $N_2$. The volatiles were removed in vacuo and water (5 mL) was added. The aqueous layer was extracted with dichloromethane (2×10 mL). The combined organic layers were washed with brine and dried over $Na_2SO_4$. The solvent was removed in vacuo. The obtained residue was purified by flash column (gradient eluent: first: ethyl acetate/methanol: from 100/0 to 10/1, then dichloromethane/methanol=12/1) resulting in compound 100 (70 mg). Method A2; Rt: 1.03 min. m/z=: 724.2 $(M+H)^+$ Exact mass: 723.3

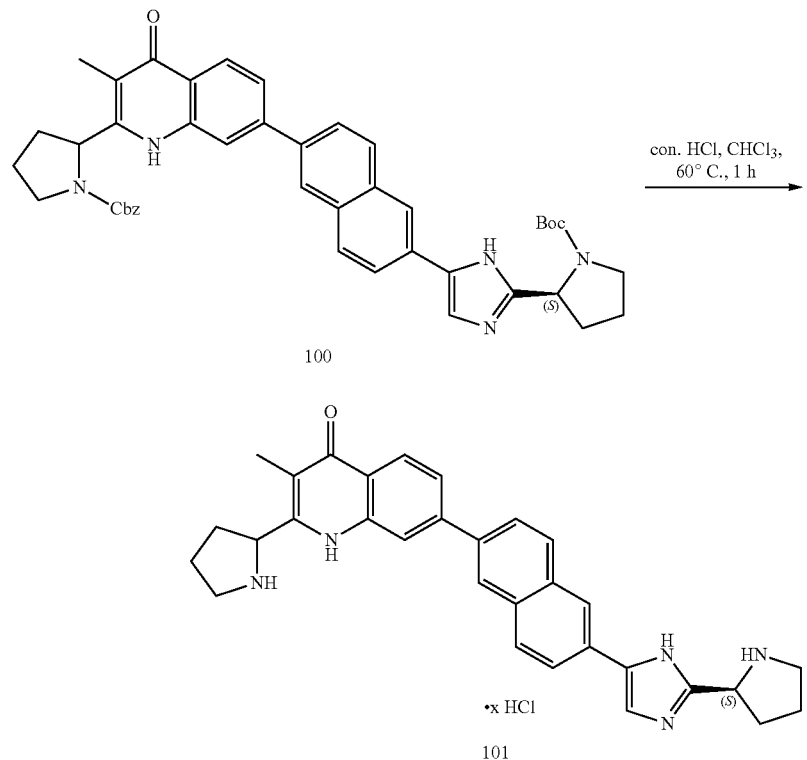

A mixture of compound 100 (70 mg, 0.097 mmol) in conc.HCl (1 mL) and $CHCl_3$ (1 mL) was stirred for 1 hour at 60° C. The solvent was removed in vacuo. The residue was co-evaporated with toluene (2×10 mL), resulting in compound 101 (70 mg).

Method A2; Rt: 0.80 min. m/z=: 490.2 $(M+H)^+$ Exact mass: 489.2

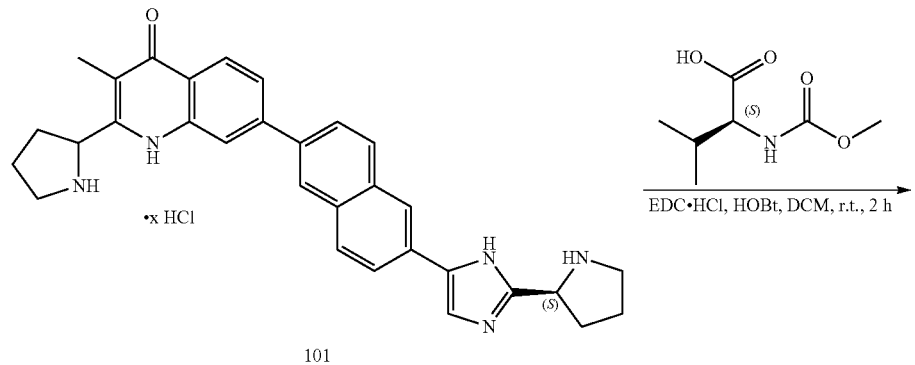

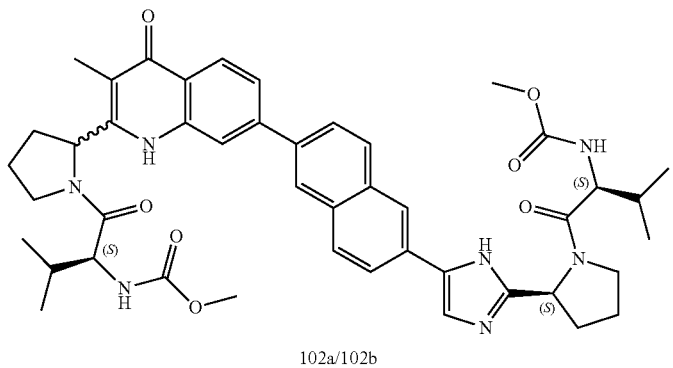

102a/102b

Compound 101 (70 mg), (S)-2-(methoxycarbonylamino)-3-methylbutanoic acid (41 mg, 0.23 mmol), EDC.HCl (46 mg, 0.24 mmol) and HOBt (7 mg, 0.048 mmol) in CH$_2$Cl$_2$ (2 mL) was cooled to 0° C. DIEA (0.17 mL, 0.97 mmol) was added. The mixture was stirred overnight at 15° C. The solvent was removed in vacuo. The residue was purified by high-performance liquid chromatography (C18, eluent: CH$_3$OH/H$_2$O from 15/85 to 45/55 with 0.1% TFA as buffer). The pure fractions were collected and the mixture was basified with saturated aqueous NaHCO$_3$ to pH=8. The volatiles were removed in vacuo. The precipitate was filtered off and dried in vacuo, resulting in compound 102a (14.6 mg) and compound 102b (14.2 mg) separately. 102a: Method B; Rt: 4.63 min. m/z=: 804.3 (M+H)$^+$ Exact mass: 803.4

SFC: Columns: Chiralcel AS-H 250 mm*4.6 mm; 5 um; Flow: 2.5 mL/min; Mobile phase: A: CO$_2$ B: EtOH (0.05% Diethylamine); 40% B in A,: Rt: 2.84 min SFC: Columns: Chiralcel OJ-H 250 mm*4.6 mm; 5 um; Flow: 2.5 mL/min; Mobile phase: A: CO$_2$ B: EtOH (0.05% Diethylamine); 40% B in A,: Rt: 2.43 min. 102b: Method B; Rt: 4.79 min. m/z=: 804.3 (M+H)$^+$ Exact mass: 803.4

SFC: Columns: Chiralcel AS-H 250 mm*4.6 mm; 5 um; Flow: 2.35 mL/min; Mobile phase: A: CO$_2$ B: MeOH (0.05% Diethylamine); 5 to 40% B in A,: Rt: 8.75 min SFC: Columns: Chiralcel OD-H 150 mm*4.6 mm; 5 um; Flow: 2.35 mL/min; Mobile phase: A: CO$_2$ B: MeOH (0.05% Diethylamine); 5 to 40% B in A,: Rt: 9.63 min.

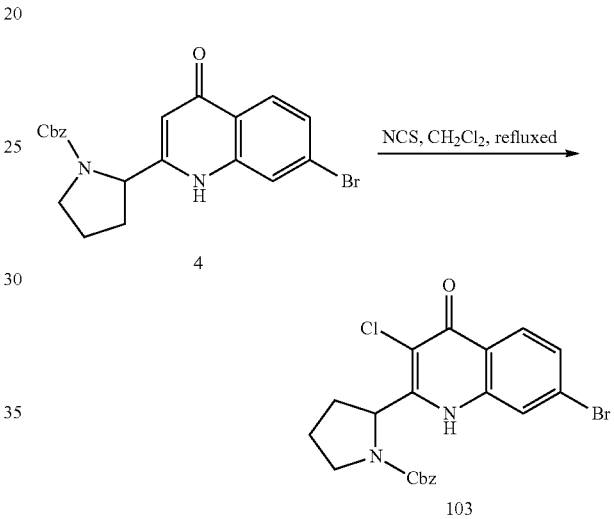

NCS (0.31 g, 2.34 mmol) was added to a solution of compound 4 (0.5 g, 1.17 mmol) in CH$_2$Cl$_2$. The mixture was refluxed for 4 hours and after cooling to room temperature washed with 10% Na$_2$SO$_3$, 10% K$_2$CO$_3$ and brine. The organic layer was dried over MgSO$_4$ and the obtained solution concentrated under reduced pressure. The obtained residue was washed with CH$_2$Cl$_2$ and filtered, resulting in compound 103 (0.18 g).

Method A2; Rt: 1.09 min. m/z=: 462.8 (M+H)$^+$ Exact mass: 462.0

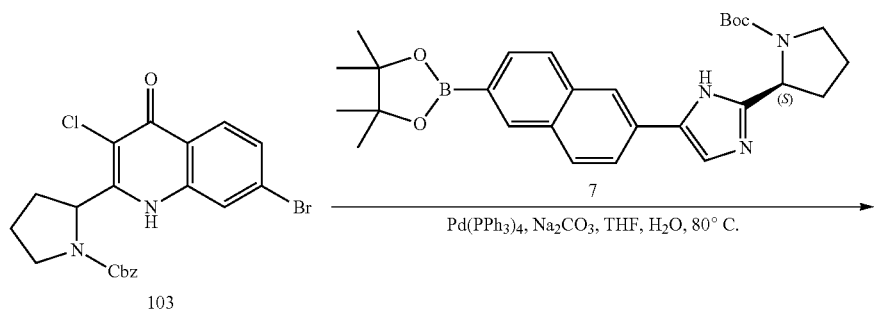

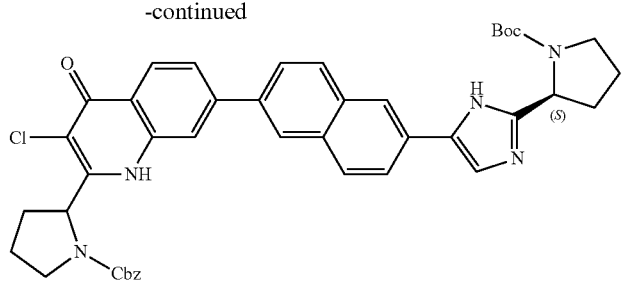

104

Pd(PPh₃)₄ (0.1 g, 0.087 mmol, 0.25 eq) was added to the mixture of compound 103 (0.16 g, 0.346 mmol) and compound 7 (0.17 g, 0.346 mmol) in THF (6 mL) and H₂O under nitrogen. The mixture was stirred under microwave irradiation for 15 minutes at 80° C. Then the solution was cooled to room temperature and filtered. The filtrate was concentrated in vacuo. The obtained residue was dissolved in CH₂Cl₂ (20 mL) and washed with water (3×10 mL). The organic layer was dried on Na₂SO₄ and concentrated under reduced pressure. The residue was purified by silica gel column chromatography (gradient eluent: ethyl acetate/dichloromethane=1/5 to 3/1). The desired fraction was collected, the solvent was evaporated and the obtained residue was dried in vacuo, resulting in compound 104 (0.22 g, 50%).

Method A2; Rt: 1.02 min. m/z=: 744.2 (M+H)⁺ Exact mass: 743.3

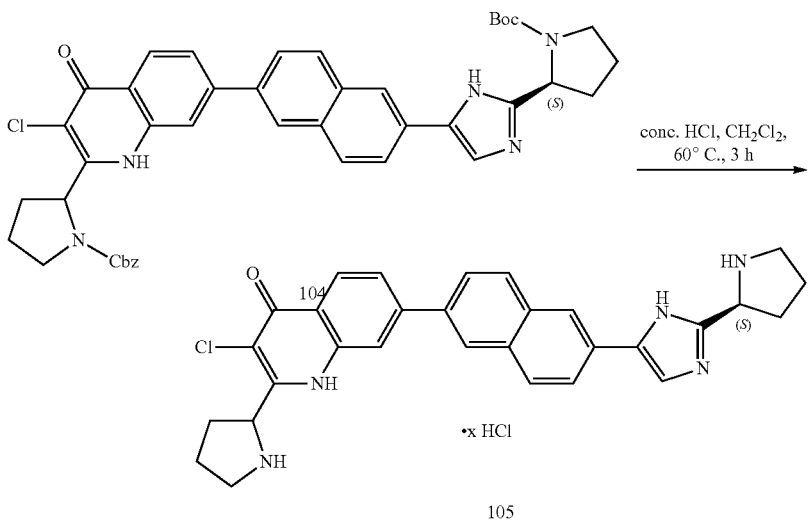

Compound 104 (0.2 g, 0.156 mmol,) was dissolved in CH₂Cl₂ (3 mL) and concentrated HCl (3 mL) was added dropwise. The mixture was stirred at 60° C. for 3 hours. The solvent was evaporated in vacuo and the obtained residue was washed with a mixture of tert-butyl methyl ether and methanol (1/1). The solid was filtered and dried under high vacuum, resulting in compound 105 (90 mg). The crude product was used as such in the next step.

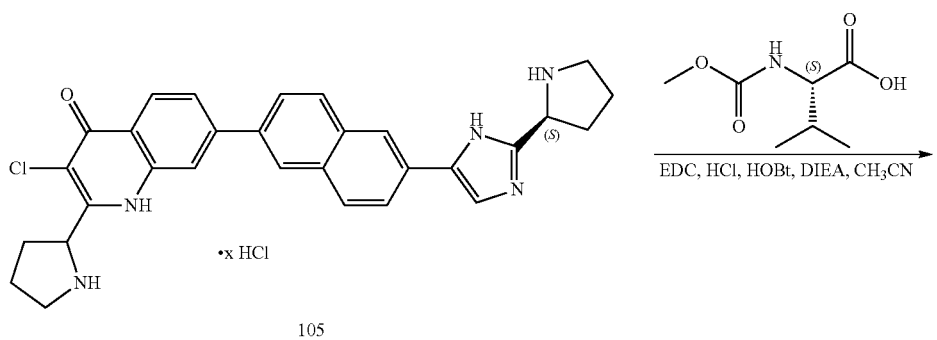

105

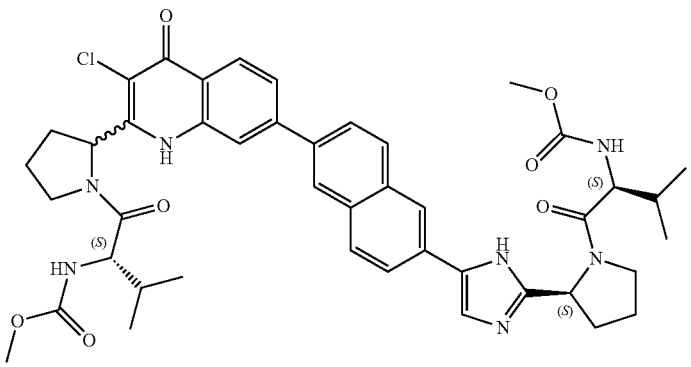

106a/b

EDC.HCl (71.7 mg, 0.374 mmol) and HOBT (50.5 mg, 0.374 mmol) were added to a solution of (S)-2-(methoxycarbonylamino)-3-methylbutanoic acid (65.5 mg, 0.374 mmol) in acetonitrile (5 mL). The mixture was stirred at 20° C. for 1 hour. Then compound 105 (90.8 mg) was added. The slurry was cooled to 0° C. and DIEA (80.6 mg, 0.624 mmol) was added. The mixture was stirred at room temperature for 2 hours. The mixture was concentrated and diluted with $CH_2Cl_2$ (20 mL) and 1 N HCl (5 mL) aqueous solution. The organic layer was separated and washed with $NaHCO_3$ saturated aqueous and brine. The organic layer was concentrated and the obtained crude product was purified by preparative high-performance liquid chromatography (eluent: $CH_3CN/H_2O$=30/70 to 60/40, 0.1% $CF_3COOH$). The desired fractions were collected and the pH of the solution was adjusted to about 8 with saturated $NaHCO_3$. Then the acetonitrile was removed under reduced pressure. The aqueous layer was extracted with $CH_2Cl_2$ (3×50 mL) and the organic layers were combined and dried on $Na_2SO_4$. After filtration, the solvent was evaporated and the obtained residue was dried in vacuo resulting in compound 106a (13.1 mg) and 106b (6.7 mg)
106a: Method C; Rt: 3.58 min. m/z=: 824.4 (M+H)+ Exact mass: 823.4

SFC: Columns: Chiralcel OD-H 150 mm*4.6 mm; 5 um; Flow: 2.35 mL/min; Mobile phase: A: $CO_2$ B: EtOH (0.05% Diethylamine); 40% B in A,: Rt: 5.38 min SFC: Columns: Chiralcel AS-H 250 mm*4.6 mm; 5 um; Flow: 2.35 mL/min; Mobile phase: A: $CO_2$ B: EtOH (0.05% Diethylamine); 40% B in A,: Rt: 9.27 min.

106b: Method C; Rt: 3.70 min. m/z=: 824.4 (M+H)+ Exact mass: 823.4

SFC: Columns: Chiralcel OD-H 150 mm*4.6 mm; 5 um; Flow: 2.35 mL/min; Mobile phase: A: $CO_2$ B: EtOH (0.05% Diethylamine); 40% B in A,: Rt: 5.38 min SFC: Columns: Chiralcel OJ-H 250 mm*4.6 mm; 5 um; Flow: 2.35 mL/min; Mobile phase: A: $CO_2$ B: EtOH (0.05% Diethylamine); 5 to 40% B in A,: Rt: 8.66 min.

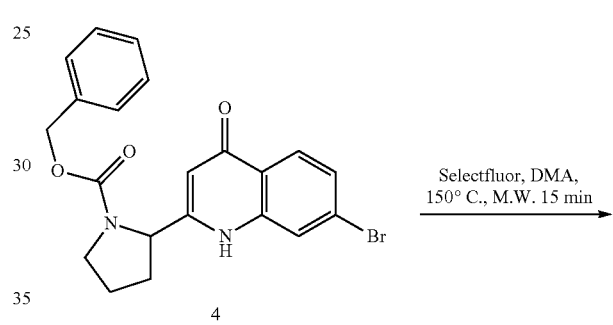

4

Selectfluor, DMA, 150° C., M.W. 15 min

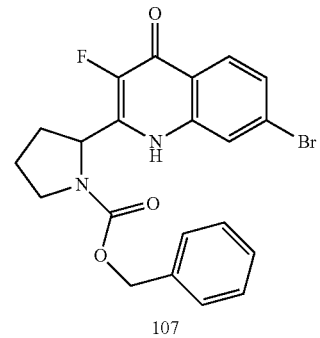

107

Compound 4 (1 g, 2.3 mmol) and Selectfluor (0.81 g, 2.3 mmol) in DMA (10 mL) were stirred at 150° C. for 15 min. The mixture was cooled to room temperature. and poured into pre-cooled saturated $NaHCO_3$ (100 mL). The precipitate was filtered, washed with $H_2O$ and purified by silica gel chromatography. (Eluent: $CH_2Cl_2$/EtOAc, 1/1). The collected fractions were combined and concentrated in vacuo. The obtained residue was solidified by THF (3 mL), resulting in compound 107 (0.13 g).

Method A2; Rt: 1.55 min. m/z=: 447.0 (M+H)+ Exact mass: 446.1

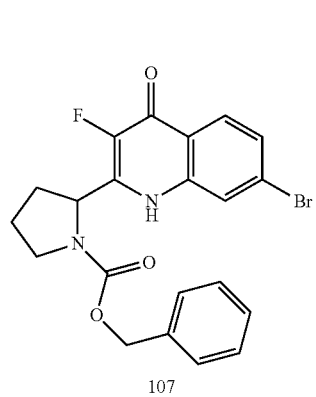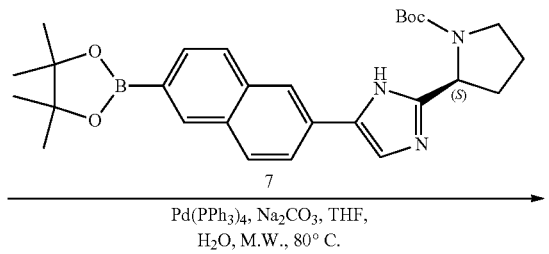

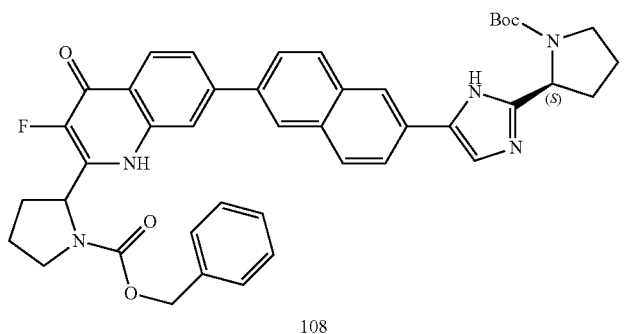

Pd(PPh₃)₄ (0.098 g, 0.085 mmol) was added to a mixture of compound 107 (0.15 g, 0.34 mmol), compound 7 (0.16 g, 0.34 mmol) and Na₂CO₃ (0.16 g, 1.53 mmol) in THF (9 mL) and H₂O (2.15 mL) in one portion under nitrogen. The mixture was stirred under microwave irradiation for 15 minutes at 80° C. The mixture was cooled to room temperature, the solvent was removed in vacuo. Purification by preparative thin layer chromatography (Eluent: CH₂Cl₂/methanol, 1/10), resulted in compound 108 (0.10 g).

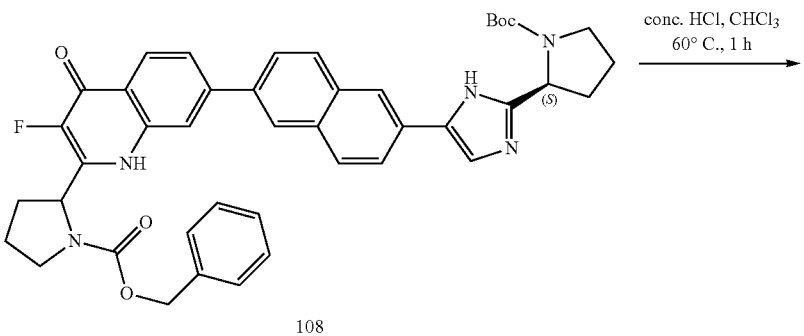

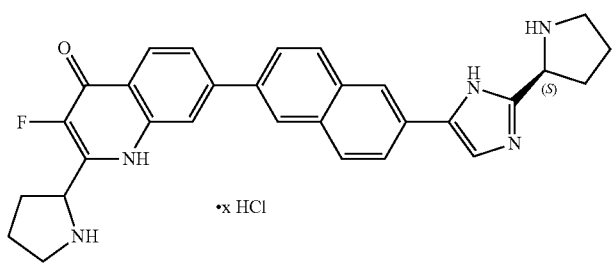

Compound 108 (0.1 g, 0.12 mmol) was dissolved in CHCl₃ (5 mL) and concentrated HCl (2 mL). The mixture was stirred at 60° C. in sealed tube for 1 hour. The mixture was cooled to room temperature and the aqueous layer was concentrated in vacuo. The resulting solid was co-evaporated with toluene (2×10 mL), resulting in compound 109 (0.1 g).

SFC: Column: Chiralcel OJ-H 250 mm*4.6 mm; 5 um; Flow: 2.35 mL/min; Mobile phase: A: CO₂ B: iPrOH (0.05% Diethylamine); 5 to 40% B in A,: Rt: 9.43 min SFC: Column: Chiralcel OD-H 150 mm*4.6 mm; 5 um; Flow: 2.35 mL/min; Mobile phase: A: CO₂ B: MeOH (0.05% Diethylamine); 40% B in A,: Rt: 4.62 min.

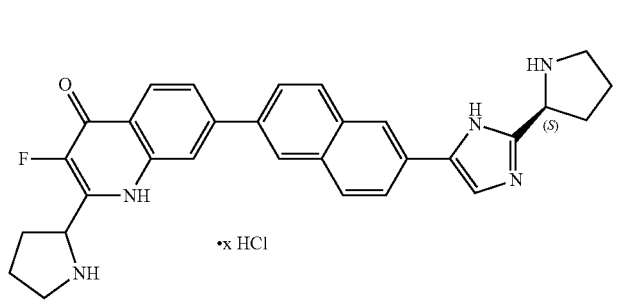

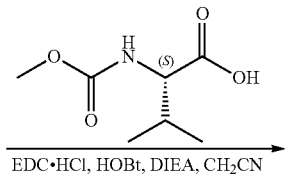

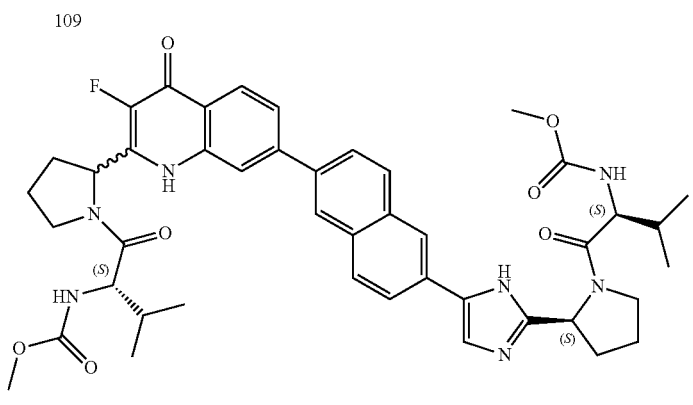

EDC.HCl (70 mg, 0.36 mmol) and HOBt (50 mg, 0.36 mmol) were added to the solution of (S)-2-(methoxycarbonylamino)-3-methylbutanoic acid (63 mg, 0.36 mmol) in acetonitrile (5 mL). The mixture was stirred at 10° C. for 1 hour. Then compound 109 (100 mg) and DIEA (0.18 g, 1.4 mmol) were added at 0° C. The mixture was stirred at room temperature for 2 hours and concentrated in vacuo. The resulting residue was purified by preparative high-performance liquid chromatography (eluent: CH₃CN/H₂O=30/70 to 60/40, 0.1% CF₃COOH). The desired fractions were collected and the pH of the solution was adjusted to about 8 with NaHCO₃. The acetonitrile was removed under reduced pressure. The aqueous layer was extracted with CH₂Cl₂ (3×50 mL) and the organic layers were combined and dried on Na₂SO₄. The solutions were evaporated and the residues were dried in vacuo. The resulting products were solidified by methyl-tert-butylether, resulting in compound 110a (21 mg) and 110b (17 mg).

110a: Method C; Rt: 3.49 min. m/z=: 808.5 (M+H)⁺ Exact mass: 807.4

SFC: Column: Chiralcel OJ-H 250 mm*4.6 mm; 5 um; Flow: 2.35 mL/min; Mobile phase: A: CO₂ B: iPrOH (0.05% Diethylamine); 5 to 40% B in A,: Rt: 9.14 min SFC: Column: Chiralcel OD-H 150 mm*4.6 mm; 5 um; Flow: 2.35 mL/min; Mobile phase: A: CO₂ B: MeOH (0.05% Diethylamine); 40% B in A,: Rt: 6.08 min.

110b: Method C; Rt: 3.60 min. m/z=: 808.4 (M+H)⁺ Exact mass: 807.4

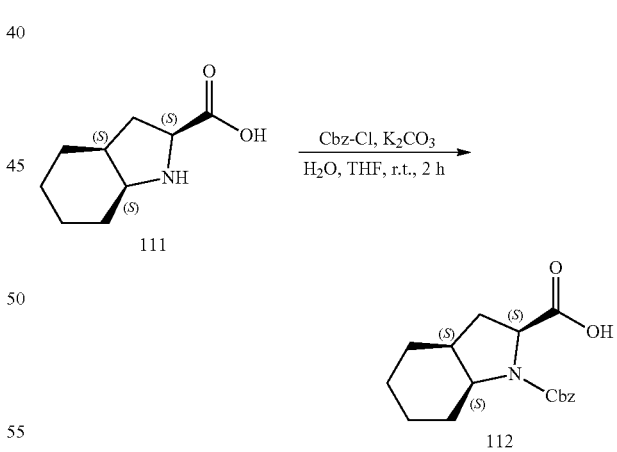

Compound 111 (20 g, 119 mmol) and K₂CO₃ (23 g, 165 mmol) were dissolved in THF (60 mL) and H₂O (60 mL) at room temperature. The reaction was stirred at room temperature for 5 minutes, the mixture was cooled to 0° C. and Cbz-Cl (22 g, 131 mmol) was slowly added. The mixture was then stirred at room temperature for 2 hours. The mixture was acidified to Ph=3 and the product was extracted with dichloromethane (2×40 mL). The combined organic layer was concentrated, and the obtained residue dried in vacuo, resulting in compound 112 (34 g, 96%)

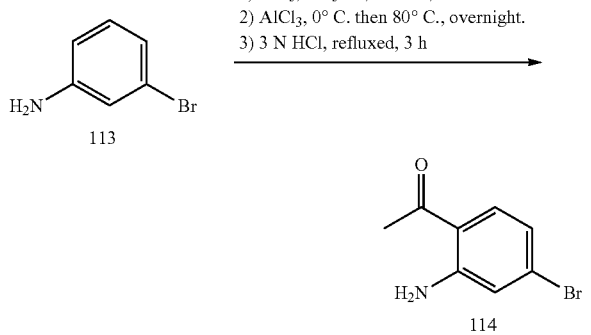

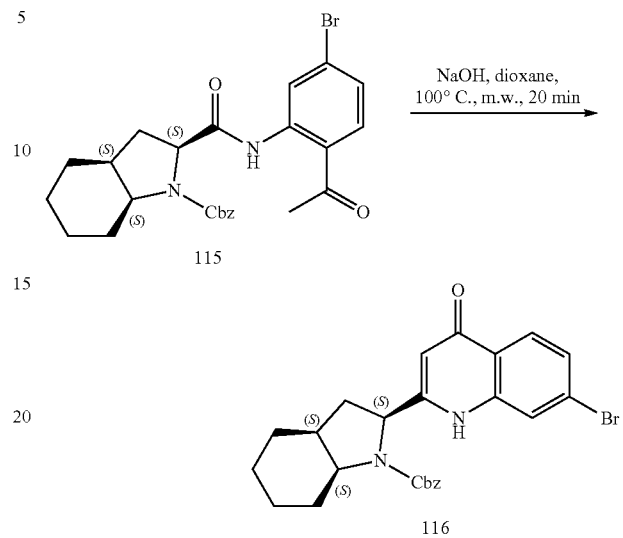

Method A2; Rt: 1.36 min. m/z=: 521.0 (M+Na)⁺ Exact mass: 498.1

Acetonitrile (23.7 g, 580 mmol) was added to 3-Bromoaniline (113) (10 g, 58 mmol) in toluene (70 mL). The mixture was cooled to 0° C. and BCl₃ (1 M in CH₂Cl₂, 64 mL, 64 mmol) was added dropwise, while keeping the temperature below 10° C. Next, AlCl₃ (11.6 g, 87 mmol) was added in small portions at 0° C. The reaction mixture was heated to 90° C. for 5 hours. The reaction mixture was cooled to room temperature and quenched with aqueous HCl (2N, 100 mL). The mixture was heated to 50° C. for 1 hour, cooled to room temperature and separated. The organic layer was separated and washed with water and brine. The organic layer was collected, dried and concentrated, resulting in compound 114 (4 g).

Method A2; Rt: 0.98 min. m/z=: 215.7 (M+H)⁺ Exact mass: 215.0

Compound 115 (2.0 g, 4 mmol) and NaOH (0.48 g, 12 mmol) were added to dry dioxane at room temperature. The mixture was heated to 100° C. under microwave irradiation for 20 minutes. (8 parallel reactions were carried out and worked up together.) The mixture was filtrated and the filtrate was concentrated in vacuo. The crude product was purified by column chromatography. (Eluent: petroleum ether and ethyl acetate, 2:1) resulting in compound 116 (1.5 g).

Method A2; Rt: 1.21 min. m/z=: 483.1 (M+H)⁺ Exact mass: 482.1

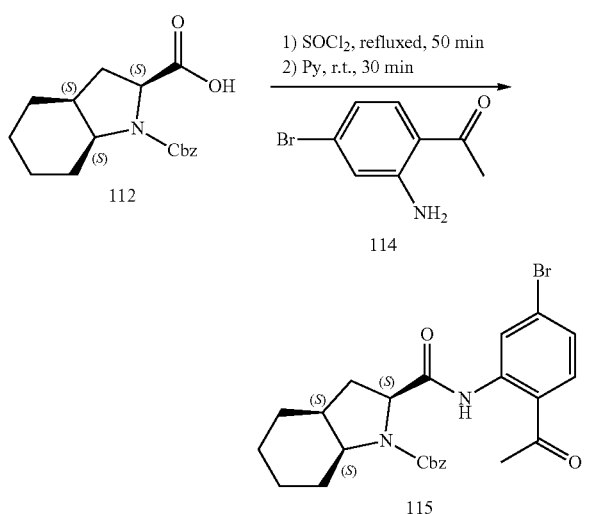

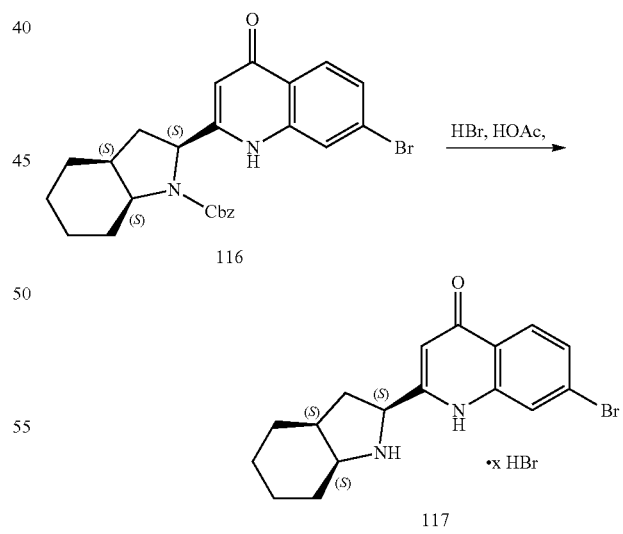

Compound 112 (15 g, 49.5 mmol) was dissolved in SOCl₂ (30 mL) at room temperature. The mixture was refluxed for 50 minutes and then concentrated in vacuo. To the obtained residue, compound 114 (12.7 g, 59.4 mmol) and pyridine (60 mL) were added sequentially at 0° C. The reaction mixture was stirred at room temperature for 30 minutes. The product was diluted with water and extracted with dichloromethane (2×50 mL). The organic layer was separated and concentrated to dryness. The crude product was purified by silica gel column chromatography (petroleum ether/ethyl acetate; 2/1) resulting in compound 115 (14.5 g).

Compound 116 (1.5 g, 3.1 mmol) was dissolved in 40% HBr/acetic acid (15 mL) at room temperature. The mixture was heated to 80° C. for 40 minutes. The mixture was concentrated in vacuo resulting in compound 117 (0.8 g).

Method A2; Rt: 0.83 min (minor isomer), 0.89 min (major isomer). m/z=: 346.9 (M+H)⁺ Exact mass: 346.1

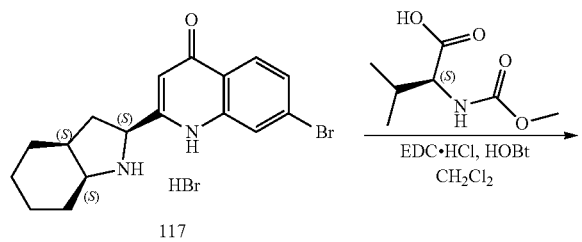

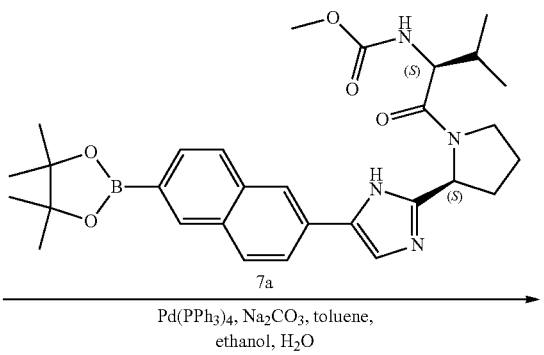

Compound 117 (0.8 g), (S)-2-(methoxycarbonylamino)-3-methylbutanoic acid (0.8 g, 4.6 mmol), EDC.HCl (0.9 g, 4.6 mmol), HOBt (0.06 g, 0.046 mmol) and TEA (0.46 g, 4.6 mmol) were dissolved in $CH_2Cl_2$ (20 mL) at room temperature. The reaction was stirred at room temperature for 50 minutes. The mixture was washed with water and extracted with $CH_2Cl_2$ (2×20 mL). The combined organic layer was dried and concentrated resulting in crude product. The crude product was purified by silica gel column chromatography. (Eluent: ethyl acetate) resulting in compound 118 (0.7 g).

Method A2; Rt: 1.04 min. m/z=: 503.9 $(M+H)^+$ Exact mass: 503.1

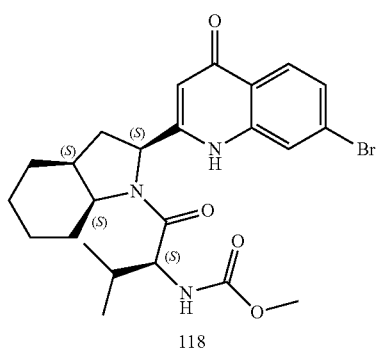

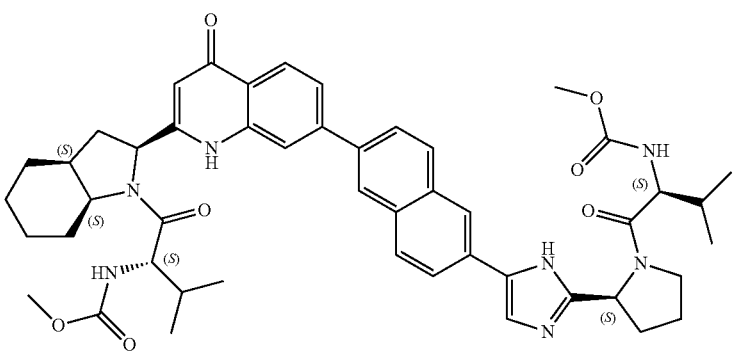

-continued

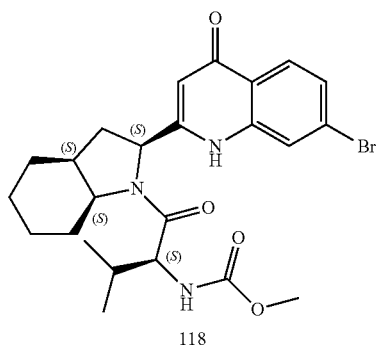

Compound 118 (purity 70%, 0.50 g, 1.0 mmol), compound 7a (0.55 g, 1.0 mmol), $Pd(PPh_3)_4$ (0.35 g, 0.3 mmol) and $Na_2CO_3$ (0.52 g, 4.0 mmol) in toluene (5 mL), ethanol (5 mL) and $H_2O$ (5 mL) were refluxed under $N_2$ atmosphere overnight. The mixture was cooled to 20° C. and extracted with $CH_2Cl_2$ (2×20 mL). The organic layer was concentrated in vacuo. The residue was washed with tert-butyl methyl ether (10 mL) and $CH_3CN$ (5 mL). The resulting powder was purified by preparative HPLC. (Column: Grace Vydac C18, 200*25 mm*5 um, Column temperature: 40° C., Mobile phase A: water (containing 0.075% TFA, V/V), Mobile phase B: acetonitrile, Flow rate: 30 mL/min, Gradient: 30-45% B, 0-15 min) The appropriate collected fractions were neutralized by saturated $NaHCO_3$. The organic solvent was removed in vacuo. The precipitate was filtered, washed with $H_2O$ and tert-butyl methyl ether and dissolved in methanol. The solution was concentrated in vacuo, resulting in compound 119a (77.1 mg)

A mixture fraction was further purified by SFC (Instrument: Berger MultiGram™ SFC, Mettler Toledo Co, Ltd. MG IIColumn: Chiral Cel OJ, 5 µm, Daicel Chemical Industries, Ltd 50×30 mmI.D. Mobile phase: A: Supercritical $CO_2$, B: MeOH (contained 0.2% Diethylamine), A:B=70:30 at 60 mL/min. Column Temp: 38° C. Wavelength: 220 nm. Nozzle Pressure: 100 Bar. Nozzle Temp: 60° C. Evaporator Temp: 20° C. Trimmer Temp: 25° C.). The collected fraction was concentrated in vacuo. The obtained residue was purified by preparative TLC. (Eluent: $CH_2Cl_2$/methanol, 10:1) The collected fraction was concentrated under vacuum and suspended in $CH_3CN$ (1 mL) and then MTBE (3 mL). The resulting solid was dissolved in methanol (2 mL) and filtrated. The obtained filtrate was concentrated in vacuo, resulting in compound 119b (20 mg).

119a: Method C; Rt: 3.86 min. m/z=: 844.5 $(M+H)^+$ Exact mass: 843.4

SFC: Column: Chiralcel OJ-H 250 mm*4.6 mm; 5 um; Flow: 2.35 mL/min; Mobile phase: A: $CO_2$ B: MeOH (0.05% Diethylamine); 30% B in A,: Rt: 4.45 min $^1$H NMR (400 MHz, DMSO-$d_6$; main isomer described) δ ppm 0.82-0.99 (m, 12 H), 1.17-2.43 (m, 17 H), 3.54 (s, 3 H), 3.55 (s, 3 H) 3.78-3.89 (m, 2 H), 3.95 (t, J=8.5 Hz, 1 H), 4.09 (t, J=8.3 Hz, 1 H), 4.41-4.53 (m, 1 H), 4.76-4.85 (m, 1 H), 5.08-5.16 (m, 1 H), 5.88 (s, 1 H), 7.30 (d, J=8.5 Hz, 1 H), 7.53 (d, J=8.0 Hz, 1 H), 7.63-7.67 (m, 1 H), 7.72-7.80 (m, 1 H), 7.82-8.06 (m, 5 H), 8.11-8.18 (m, 1 H), 8.22-8.33 (m, 2 H), 11.77-11.92 (m, 2 H)

119b: Method B; Rt: 5.20 min. m/z=: 844.3 $(M+H)^+$ Exact mass: 843.4

SFC: Column: Chiralcel OJ-H 250 mm*4.6 mm; 5 um; Flow: 2.35 mL/min; Mobile phase: A: $CO_2$ B: MeOH (0.05% Diethylamine); 30% B in A,: Rt: 3.22 min SFC: Column: Chiralcel OJ-H 250 mm*4.6 mm; 5 um; Flow: 2.35 mL/min; Mobile phase: A: $CO_2$ B: EtOH (0.05% Diethylamine); 5% to 40% B in A,: Rt: 7.91 min

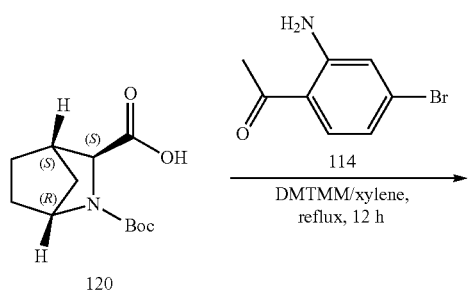

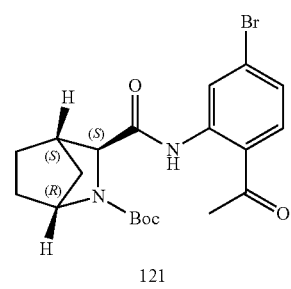

Compound 120 (1.0 g, 4.14 mmol), 4 A molecular sieve (1.0 g) and compound 114 (0.9 g, 4.14 mmol) in xylene (10 mL) were stirred and refluxed for 1 hour. 4-(4,6-Dimethoxy-1,3,5-triazin-2-yl)-4-methylmorpholinium chloride (DMTMM, 1.3 g, 4.6 mmol) was added and the mixture was stirred and refluxed for 12 hours. The mixture was filtrated and the filtrate was concentrated in vacuo. The obtained residue was purified by silica gel column chromatography (eluent: petroleum ether/$CH_2Cl_2$=1/1 then petroleum ether/ethyl acetate=1/1 v/v). resulting in compound 121 (0.6 g).

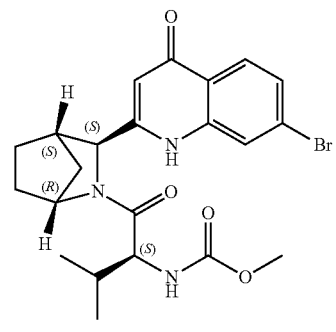

Compound 121 (0.6 g, 1.37 mmol) and NaOH (0.2 g, 5 mmol) in dioxane (10 mL) were stirred for 1 hour at 100° C. under $N_2$. The mixture was poured into 10% $NH_4Cl$ (50 mL) and the organic solvent was removed in vacuo. The mixture was extracted with $CH_2Cl_2$ (2×50 mL). The organic layers were washed with brine, dried and concentrated in vacuo. The obtained residue (0.6 g) was stirred for 2 hours at 20° C. in HCl/dioxane (10 mL). The mixture was concentrated in vacuo. The obtained mixture (0.6 g), (S)-2-(methoxycarbonylamino)-3-methylbutanoic acid (0.36 g, 2.1 mmol), EDC.HCl (0.4 g, 2.1 mmol) and HOBt (0.09 g, 0.69 mmol) in $CH_2Cl_2$ (10 mL) were stirred at 0° C. DIEA (0.9 g, 6.9 mmol) was added. The mixture was stirred for 12 hours at 20° C. The mixture was washed twice with $H_2O$, brine, dried and evaporated in vacuo. The residue was purified by silica gel column chromatography (eluent: ethyl acetate then $CH_3OH$). The pure fractions were collected and the solvent was concentrated in vacuo resulting in compound 122 (0.3 g).

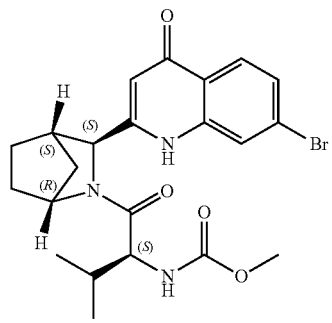

122

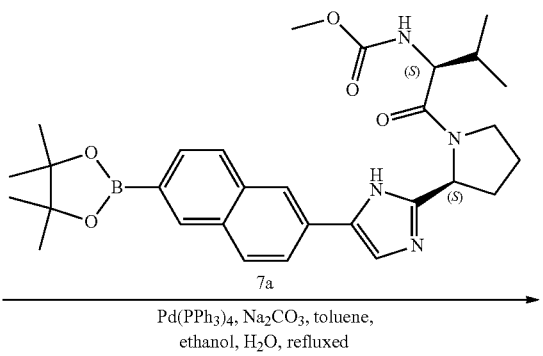

7a

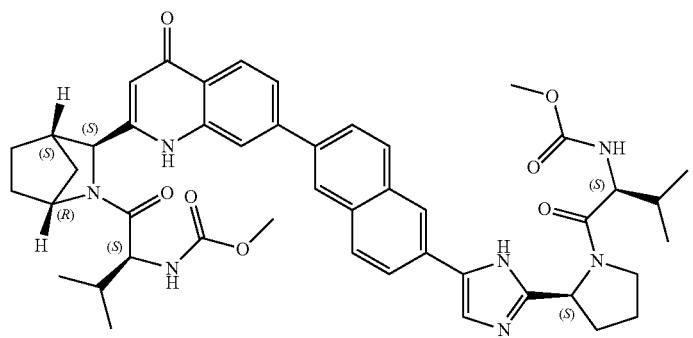

123

Compound 122 (0.3 g, 0.6 mmol), compound 7a (0.33 g, 0.6 mmol), Pd(PPh$_3$)$_4$ (0.066 g, 0.18 mmol), Na$_2$CO$_3$ (0.252 g, 0.24 mmol) in toluene (6 mL), CH$_3$CH$_2$OH (6 mL) and H$_2$O (6 mL) were refluxed under N$_2$ for 12 hours. The solvent was removed in vacuo. The mixture was extracted with CH$_2$Cl$_2$ (2×20 mL). The combined organic layers were washed with brine, dried and evaporated in vacuo.

The residue was purified by preparative silica gel TLC (eluent: CH$_2$Cl$_2$/CH$_3$OH=10/1).

The pure fractions were collected and the solvent was concentrated in vacuo.

The residue was further purified by high-performance liquid chromatography (C18, eluent: CH$_3$CN/H$_2$O from 15/85 to 35/65 with 0.1% CF$_3$COOH as buffer). The pure fractions were collected, neutralized by saturated NaHCO$_3$ and the organic solvent was evaporated. The resulting mixture was extracted with CH$_2$Cl$_2$. The organic layer was separated, washed with brine and dried over Na$_2$SO$_4$. The organic layer was filtered and concentrated in vacuo. The residue was solidified by tert-butyl methyl ether and then co-evaporated with CH$_3$CN, resulting in compound 123 (136.6 mg). Method C; Rt: 3.70 min. m/z=: 816.3 (M+H)$^+$ Exact mass: 815.4; SFC: Column: Chiralcel OJ-H 250 mm*4.6 mm; 5 um; Flow: 2.35 mL/min; Mobile phase: A: CO$_2$ B: EtOH (0.05% Diethylamine); 5 to 40% B in A,: minor isomer (4.6%) Rt: 7.97 min; major isomer (95.4%), Rt: 8.37 min,

BIOLOGICAL EXAMPLES

Anti-HCV Activity of Compounds of Formula I

Replicon Assay

The compounds of formula (I) were examined for inhibitory activity in the HCV replicon. This cellular assay is based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

In essence, the method was as follows:

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is flanked by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which represent the amount of compound required to decrease the level of detected luciferase activity by 50%, or more specifically, to reduce the ability of the genetically linked HCV replicon RNA to replicate.

Results

Where a compound of formula (I) was tested more than once in the replicon assay, the average of all test results is given in this Table 1.

| STRUCTURE | Compound nr. | HCV-REP-HUH7LUC_$EC_{50}$ (nM) |
|---|---|---|
| 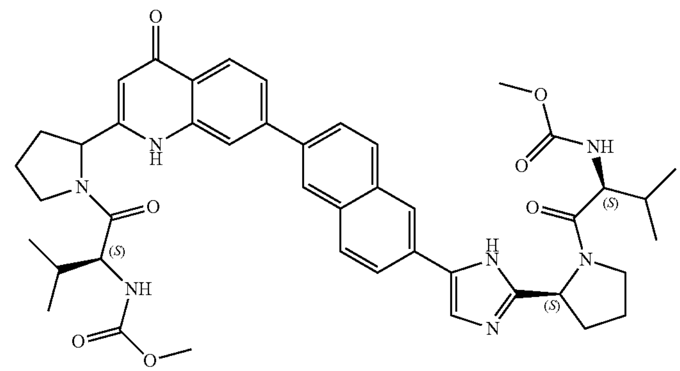 | 13 | 0.028 |
| | 13a | 0.91 |
| | 13b | 0.022 |
| 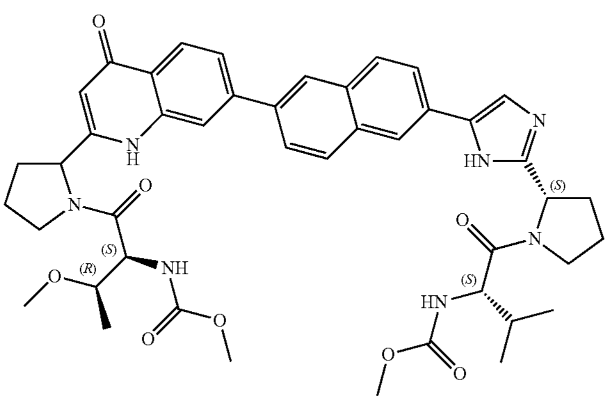 | 13-A1 | 0.1 |
| 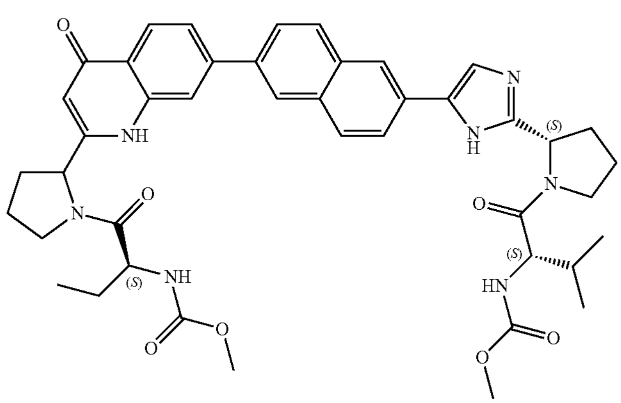 | 13-A2 | 0.079 |

-continued

| STRUCTURE | Compound nr. | HCV-REP-HUH7LUC_EC$_{50}$ (nM) |
|---|---|---|
| 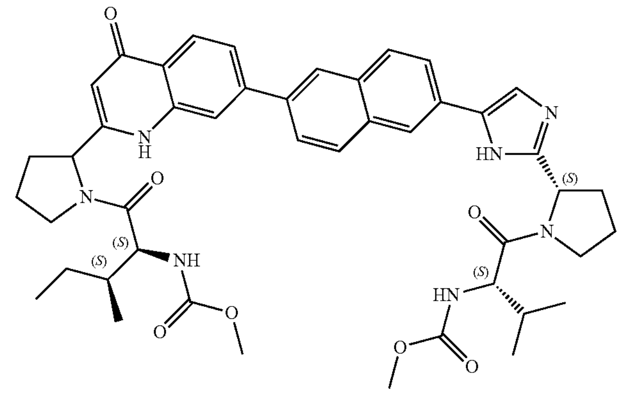 | 13-A3 | |
| 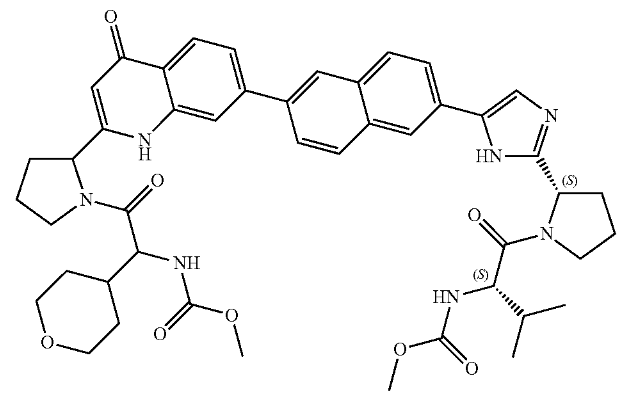 | 13-A4 | 1.2 |
| 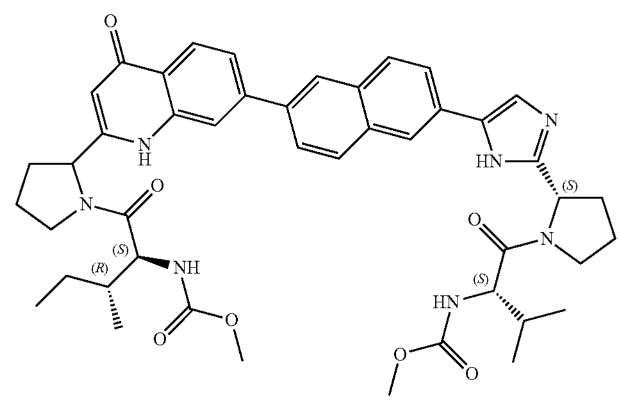 | 13-A5 | 0.062 |
| 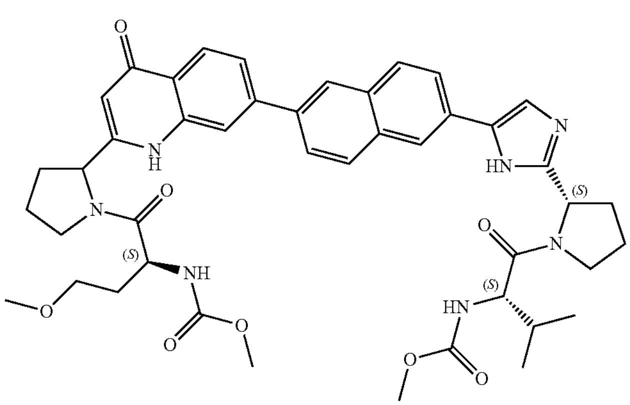 | 13-A6 | 0.5 |

-continued
| STRUCTURE | Compound nr. | HCV-REP-HUH7LUC_EC$_{50}$ (nM) |
|---|---|---|
| 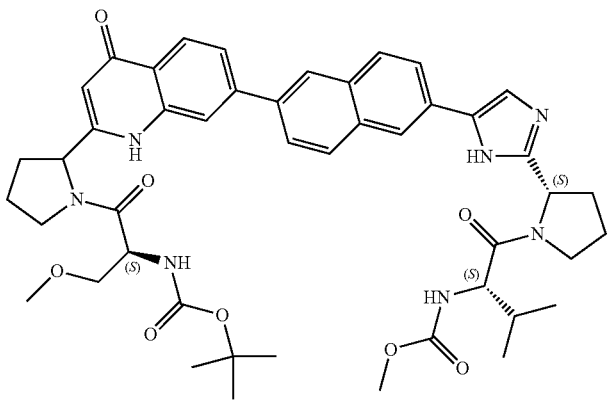 | 13-A7 | 0.053 |
| 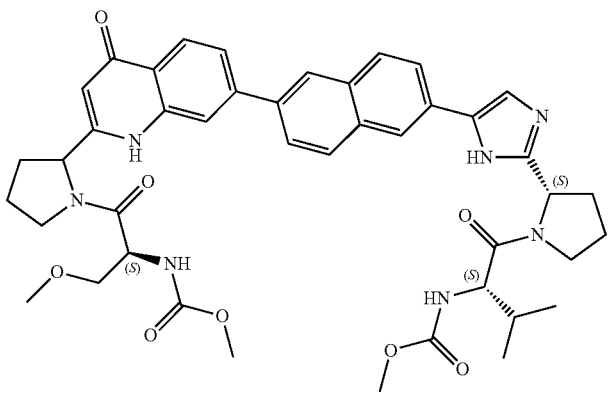 | 13-A8 | 0.18 |
| 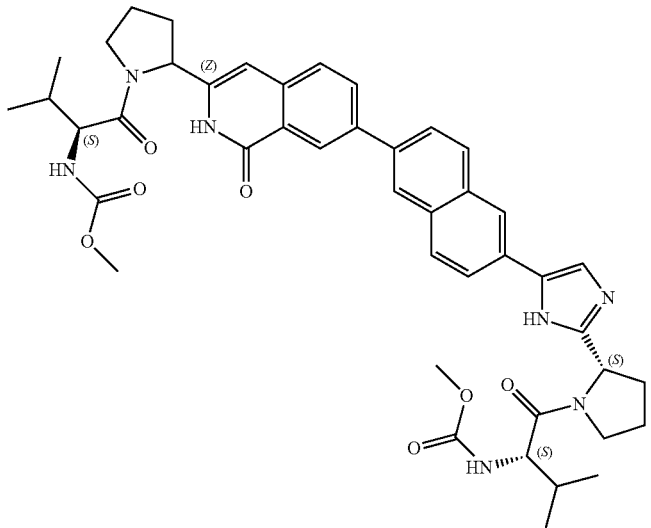 | 20 | 0.79 |

| STRUCTURE | Compound nr. | HCV-REP-HUH7LUC_$EC_{50}$ (nM) |
|---|---|---|
| 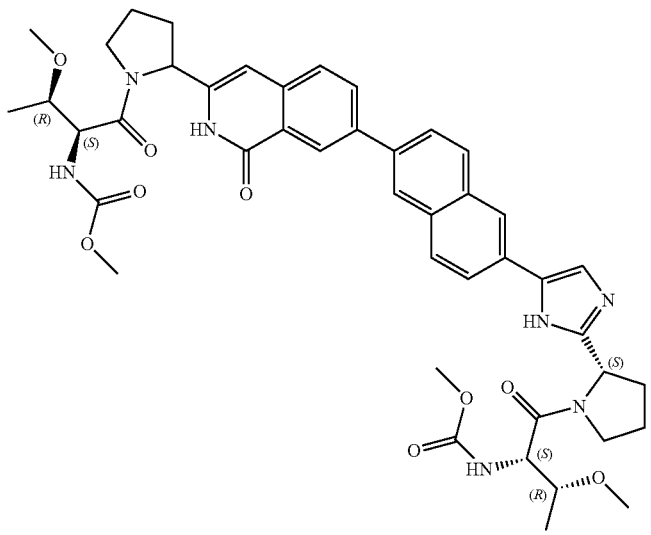 | 20-A | 0.2 |
| 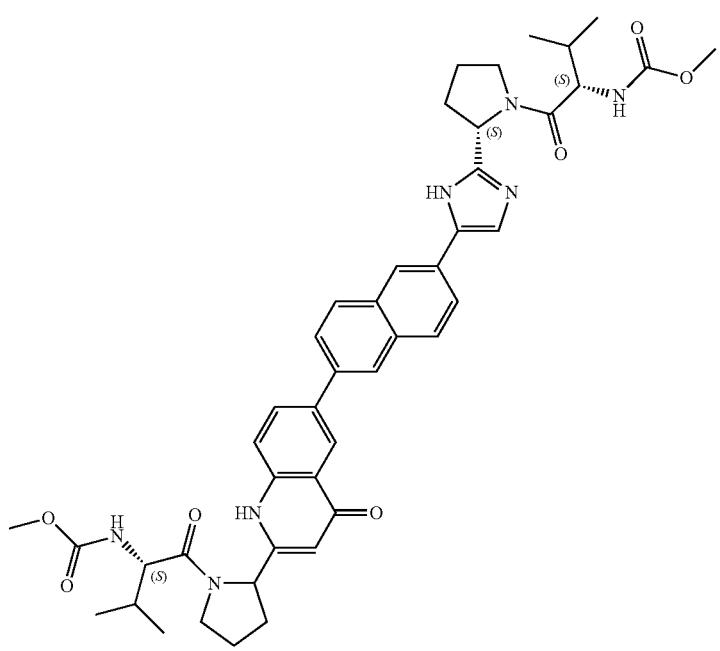 | 22 | 0.075 |

-continued

| STRUCTURE | Compound nr. | HCV-REP-HUH7LUC_EC$_{50}$ (nM) |
|---|---|---|
| | 22a | 3.4 |
| | 22b | 0.052 |
| 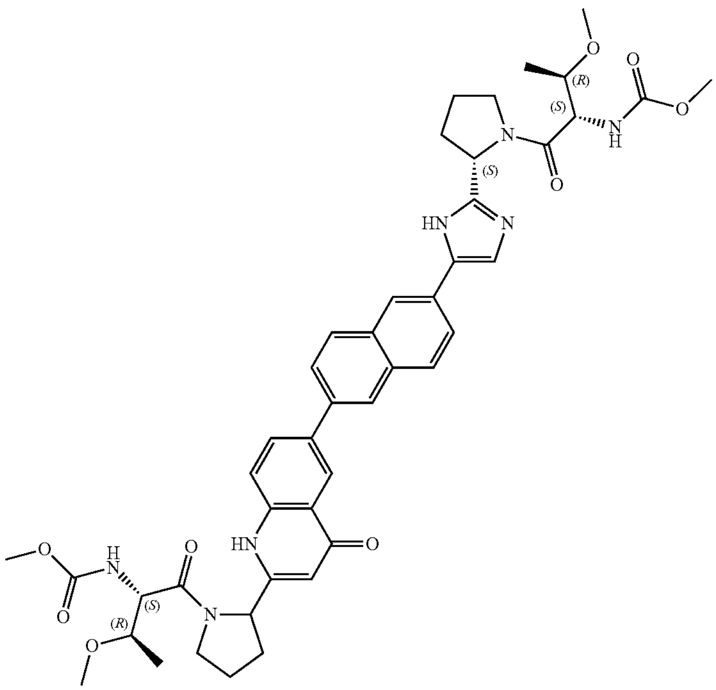 | 23 | 0.47 |
| | 23a | |
| | 23b | 0.34 |
| 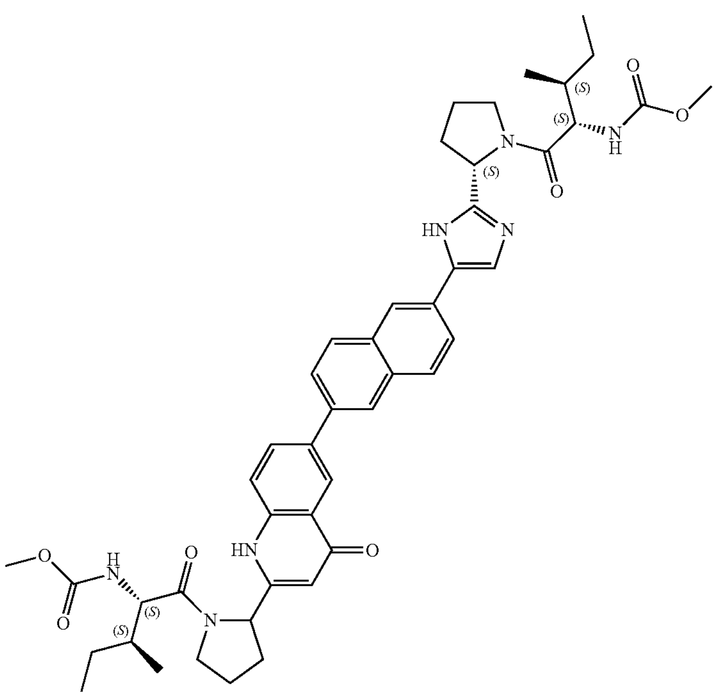 | 24 | 0.048 |

-continued

| STRUCTURE | Compound nr. | HCV-REP-HUH7LUC_EC$_{50}$ (nM) |
|---|---|---|
| | 24a | 9.6 |
| | 24b | |
| 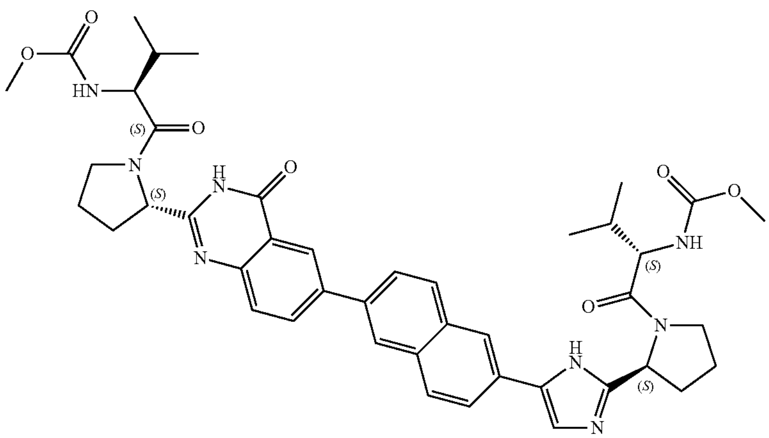 | 35 | 0.64 |
| 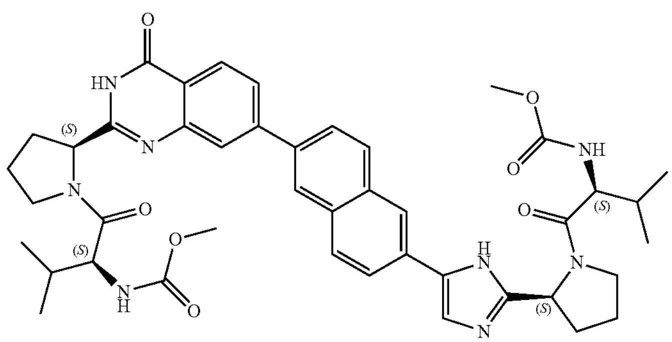 | 44 | 0.005 |
| 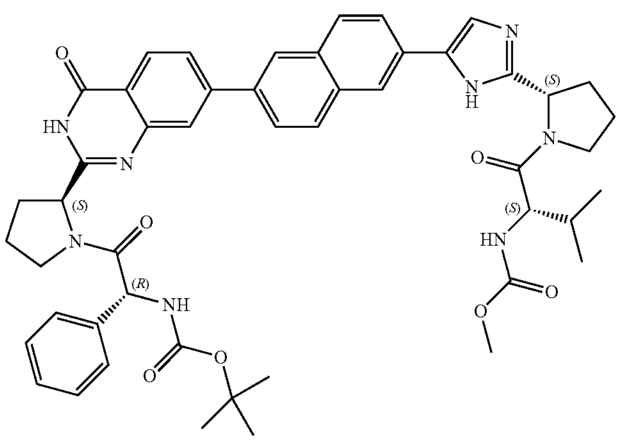 | 44-1 | 8.1 |

-continued
| STRUCTURE | Compound nr. | HCV-REP-HUH7LUC_EC$_{50}$ (nM) |
|---|---|---|
| 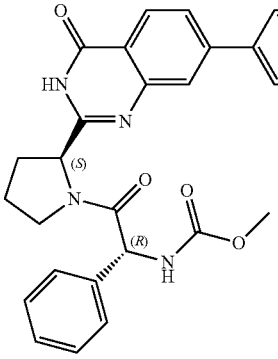 | 44-2 | 0.084 |
| 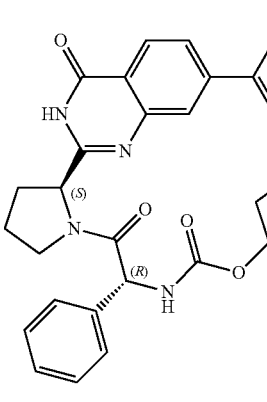 | 44-3 | 1.0 |
| 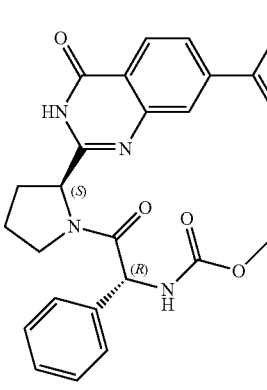 | 44-4 | 9.8 |
| 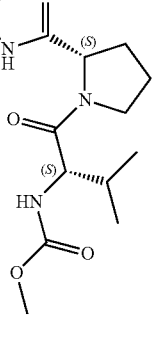 | 50 | 0.006 |

-continued

| STRUCTURE | Compound nr. | HCV-REP-HUH7LUC_EC$_{50}$ (nM) |
|---|---|---|
| 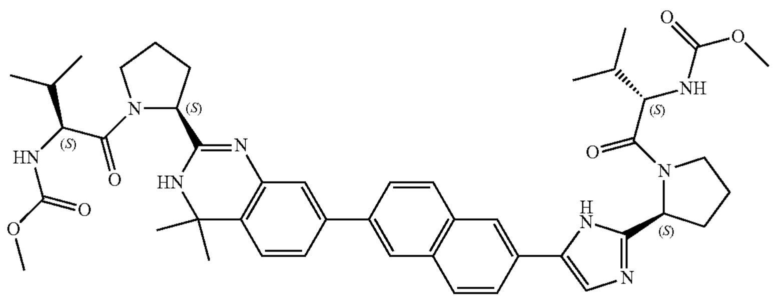 | 61 | 0.017 |
| 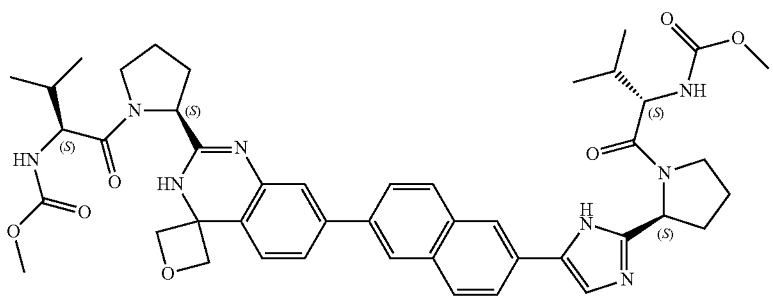 | 70 | 0.009 |
| 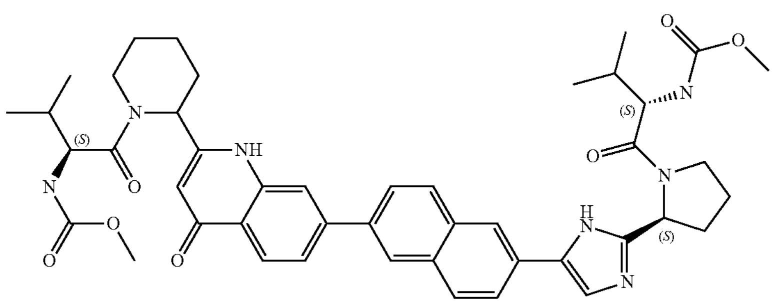 | 76 | 0.034 |
| 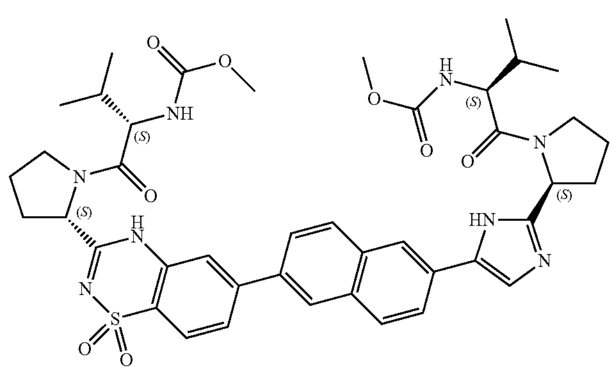 | 84 | 0.034 |

-continued

| STRUCTURE | Compound nr. | HCV-REP-HUH7LUC_EC$_{50}$ (nM) |
|---|---|---|
| 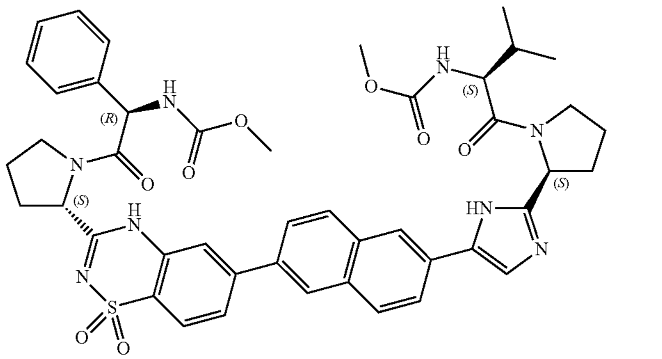 | 87 | 0.008 |
| 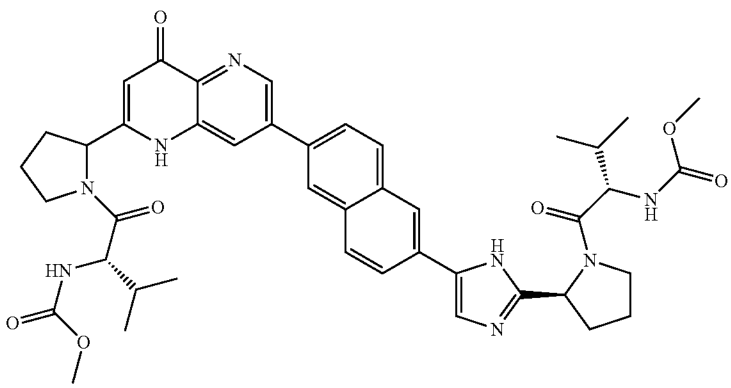 [SMILES: COC(=O)N[C@H](C(=O)N1CCCC1c1cc(=O)c2ncc(-c3ccc4cc(-c5cnc([C@@H]6CCCN6C(=O)[C@@H](NC(=O)OC)C(C)C)[nH]5)ccc4c3)cc2[nH]1)C(C)C] | 97 | 0.24 |
| 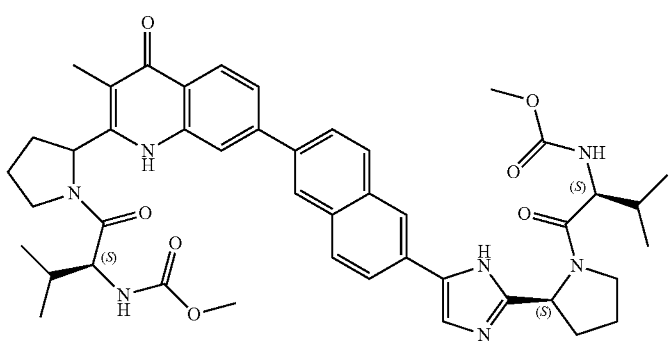 | 102 | |
| | 102a | 0.069 |
| | 102b | 20.6 |
| 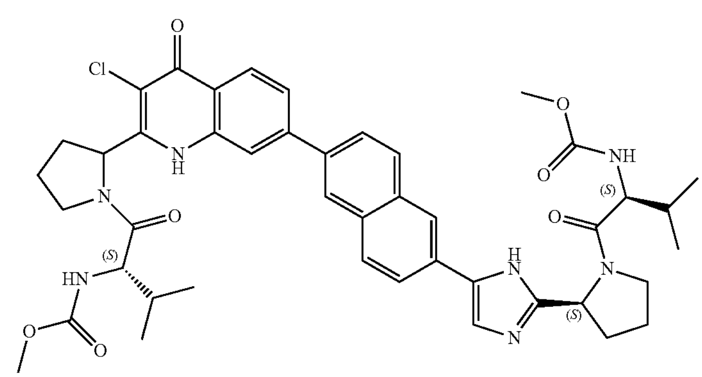 | 106 | |

-continued

| STRUCTURE | Compound nr. | HCV-REP-HUH7LUC_EC$_{50}$ (nM) |
|---|---|---|
| | 106a | 0.12 |
| | 106b | 20.6 |
| | 110 | |
| (structure 110) | 110a | 0.048 |
| | 110b | 0.48 |
| | 119 | |
| (structure 119) | 119a | 0.033 |
| | 119b | |
| | 123 | |
| (structure 123) | | |

Assay Description for the Measurement of Transepithelial Transport of Test Compounds Through LLC-MDR1 Monolayers The apical to basolateral (AtoB) permeability of the test compounds in the presence the P-gp inhibitor GF120918 ($P_{app}$>10$^{-6}$ cm/sec) were measured following an incubation period of 120 minutes. The integrity of the cellular monolayer was assessed in each incubation well through the inclusion of the fluorescent, low permeability marker compound, Fluorescein.

In detail, LLC-MDR1 cells (LLC-PK1 cells stably transduced with MDR1 in a trans-well system) were seeded on 24-well cell culture inserts (Millicell®-PCF, 0.4 μm, 13 mm Ø, 0.7 cm$^2$) at 400 000 cells/cm$^2$. Cell culture medium consists of Medium 199 supplemented with 10% Fetal Bovine Serum (FBS) and 100 U/mL Penicillin/streptomycin and was replaced the day after seeding and the day before the experiment. The transport experiment was performed 5 days after seeding. On the day of the experiment, solutions of the test compounds were applied to the apical side of the monolayers to assess transport in the AtoB direction,. The medium used in the assay was (OPTI-MEM (1×) (GIBCO) with 1 w/v % Bovine Serum Albumin. Inserts were incubated at 37° C. in a humidified incubator containing 5% CO$_2$. Samples from the acceptor and donor compartments were collected after an incubation time of 120 min, to assess the permeability and to allow estimation of the test compound recovery during the experiment, respectively. Transport experiments were performed in triplicate. Absolute test compound concentrations were measured using LC-MS/MS and quantified via a calibration curve.

| Compound number | A->B permeability ($P_{app}$ × $10^{-6}$ cm/sec) in the presence the P-gp inhibitor GF120918 |
|---|---|
| 44 | 6.9 |
| 35 | 5.0 |
| 13b | 0.5 |
| 13A-3 | 0.9 |
| 44-1 | 2.7 |
| 44-2 | 5.5 |
| 50 | 5.8 |
| 61 | 4.8 |
| 70 | 7.8 |
| 76 | 3.1 |
| 84 | 0.4 |
| 87 | 1.0 |
| 102a | <0.6 |
| 110a | 0.4 |
| 110b | 2.3 |

The invention claimed is:

1. A compound of Formula I

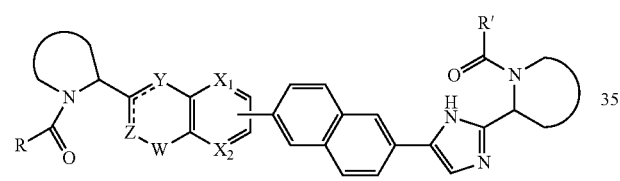

or a stereoisomer thereof, wherein:
each

independently is pyrrolidin-2-yl, 2-aza-bicyclo[3.1.0]hexan-3-yl, piperidin-2-yl, 2-aza-bicyclo[2.2.1]hept-2-yl or octahydro-1H-indol-2-yl wherein each of said heterocycles may optionally be substituted by one or more halogen atoms;

Z⸺C⸺Y is $CR_4$=C—NH, NH—C=CH or NH—C=N;
$X_1$ is CH and $X_2$ is CH; or
$X_1$ is CH and $X_2$ is N; or
$X_1$ is N and $X_2$ is CH;
W is carbonyl, sulfonyl or $CR_5R_6$;
R and R' are independently selected from —$CR_1R_2R_3$, aryl optionally substituted with 1 or 2 substituents selected from halo and methyl, or heterocycloalkyl, wherein
$R_1$ is selected from $C_{1-4}$alkyl optionally substituted with methoxy, hydroxyl or dimethylamino; $C_{3-6}$cycloalkyl; tetrahydropyranyl; phenyl optionally substituted with 1, 2 or 3 substituents independently selected from halo, $C_{1-4}$alkoxy, trifluoromethoxy or 2 substituents on adjacent ring atoms form a 1,3-dioxolane group; benzyl optionally substituted with halo or methoxy; heteroaryl; and heteroarylmethyl;
$R_2$ is selected from hydrogen, hydroxyl, amino, mono- or di-$C_{1-4}$alkylamino, ($C_{3-6}$cycloalkyl)($C_{1-4}$alkyl)amino, $C_{1-4}$alkylcarbonylamino, phenylamino, $C_{1-4}$alkyloxycarbonylamino, ($C_{1-4}$alkyloxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and
$R_3$ is hydrogen or $C_{1-4}$alkyl, or
$CR_2R_3$ together forms carbonyl; or
$CR_1R_3$ forms a cyclopropyl group;
$R_4$ is hydrogen, $C_{1-4}$alkyl or cyano;
$R_5$ and $R_6$, each independently, are $C_{1-4}$alkyl; or
$CR_5R_6$ together form $C_{3-7}$cycloalkyl, oxetane, tetrahydrofurane;
or a pharmaceutically acceptable salts or a solvate thereof.

2. The compound of claim 1, wherein each each

independently is pyrrolidin-2-yl, 2-aza-bicyclo[3.1.0]hexan-3-yl or piperidin-2-yl.

3. The compound of claim 1, wherein each

independently is pyrrolidin-2-yl or 2-aza-bicyclo[3.1.0]hexan-3-yl, wherein each of said heterocycles may optionally be substituted by one or more halogen atoms.

4. The compound of claim 1, wherein Z⸺C⸺Y is CH=C—NH.

5. The compound of claim 1, wherein R and R' are the same.

6. The compound of claim 1, wherein $R_2$ is hydroxyl, amino, mono- or di-$C_{1-4}$alkylamino, $C_{1-4}$alkyl-carbonylamino, $C_{1-4}$alkyloxy-carbonylamino.

7. The compound of claim 1, wherein $R_1$ is selected from $C_{1-4}$alkyl; $C_{2-4}$alkyl substituted with methoxy or hydroxyl; phenyl; and phenyl substituted with 1 or 2 substituents independently selected from halo and methyl.

8. The compound of claim 1, which is

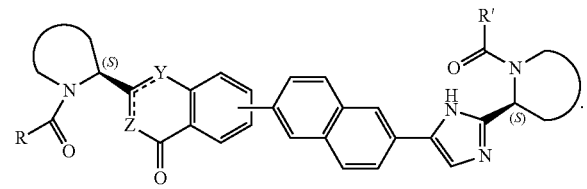

9. A pharmaceutical composition comprising a compound of claim 1 and a pharmaceutically acceptable carrier.

10. A product containing (a) a compound of claim 1, and (b) another HCV inhibitor, as a combined preparation for simultaneous, separate or sequential use in the treatment of HCV infections.

11. A method for the treatment of an HCV infection comprising administering the pharmaceutical composition of claim 9 to a patient in need thereof.

* * * * *

UNITED STATES PATENT AND TRADEMARK OFFICE
CERTIFICATE OF CORRECTION

PATENT NO. : 8,815,849 B2
APPLICATION NO. : 13/812388
DATED : August 26, 2014
INVENTOR(S) : Vandyck et al.

It is certified that error appears in the above-identified patent and that said Letters Patent is hereby corrected as shown below:

In the Claims

Column 170, lines 22-31, claim 2 should read:

2. The compound of claim 1, wherein each

independently is pyrrolidin-2-yl, 2-aza-bicyclo[3,1,0]hexan-3-yl or piperidin-2-yl.

Column 170, lines 47-49, claim 6 should read:

6. The compound of claim 1, wherein $R_2$ is hydroxyl, amino, mono- or di-$C_{1-4}$alkylamino, $C_{1-4}$alkyl- carbonylamino or $C_{1-4}$alkyloxy-carbonylamino.

Signed and Sealed this
Thirteenth Day of January, 2015

Michelle K. Lee
*Deputy Director of the United States Patent and Trademark Office*